US007371834B2

(12) United States Patent
Penninger et al.

(10) Patent No.: US 7,371,834 B2
(45) Date of Patent: May 13, 2008

(54) APOPTOSIS-INDUCING FACTOR

(75) Inventors: Josef M. Penninger, Toronto (CA); Guido P. Kroemer, Paris (FR); David Peter Siderovski, Chapel Hill, NC (US); Naoufal Zamzami, Timbaud (FR); Santos A. Susin, Paris (FR); Bryan E. L. Snow, Toronto (CA)

(73) Assignees: Amgen Inc., Thousand Oaks, CA (US); Centre National de la Recherche Scientifique, Paris (FR)

( * ) Notice: Subject to any disclaimer, the term of this patent is extended or adjusted under 35 U.S.C. 154(b) by 444 days.

(21) Appl. No.: 10/308,936

(22) Filed: Dec. 2, 2002

(65) Prior Publication Data
US 2003/0211514 A1 Nov. 13, 2003

Related U.S. Application Data

(62) Division of application No. 09/447,497, filed on Nov. 23, 1999, now Pat. No. 6,773,911.

(60) Provisional application No. 60/109,595, filed on Nov. 23, 1998.

(51) Int. Cl.
*C07H 21/02* (2006.01)
*A61K 31/70* (2006.01)

(52) U.S. Cl. ....................... 536/23.1; 514/44
(58) Field of Classification Search ............... 530/350; 514/1; 536/23.1
See application file for complete search history.

(56) References Cited

U.S. PATENT DOCUMENTS

| | | |
|---|---|---|
| 4,179,337 A | 12/1979 | Davis et al. |
| 4,341,761 A | 7/1982 | Ganfield et al. |
| 4,342,566 A | 8/1982 | Theofilopoulos et al. |
| 4,399,121 A | 8/1983 | Albarella et al. |
| 4,427,783 A | 1/1984 | Newman et al. |
| 4,444,887 A | 4/1984 | Hoffmann |
| 4,451,570 A | 5/1984 | Royston et al. |
| 4,466,917 A | 8/1984 | Nussenzweig et al. |
| 4,472,500 A | 9/1984 | Milstein et al. |
| 4,491,632 A | 1/1985 | Wands et al. |
| 4,493,890 A | 1/1985 | Morris |
| 4,631,211 A | 12/1986 | Houghten |
| 4,650,764 A | 3/1987 | Temin et al. |
| 4,816,397 A | 3/1989 | Boss et al. |
| 4,816,567 A | 3/1989 | Cabilly et al. |
| 4,925,673 A | 5/1990 | Steiner et al. |
| 4,946,778 A | 8/1990 | Ladner et al. |
| 4,980,289 A | 12/1990 | Temin et al. |
| 4,981,784 A | 1/1991 | Evans et al. |
| 5,010,175 A | 4/1991 | Rutter et al. |
| 5,013,556 A | 5/1991 | Woodle et al. |
| 5,124,263 A | 6/1992 | Temin et al. |
| 5,284,656 A | 2/1994 | Platz et al. |
| 5,288,641 A | 2/1994 | Roizman |
| 5,399,346 A | 3/1995 | Anderson et al. |
| 5,723,323 A | 3/1998 | Kauffman et al. |

FOREIGN PATENT DOCUMENTS

| | | |
|---|---|---|
| CA | 2012311 | 3/1990 |
| EP | 0 401 384 A1 | 12/1990 |
| WO | WO 88/03168 | 5/1988 |
| WO | WO 90/03431 | 4/1990 |
| WO | WO 90/10697 | 9/1990 |
| WO | WO 90/14092 | 11/1990 |
| WO | WO 91/06666 | 5/1991 |
| WO | WO 91/09955 | 7/1991 |
| WO | WO 9109950 | 7/1991 |
| WO | WO 92/00252 | 1/1992 |
| WO | WO 95/07358 | 3/1995 |
| WO | WO 96/40864 | 12/1996 |
| WO | WO 97/25428 | 7/1997 |
| WO | WO 97/35006 | 9/1997 |
| WO | WO 98/22589 | 5/1998 |
| WO | WO 00/20604 | 4/2000 |

OTHER PUBLICATIONS

Susin et al. J. Exp. Med. 1996, 184:1331-1341.*
Watson et al (Biochem J., Jan. 15, 1988, 249:345-350).*
Deas et al (J. Immunology, Oct. 1, 1998, 161(7):3375-3383).*
Gura (Science, 1997, 278:1041-1042).*
Watson et al (Biochem J., Jan. 15, 1988, 249:345-350).*
Adej, A. et al., "Pulmonary Delivery of Peptide Drugs: Effect of Particle Size on Bioavailability of Leuprolide Acetate in Healthy Male Volunteers," *Pharmaceutical Research*, 7(6):565-569 (1990).
Bossy-Wetzel, E., "Mitochondrial cytochrome c release in apoptosis occurs upstream of DEVD-specific caspase activation and independently of mitochondrial transmembrane depolarization," *EMBO J.*, 17:37-49 (1998).
Boulikas, T., "Nuclear Localization Signals (NLS)," *Crit. Rev. Eukaryotic Gene Expression*, 3(3):193-227 (1993).
Cecconi, F. et al., "Apaf1 (CED-4 Homolog) Regulates Programmed Cell Death in Mammalian Development," *Cell*, 94:727-737 (Sep. 1998).
Cedano, J. et al., "Relation Between Amino Acid Composition and Cellular Location of Proteins," *J. Mol. Biol.*, 266:594-600 (1997).
Claros, M.G. et al., "Computational method to predict mitochondrially imported proteins and their targeting sequences," *Eur. J. Biochem.*, 241:779-786 (1996).
Dickson, A.J., "Apoptosis regulation and its applications to biotechnology," *TIBTECH*, 16:339-342 (Aug. 1998).
EMBL Accession No. Z81364, Human DNA sequence from PAC 179D3, between markers DXS6791 and DXS8038 on chromosome X contains ESTs and CpG islands, Nov. 23, 1999.
Enari, M. et al., "A caspase-activated DNase that degrades DNA during apoptosis, and its inhibitor ICAD," *Nature*, 391:43-50 (Jan. 1998).

(Continued)

*Primary Examiner*—Misook Yu
*Assistant Examiner*—Sean E Aeder
(74) *Attorney, Agent, or Firm*—Marshall, Gerstein & Borun LLP

(57) ABSTRACT

The present invention related generally novel mammalian apoptosis-inducing factors, polynucleotides encoding such factors and methods related thereto.

12 Claims, 4 Drawing Sheets

OTHER PUBLICATIONS

Enari, M. et al., "Apoptosis by a cytosolic extract from Fas-activated cells," *EMBO J.*, 14(21):5201-5208 (1995).
GENBANK Accession No. AA891591, EST195394 Normalized rat kidney, Bento Soares Rattus sp. cDNA clone RKIAE33 3' end, mRNA sequence, Jan. 25, 1999.
GENBANK Accession No. AF100927 Mus musculus apoptosis-inducing factor AIF (Aif) mRNA, nuclear gene encoding mitochondrial protein, complete cds., Mar. 3, 1999.
GENBANK Accession No. AF100928 *Homo sapiens* apoptosis-inducing factor AIF mRNA, nuclear gene encoding mitochondrial protein, complete cds., Mar. 3, 1999.
GENBANK Accession No. AA068609, mm48c09.r1 Stratagene mouse melanoma (#937312) Mus musculus cDNA clone IMAGE:5247525 5', mRNA sequence, Feb. 6, 1997.
GENBANK Accession No. AA07349, mm95b11.r1 Stratagene mouse heart (#937316) Mus musculus cDNA cone IMAGE:536157 5', mRNA sequence, Feb. 15, 1997.
GENBANK Accession No. AA088093, mo01g11.r1 Stratagene mouse lung 937302 Mus musculus cDNA clone IMAGE:552356 5' similar to SW:BEDA_PSEPU Q07946 Benzene 1,2-Dioxygenase System Ferredoxin—NAD(+) Reductase Component; mRNA sequence, Feb. 15, 1997.
GENBANK Accession No. AA106466, m194h01.r1 Stratagene mouse kidney (#937315) Mus musculus cDNA clone IMAGE:519697 5', mRNA sequence, Feb. 4, 1997.
GENBANK Accession No. AA134414, zo26d10.r1 Stratagene colon (#937204) Homo sapiens cDNA cone IMAGE:588019 5', mRNA sequence, Aug. 6, 1997.
GENBANK Accession No. AA155062, mr91e09.r1 Stratagene mouse embryonic carcinoma (#937317) Mus musculus cDNA clone IMAGE:604840 5' similar to SW:BEDA_PSEPU Q07946 Component; mRNA sequence, Feb. 11, 1997.
GENBANK Accession No. AA337888, EST42857 Endometrial tumor Homo sapiens cDNA 5' lend, mRNA sequence, Apr. 21, 1997.
GENBANK Accession No. AA516860, vh88e09.r1 Knowles Solter mouse embryonic stem cell Mus musculus cDNA clone IMAGE:894088 5' similar to SW:BEDA_PSEPU Q07946 Benzene 1,2-Dioxygenase System Ferredoxin—Nad(+) Reductase Component; mRNA sequence, Jul. 14, 1997.
GENBANK Accession No. AA570483, nk64b03.s1 NCI_CGAP_Sch1 Homo sapiens cDNA clone IMAGE:1018253 3', mRNA sequence, Sep. 9, 1997.
GENBANK Accession No. AA572575, v181h05.r1 Stratagene mouse diaphragm (#937303) Mus musculus cDNA clone IMAGE:987129 5', mRNA sequence, Aug. 27, 1997.
GENBANK Accession No. H15605, ym27d05.r1 Soares infant brain 1NIB Homo sapiens cDNA clone IMAGE:49496 5", mRNA sequence, Jun. 27, 1995.
GENBANK Accession No. W77437, me64e08.r1 Soares mouse embryo NbME13.5 14.5 Mus musculus cDNA clone IMAGE:400358 5' similar to SW:BEDA_PSEPU Q07946 Benezene 1,2-Dioxygenase System Ferredoxin—Nad(+) Redyctase Component; mRNA sequence, Jun. 20, 1996.
GENBANK Accession No. C03711 Human heart cDNA (YNakamura) *Homo sapiens* cDNA clone 3NHC2062, mRNA sequence, Jul. 30, 1996.
GI:1595214; GenBank Accession No. AA073449, mm95b11.r1 Stratagene mouse heart (3937316) Mus musculus cDNA clone IMAGE:536157 5', mRNA sequence, Feb. 15, 1997.
Green, D.R., et al., "Mitochondria and Apoptosis," *Science*, 281:1309-1312 (Aug. 1998).
Green, D.R., "Apoptotic Pathways: The Roads to Ruin," *Cell*, 94:695-698 (Sep. 1998).
Herbein, G. et al., "Apoptosis of CD8+ T cells is mediated by macrophages through interaction of HIV gp 120 with chemokine receptor CXCR4," *Nature*, 395:189-194 (Sep. 1998).
Jacobson, M.D., "Anti-apoptosis therapy: A way of treating neural degeneration?" *Current Biology*, 8:R418-R421 (1998).
Juo, P. et al., "Essential requirement for caspase-8/FLICE in the initiation of the Fas-induced apoptotic cascade," *Current Biology*, 8:1001-1008 (1998).
Kluch, R.M. et al., "Cytochrome *c* activation of CPP32-like proteolysis plays a critical role in a *Xenopus* cell-free apoptosis system," *EMBO J.*, 16(15):4639-4649 (1997).
Kluck, R.M. et al., "The Release of Cytochrome *c* from Mitochoncria: A Primary Site for Bcl-2 Regulation of Apoptosis," *Science*, 275:1132-1136 (1997).
Kroemer, G. et al., "Detection of apoptosis and apoptosis-associated alterations," In: *Immunology Methods Manual*, Lefkovitz, R. (Ed.), Academic Press, Chapter 14.2, pp. 1111-1125 (1997).
Kroemer, G. et al., "The biochemistry of programmed cell death," *FASEB J.*, 9:1277-1287 (1995).
Kroemer, G. et al., "The Mitochondrial Death/Life Regulator in Apoptosis and Necrosis," *Annu. Rev. Physiol.*, 60:619-642 (1998).
Kroemer, G., "The proto-oncogene Bcl-2 and its role in regulating apoptosis," *Nature Medicine*, 3(6):614-620 (1997).
Lagarkova, M.A. et al., "Large-scale Fragmentation of Mammalian DNA in the Course of Apoptosis Proceeds via Excision of Chromosomal DNA Loops and Their Oligomers," *J. Biol Chem.*, 270(35):20239-20241 (1995).
Li, H. et al., "Cleavage of BID by Caspase 8 Mediates the Mitochondrial Damage in the Fas Pathway of Apoptosis," *Cell*, 94:491-501 (Aug. 1998).
Li, P. et al., "Cytochrome *c* and dATP-Dependent Formation of Apaf-1/Caspase-9 Complex Initiates an Apoptotic Protease Cascade," *Cell*, 91:479-489 (Nov. 1997).
Liu, X., et al., "DFF, A Heterodimeric Protein that Functions Downstream of Caspase-3 to Trigger DNA Fragmentation during Apoptosis," *Cell*, 89:175-184 (Apr. 1997).
Liu, X.S. et al., "Induction of Apoptotic Program in Cell-Free Extracts: Requirement for dATP and Cytochrome *c*," *Cell*, 86:147-157 (Jul. 1996).
Mancini, M. et al., "The Caspase-3 Precursor Has a Cytosolic and Mitochondrial Distribution: Implications for Apoptotic Signaling," *Cell Biol.*, 140:1485-1495 (1998).
Marchetti, P. et al., "Mitochondrial Permeability Transition Is a Central Coordinating Event of Apoptosis," *J. Exp. Med.*, 184:1155-1160 (Sep. 1996).
Marchetti, P. et al., "Mitochondrial Permeability Transition Triggers Lymphocyte Apoptosis," *J. Immunology.*, 157:4830-4836 (1996).
Marzo, I. et al., "Bax and Adenine Nucleotide Translocator Cooperate in the Mitochondrial Control of Apoptosis," *Science*, 281:2027-2031 (Sep. 1998).
Oberhammer, F. et al., "Apoptotic death in epithelial cells: cleavage of DNA to 300 and/or 50 kb fragments prior to or in the absence of internucleosomal fragmentation," *EMBO J.*, 12(9):3679-3684 (1993).
Pedersen, P.L. et al., "Preparation and Characterization of Mitochondria and Submitochondrial Particles of Rat Liver and Liver-Derived Tissues," *Meth. Cell Biol.*, 20:411-481 (1978).
Penninger, J.M. et al., "Molecular and Cellular Mechanisms of T Lymphocyte Apoptosis," *Advances in Immunology*, 68:51-144 (1998).
Petit, P.X. et al., "Mitochondria and programmed cell death: back to the future," *FEBS Letters*, 396:7-13 (1996).
Samejima, K. et al., "Transition from Caspase-dependent to Caspase-independent Mechanisms at the Onset of Apoptotic Execution," *J. Cell Biol.*, 143:225-239 (1998).
*Science*, 281(5381):1301-1308 and 1312-1325 (Aug. 1998).
Scott, J.K. et al., "Searching for Peptide Ligands with an Epitope Library" *Science*, 249:386-390 (Jul. 1990).
Shimizu, S. et al., Bcl-2 prevents apoptotic mitochondrial dysfunction by regulating proton flux, *Proc. Natl. Acad. Sci. USA*, 95:1455-1459 (1998).
Snow, B.E. et al., "Cloning of a retinally abundant regulator of G-protein signaling (RGS-r/RGS16): genomic structure and chromosomal localization of the human gene," *Gene.*, 206:247-253 (1998).
Snow, B.E. et al., "Molecular Cloning and Expression Analysis of Rat *Rgs12* and *Rgs14*," *Biochem. Biophy. Res. Comm.*, 233:770-777 (1997).
Staudinger, J. et al., "Interactions among Vertebrate Helix-Loop-Helix Proteins in Yeast Using the Two-hybrid System," *J. Biol. Chem.*, 268(7):4608-4611 (1993).

Susin, S.A. et al., "Bcl-2 Inhibits the Mitochondrial Release of an Apoptogenic Protease," *J. Exp. Med.*, 184:1331-1341 (1996).

Susin, S.A. et al., "Mitochondrial Release of Caspases-2 and -9 during the Apoptotic Process," *J. Exp. Med.*, 189(2):381-393 (1999).

Susin, S.A. et al., "The Central Executioner of Apoptosis: Multiple Comnections between Protease Activation and Mitochondria in Fas/APO-1/CD95- and Ceramide-induced Apoptosis," *J. Exp. Med.*, 186(1):25-37 (1997).

Vander Heiden, M.G. et al., Bcl-$x_L$ Regulates the Membrane Potential and Volume Homeostasis of Mitochondria, *Cell*, 91:627-637 (Nov. 1997).

Wada, J. et al., "Characterization of mammalian translocase of inner mitochondrial membrane (Tim44) isolated from diabetic newborn mouse kidney," *Proc. Natl. Acad. Sci. USA*, 95:144-149 (Jan. 1998).

Zamzami, N. et al., "Mitochondcrial Control of Nuclear Apoptosis," *J. Exp. Med.*, 183:1533-1544 (1996).

Zhu, W. et al., "Bcl-2 mutants with restricted subcellular localization reveal spatially distinct pathways for apoptosis in different cell types," *EMBO J.*, 15:4130-4141 (1996).

Bethke Bruce et al., "Segmental genomic replacement by Cre-mediated recombination: Genomic stress activation of the p53 promoter in single-copy transformants," *Nucleic Acids Research*, 25(14):2828-2834 (1997).

Susin Santos A. et al., "Mitochondria as regulators of apoptosis: Doublt no more," *Biochimica et Biophysica Acta*, 1366(1-2):151-165 (Aug. 1998).

Susin Santos A. et al., "Molecular characterization of mitochondrial apoptosis-inducing factor," *Nature* (London), 397(6718):441-446 (Feb. 1999).

Anderson, B., "A double adaptor method for improved shotgun library construction," *Anal. Biochem.*, 36(1):107-113 (1996).

Burgess et al., "Possible Dissociation of the Heparin-binding and Mitogenic Activities of Heparin-binding Growth Factor-1 from its Receptor-binding Activities by Site-directed Mutagenesis of a Single Lysine Residue," *Journal of Cellular Biology*, 111:2129-2138 (Nov. 1990).

Farrow et al., "Cloning of a bcl-2 homologue by interaction with adenovirus E1B 19K," *Nature*, 374(6524): 731-733 (1995).

Frisch et al., "A Soluble Immunoglobin Variable Domain without a Disulfide Bridge: Construction, Accumulation in the Cytoplasm of *E. coli* Purification and Physicochemical Characterization," *Biol. Chem.*, Hoppe-Seyler, 375(5):353-356 (May 1994).

Green, et al., "Sequence of the cDNA encoding ovine tumor necrosis factor-alpha: problems with cloning by inverse PCR," *Gene*, 109(2):203-210 (Dec. 1991).

Kim, et al., "Restoring allosterism with compensatory mutations in hemoglobin," *PNAS*, 91(4):11547-11551 (1994).

Kwon, et al., "Cloning and sequence analysis of the rat tumor necrosis factor," *Gene*, 132(2):227-236 (1993).

Lazar et al., "Transforming Growth Factor Alpha: Mutation of Aspartic Acid 47 and Leuine 48 Results in Different Biological Activities," *Molecular and Cellular Biology*, 8:1247-1252 (1988).

Lewin, B.,Genes IV, Oxford University Press (1990).

Marra, et al., Accession No. AA866777, Gencore Version 4.5 (Mar. 1998).

Matthews, B.W. "Genetic and Structural Analysis of the Protein Stability Problem," *Perspectives in Biochemistry*, Hans Neurath (Ed.), American Chemical Society (1989).

Matthews and Van Holde, *Biochemistry*, $2^{nd}$ edition, Benjamin-Cummings Publishing Company (1996).

Nacken et al., "Biochemical characterization of the murine S100A9 protein suggests that its functionally equivalent to its human counterpart despite its low degree of similarity," *Eur. Journal of Biochemistry*, 267(2):560-565 (2000).

Pauli et al., "Porcine tumor necrosis factor alpha: cloning with the polymerase chain reaction and determination of the nucleotide sequence," *Gene*, 81(1):185-191 (Sep. 1989).

Pollock et al., "Bacterial Expression of a Mitochondrial Cytochrome C . . . ," *Biochemistry*, 37(17):6124-6131 (Apr. 1998).

Reiger et al., *Glossary of Genetic and Cytogenetics*, $4^{th}$ edition, Springer-Verlag, New York, pp. 17-18 (1976).

Shakhov et al., "Molecular cloning of the genes coding for tumor necrosis factor," *Bioorganicheskaia Khimiia*, abstract only 13(5):701-705 (1987).

Singh et al., "Death Domain Receptors and Their Role in Cell Demise" *Journal of Interferon and Cytokine Research*, 18(7):439-450 (Jul. 1998).

Shu et al., "Casper is a FADD- and Caspase-Related Inducer of Apoptosis," *Immunity*, 6(6):751-763 (Jun. 1997).

\* cited by examiner

APOPTOSIS-INDUCING FACTOR

This application is a divisional of U.S. Ser. No. 09/447,497, filed Nov. 23, 1999, now U.S. Pat. No. 6,773,911 which claims priority to U.S. Provisional Application No. 60/109,595 filed Nov. 23, 1998. U.S. Ser. No. 09/447,497 and U.S. Ser. No. 60/109,595 are incorporated herein by reference in their entireties.

BACKGROUND OF THE INVENTION

1. Field of the Invention

This invention relates generally to novel mammalian apoptosis-inducing factor (AIF) polypeptides, DNAs encoding for the AIF polypeptides, and uses thereof.

2. Related Technology

Apoptosis is essential for the maintenance of tissue size and cell number homeostasis of multi-cellular organisms, and apoptotic abnormalities are thought to play an important role in the development of various neoplastic diseases as well as a number of neurodegenerative diseases.

Mitochondria play a key role in the regulation of apoptosis. A variety of key events in apoptosis involve mitochondria, including the release of caspase activators (such as cytochrome c), changes in electron transport, loss of mitochondrial transmembrane potential (thus allowing several proteins found within the mitochondrial intermembrane space to be liberated through the outer mitochondrial membrane, thereby participating in the apoptotic degradation phase), altered cellular oxidation-reduction, and which involves the of pro- and anti-apoptotic Bcl-2 family of proteins. The different signals that converge on mitochondria to trigger or inhibit these events and their downstream effects delineate several major pathways in physiological cell death.

Because apoptosis and its regulation plays a critical role in the maintenance of cellular and tissue homeostasis, there exists a need to develop material and methods for either inducing or inhibiting apoptosis as well as to provide systems for screening for additional candidate substances that either induce or inhibit apoptosis.

SUMMARY OF THE INVENTION

The present invention is directed to isolated polynucleotides encoding a mammalian apoptosis-inducing factor or biologically active conserved variants, allelic variants, isoforms, analogs, and fragments thereof, wherein the polynucleotides are selected from the group consisting of cDNA, genomic DNA, and chemically synthesized DNA. In another aspect the invention is directed isolated polynucleotides encoding murine apoptosis-inducing factor or biologically active conserved variants, allelic variants, isoforms, analogs, and fragments thereof. The invention is also directed to isolated polynucleotides encoding human apoptosis-inducing factor or biologically active conserved variants, allelic variants, isoforms, analogs, and fragments thereof. As yet another aspect, the present invention is directed to isolated polynucleotides that encode a polypeptide having at least 70-95 percent identity to the polypeptides comprising the amino acid sequences set forth in SEQ ID NOS: 2, 3, 5, 6, 8, 9, 11, 12, 14, and 15.

The present invention is also directed to isolated polynucleotides encoding a mammalian apoptosis-inducing factor the polynucleotide being selected from the group consisting of: (a) the DNA molecules set forth in SEQ ID NOS: 1, 4, 7, 10, 13, DNA molecules encoding variants including conserved variants, allelic variants, analogs, and fragments thereof; (b) DNA molecules which hybridize, under high stringency conditions, to the DNA molecules defined in (a) or hybridizable fragments thereof; and (c) DNA molecules that code an expression for the amino acids encoded by any of the foregoing DNA molecules.

In another of its aspects, the present invention is directed to expression vectors or cloning vectors comprising any of the disclosed AIF-encoding polynucleotides as well to host cells transformed with any of the disclosed AIF-encoding polynucleotides.

The present invention is also directed to mammalian cells containing a mammalian apoptosis-inducing factor encoding DNA modified so as to permit higher expression of the apoptosis-inducing factor by means of a homologous recombinational event consisting of inserting an expression regulatory sequence in functional proximity to the apoptosis-inducing factor encoding DNA, wherein the inserted expression regulatory sequence is not a native apoptosis-inducing factor expression regulatory sequence.

As yet another aspect, the present invention is directed to methods for producing an apoptosis-inducing factor polypeptide, the method comprising the steps of: (a) culturing a host cell under conditions suitable for the expression of the apoptosis-inducing factor polypeptide; and (b) recovering the expressed apoptosis-inducing factor polypeptide.

The present invention is also directed an isolated purified mammalian apoptosis-inducing factor and biologically active conserved variants, allelic variants, isoforms, analogs, and fragments thereof. The present invention is also directed to an isolated purified murine apoptosis-inducing factor and biologically active conserved variants, allelic variants, isoforms, analogs, and fragments thereof. The present invention is further directed to an isolated purified human apoptosis-inducing factor and biologically active conserved variants, allelic variants, isoforms, analogs, and fragments thereof.

As yet a further aspect of the present invention is directed antibody substances which specifically bind the disclosed apoptosis-inducing factors.

The present invention is also directed to derivatives of the disclosed apoptosis-inducing factors.

The present invention is also directed to methods for determining the presence of mammalian apoptosis-inducing factor in a biological sample comprising the steps of: (a) obtaining a biological sample; (b) exposing said biological sample to a mammalian apoptosis-inducing factor-specific antibody; and (c) detecting the binding of mammalian apoptosis-inducing factor-specific antibody in said biological sample. The present invention is also directed to methods for determining the presence of mammalian apoptosis-inducing factor-specific polynucleotide molecules in a biological sample comprising the steps of: (a) collecting a biological sample;(b) isolating polynucleotide molecules from said biological sample; (c) hybridizing to said polynucleotide molecules a diagnostic reagent; and (d) detecting the binding of the mammalian apoptosis-inducing factor-specific polynucleotide molecules in said biological samples.

The present invention is also directed to methods for determining the presence of mammalian-apoptosis inducing factor-specific polynucleotide molecule in a tissue or cellular sample comprising the steps of: (a) collecting tissue or cellular sample;(b) hybridizing said tissue or cellular sample to a diagnostic reagent; and (c) detecting the binding of the mammalian apoptosis-inducing factor-specific polynucleotide molecules in the tissue or cellular sample to said diagnostic reagent.

As yet another aspect of the invention is directed to methods of identifying a candidate inhibitor of mammalian apoptosis-inducing factor binding to a mammalian apoptosis-inducing factor binding protein comprising the steps of: (a) exposing mammalian apoptosis-inducing factor to a mammalian apoptosis-inducing factor binding protein under conditions which permit binding of mammalian apoptosis-inducing factor to a mammalian apoptosis-inducing factor binding protein in the presence or absence of a candidate inhibitor; (b) measuring the binding of mammalian apoptosis-inducing factor to a mammalian apoptosis-inducing factor binding protein in the presence or absence of the candidate inhibitor; (c) comparing the level of binding observed in step (a); and (d) identifying the compound as an inhibitor of mammalian apoptosis-inducing factor binding by its ability to prevent binding of mammalian apoptosis-inducing factor to a mammalian apoptosis-inducing factor binding protein.

The present invention is also directed to a composition comprising an isolated purified mammalian apoptosis-inducing factor or biologically active conserved variants, allelic variants, isoforms, analogs, and fragments thereof and an acceptable carrier, diluent and/or adjuvant. The present invention is also directed to a murine apoptosis-inducing factor or biologically active conserved variants, allelic variants, isoforms, analogs, and fragments thereof and an acceptable carrier, diluent and/or adjuvant. The present invention is also directed to a human apoptosis-inducing factor or biologically active conserved variants, allelic variants, isoforms, analogs, and fragments thereof and an acceptable carrier, diluent and/or adjuvant As yet another aspect of the invention is directed to methods of inhibiting cell proliferation via administration of any of the disclosed apoptosis-inducing factors or compositions thereof.

Other objectives and advantages of the invention may be apparent to those skilled in the art from a review of the following detailed description including any drawings, as well as the approved claims.

BRIEF DESCRIPTION OF THE DRAWINGS

FIG. 1B shows fluorescent in situ hybridization (FISH) of AIF DNA probe (red fluorescence) on a male mouse karyogram counterstained with DAPI (blue fluorescence). The detailed position of the AIF gene was mapped to chromosome X region A6 (10 determinations with identical results).

FIG. 1C shows the tissue mRNA expression pattern of AIF. An AIF cDNA probe was hybridized to a northern blot of polyadenylated RNA from human pancreas (1), kidney (2), skeletal muscle (3), liver (4), brain (6), placenta (5), and heart (7).

FIG. 1D shows the protein expression pattern of AIF. An antiserum raised against amino acid nos. 151-200 of mouse AIF (mAIF) was used to detect AIF protein contained in mitochondria from mouse liver (1), kidney (2), heart (3), brain (5), or spleen (6). Control blots performed in the presence of the immunogenic peptides covering amino acid nos. 151-200 yield negative results for liver mitochondria.

FIG. 1E shows the mitochondrial import of AIF. In vitro transcription and translation was performed using the TNT Lysate Coupled Transcription/Translation kit (Promega) and [$^{35}$S]methionine in the absence (1) or presence (2) of mAIF cDNA. The retention of this product was measured using mitochondria which were left untreated (3), digested with proteinase K to remove surface-bound protein (4), de-energized with 100 μM CCCP (5) or treated with both proteinase K and CCCP (6). Note the maturation of AIF to a 57 kDa protein which is retained by mitochondria in a CCCP-inhibitable fashion and which is protected from proteolysis.

FIG. 2A shows the submitochondrial localization of AIF, AIF liberation by PT pore opening, and antibody-mediated neutralization of AIF bioactivity contained in the mitochondrial intermembrane space. Western blots were performed on total mouse liver mitochondrion lysate (1), proteins from the matrix (2), inner membrane (3), intermembrane space (4), outer membrane (5), the supernatant of untreated mitochondria (6), or that of mitochondria treated with 5 mM atractyloside (7), 200 μM $Ca^{2+}$ (8), 1 μM cyclosporin A (9), atractyloside+CsA (10), or $Ca^{2+}$+cyclosporin A (11). In addition, the supernatant of atractyloside-treated mitochondria was sham-immunodepleted using a pre-immune serum (12), or AIF-immunodepleted in the absence (13) or presence (14) of AIF-derived immunogenic peptides (see Example 2, below) capable of blocking the AIF antiserum. Aliquots of each preparation were tested for their capacity to induce nuclear hypoploidy in isolated HeLa nuclei.

FIG. 2B shows the subcellular localization of AIF as compared to cytochrome c. 2B4.11 T cell hybridoma expressing a control vector (Neo) or human Bcl-2 were cultured for 12 hours in the absence or presence of the synthetic glucocorticoid analog dexamethasone (DEX, 1 μM), followed by immunoblot detection of AIF or cytochrome c in total cell lysates or different subcellular fractions (antibody to cytochrome c is commercially available; see Example 2 below for antibodies to AIF).

FIG. 2C shows the immunofluorescence detection of AIF in Rat-1 fibroblasts transfected with a vector control (Neo) or Bcl-2 and treated with staurosporine (Stauro, 1 μM, 2 h) or left untreated. Cells were fixed, permeabilized, and stained with an anti-AIF antibody (see Example 2) revealed by a secondary FITC-labeled conjugate. In Neo cells, staurosporine treatment leads to the generation of two phenotypes, one with partial chromatin condensation (~80% of cells, stage I), and another with more advanced chromatin condensation and nuclear fragmentation (~20% of cells, stage II), as identified by phase contrast microscopy or counter-staining with Hoechst 33342 (not shown). Arrow heads are placed in the center of the nucleus.

FIG. 2D shows the immunofluorescence detection of cytochrome c. Cytochrome c was detected by a specific monoclonal antibody revealed with a secondary PE-labeled antibody. Cells were treated and classified as in FIG. 2C.

FIG. 2E shows the nuclear morphology and $DY_m$. Live cells were stained with the DNA-intercalating dye Hoechst 33342 (blue fluorescence) or the $DY_m$-sensitive dye CMXRos (red fluorescence). Results are representative of five independent experiments.

FIG. 2F shows the immunoelectron microscopy of AIF localization in normal Jurkat T cell lymphoma cells (control) and in ceramide-treated (25 μM, 16 hours) cells manifesting mitochondrial swelling and chromatin condensation. AIF was detected using the specific antiserum revealed by a secondary Immunogold-particle (5 nm)-labeled antibody (white arrows). Representative sections of mitochondria (mito, M) or nuclei (N) near to the envelope (e) are shown.

FIG. 3A shows the effects of AIF-induced DNA loss and chromatin condensation in isolated nuclei. HeLa nuclei were cultured at 37° C. in the absence (control) or presence of 100 ng/ml recombinant AIF for 90 min, followed by staining with the DNA-intercalating dye propidium iodide (PI) and flow cytometric analysis of nuclear DNA content. Inserts demonstrate typical pictures obtained by DAPI staining.

FIG. 3B shows the electron microscopic determination of chromatin condensation of cells treated as in A and fixed with osmium tetroxide FIG. 3C shows the concentration and time dependency of AIF effects on isolated nuclei. HeLa nuclei were cultured for 90 min with the indicated concentration of rec. AIF or several AIF deletion mutants (left panel). Alternatively, nuclei were treated for different periods with the indicated dose of AIF (right panel). Nuclear hypoploidy was determined by PI staining and flow cytometry as in A.

FIG. 3D shows the pulse field gel electrophoresis of HeLa nuclei which were left untreated (lane 1) or cultured for 5 min (2), 15 min (3), 30 min (4), 60 min (5), or 90 min (6) with 100 ng/ml AIF alone, 90 min with 100 ng/ml AIFD1-377 (7), or 90 min with 100 ng AIF (8-11) in the presence of 200 μM p-chloromercuryphenylsulfonic acid (8), 200 μM of the broad spectrum caspase inhibitor, Z-VAD.fmk (9), 5 mM EDTA (10) or 5 mM EGTA (11). In addition, each nuclear preparation was assessed for the frequency of hypoploid nuclei as in A.

FIG. 3E shows the mitochondrial swelling induced by AIF. Purified rat liver mitochondria were monitored continuously for large amplitude swelling. Arrows indicate the addition of $Ca^{2+}$ (200 μM; positive control), AIF (100 ng/ml), cytosol (100 μg protein per ml), and/or Z-VAD.fmk (100 μM, pre-added to the cytosol/AIF mixture). Note that only the combined addition of AIF plus cytosol (right panel) causes mitochondrial swelling. The AIF deletion mutations (D180-638, D1-377, D563-638) were inactive in this assay.

FIG. 3F shows the AIF-induced release of cytochrome c and caspase-9 from mitochondria. Isolated mitochondria were subjected to osmotic lysis (1) or treated as in A (15 min) with buffer only (2), rec. AIF (3), cytosol (4), rec. AIF+cytosol (5), or rec. AIF+cytosol+Z-VAD.fmk (6) and their supernatants were subjected to immunoblot analysis of cytochrome c and caspase-9. Note that Z-VAD.fmk does not inhibit the release of caspase-9 but rather interferes with its proteolytic activation.

FIG. 3G shows the AIF-induced activation of a caspase. The same mitochondrial supernatants as in FIG. 3F were tested for their capacity to cleave the caspase substrate Z-VAD.afc, leading to the generation of the fluorochrome afc. The 100% value refers to the enzymatic activity obtained by osmotic lysis of mitochondria FIG. 4A shows the effect of the microinjection of AIF into cells. Buffer only or recombinant AIF (10 μM) were injected into the cytoplasm of Rat-1 cells, which were cultured for 90 min in the absence or presence of 100 μM Z-VAD.fmk (added 15 min before injection). Microinjected cells could be identified because the injectate contained FITC-dextran (green fluorescence not shown). Representative (three independent experiments, 100-200 microinjected cells per session) microphotographs of viable cells stained with the $DY_m$-sensitive dye CMXRos and Hoechst 33342 (as in FIG. 2E., upper panels) or Annexin-V, which labels surface-exposed phosphatidylserine residues (red fluorescence in lower panels).

FIG. 4B shows apoptosis induced by transfection-enforced AIF overexpression. Jurkat cells were transiently transfected with pcDNA3.1 vector only (control) or mouse AIF cDNA (under the control of a cytomegalovirus promoter, see pcDNA3.1 vector from Invitrogen). After 24 hours of culture, cells were stained with the indicated fluorochromes to determine the frequency of apoptosis-associated alterations: loss of $DY_m$ (fluorochrome: $DiOC_{(6)}$ 3), phosphatidylserine exposure (fluorochrome: Annexin V-FITC), or loss of nuclear DNA (fluorochrome: propidium iodide, PI, after ethanol permeabilization). Numbers refer to the percentage of cells bearing apoptotic characteristics. Results are representative of 3 different experiments.

FIG. 4C shows the quantitation of nuclear apoptosis induced by microinjection (minimum 100 cells, 2-3 determinations, X±SEM) of recombinant AIF, an inactive deletion mutant of AIF, cytochrome c, or atractyloside in Neo- or Bcl-2-transfected Rat-1 cells.

FIG. 4D shows the inhibition of atractyloside- and staurosporin-induced nuclear apoptosis by microinjection of an anti-AIF antiserum. Rat-1 cells were microinjected with atractyloside (ATR, 50 μM) alone, or atractyloside diluted in control serum, anti-AIF antiserum, and/or 100 μM AIF-derived immunogenic peptides. 180 min after microinjection, cells were stained with Hoechst 33342 and CMXRos (as in FIG. 4A, upper panel). Alternatively, cells were cultured for 120 min with staurosporin (1 μM, as in FIGS. 2C-2E), added to the culture medium after microinjection of control antiserum or anti-AIF. Note that atractyloside-injected and staurosporin-treated cells do not retain the $DY_m$-sensitive dye CMXRos.

DETAILED DESCRIPTION OF THE INVENTION

Both physiological cell death (apoptosis) and, in some cases, accidental cell death (necrosis) involve a two-step process. At a first level, numerous physiological and some pathological stimuli trigger an increase in mitochondrial membrane permeability. The mitochondria release apoptogenic factors through the outer membrane and dissipate the electrochemical gradient of the inner membrane. Mitochondrial permeability transition (PT) involves a dynamic multiprotein complex formed in the contact site between the inner and outer mitochondrial membranes. The PT complex can function as a sensor for stress and damage, as well as for certain signals connected to receptors. Inhibition of PT by pharmacological intervention on mitochondrial structures or mitochondrial expression of the apoptosis-inhibitory oncoprotein Bcl-2 prevents cell death, suggesting that PT is a rate-limiting event of the death process. At a second level, the consequences of mitochondrial dysfunction (collapse of the mitochondrial inner transmembrane potential, uncoupling of the respiratory chain, hyperproduction of superoxide anions, disruption of mitochondrial biogenesis, outflow of matrix calcium and glutathione, and release of soluble intermembrane proteins) entails a bioenergetic catastrophe culminating in the disruption of plasma membrane integrity (necrosis) and/or the activation of specific apoptogenic protease (caspases) by mitochondrial proteins that leak into the cytosol (cytochrome c, apoptosis-inducing factor) with secondary endonuclease activation (apoptosis). The relative rate of these two processes (bioenergetic catastrophe versus protease and endonuclease activation) determines whether a cell will undergo primary necrosis or apoptosis. The acquisition of the biochemical and ultrastructural features of apoptosis critically relies on the liberation of apoptogenic proteases or protease activators from mitochondria. The fact that mitochondrial events control cell death has major implications for the development of cytoprotective and cytotoxic drugs.

Figure 1:
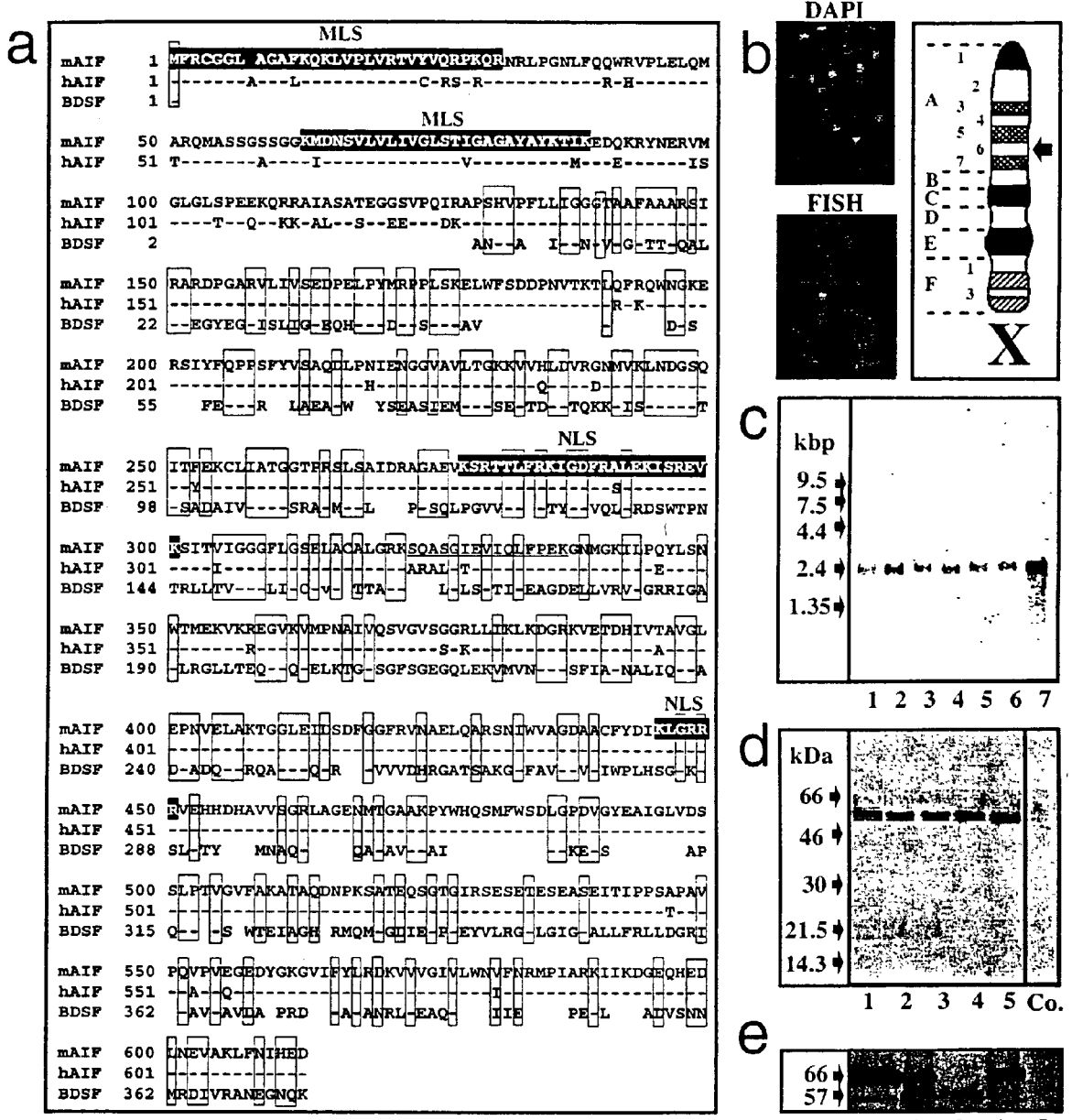
FIGS. 1A-1E shows the primary structure and tissue distribution of the AIF protein. Specifically, FIG. 1A sets forth the alignment of mouse and human AIF amino acid sequences with benzene 1,2 dioxygenase system ferredoxin NADH reductase from *Pseudomonas putida* (BDSF). The underlined sequence in mouse AIF (mAIF) matches the mass spectroscopic data obtained with trypsin-digested purified mAIF. Dashes indicate amino acid identity; lined boxes signal amino acid similarity; black boxes highlight mitochondrial localization sequences (MLS) and putative nuclear localization sequences (NLS). The GenBank accession numbers for mouse and human AIF are It232169 (AF100927) and It232173 (AF100928), respectively.

Opening of the mitochondrial permeability transition (PT) pore, which is under the control of members of the Bcl-2 family, is one of the decisive events of the apoptotic process [Kroemer, *Nature Medicine*, 3:614-620 (1997); Green et al., *Science* 281 (Aug. 28, 1998)]. PT pore opening can cause the physical disruption of the outer mitochondrial membrane [vander Heiden et al., *Cell* 91:627-637 (1997)], leading to the release of soluble proteins from the intermembrane space. The mitochondrial intermembrane fraction contains a number of different, potentially apoptogenic factors including cytochrome c [Liu et al., *Cell* 86:147-157 (1996); Kluck et al., *Science* 275:1132-1136 (1997)], pro-caspases 2, 3 and 9 [Mancini et al. *J. Cell Biol.* 140;1485-1495 (1998); Susin et al., *J. Exp. Med.*, in press], and an apoptosis-inducing factor (AIF) which suffices to force isolated nuclei to adopt an apoptotic morphology [Zamzami et al., *J. Exp. Med.* 183;1533-1544 (1996); Susin et al., *J. Exp. Med.* 184;1331-1342 (1996)]. An AIF activity which maintains its bioactivity in the presence of the caspase inhibitor Z-VAD.fmk [Susin et al., *J. Exp. Med.*, in press] was purified from the supernatant of mouse liver mitochondria subjected to PT pore-opening. Tandem mass spectrometric data acquired from tryptic digestion of a single silver-stained SDS-PAGE band [Ducret et al., *Protein Sci.* 7: 706-719 (1998)] was used to identify an expressed sequence tag (EST GenBank No. 1595214; amino acid (aa) sequence underlined in FIG. 1A), allowing the cloning of clone the corresponding full length cDNAs from mouse and man (FIG. 1A). AIF is strongly conserved between the two mammalian species (92% amino acid identity) and bears a highly significant homology with several eubacterial and archaebacterial ferredoxin or NADH oxidoreductases in its C-terminal portion (amino acid no. 128 to 613 for mAIF), which strongly suggests that AIF is conserved across all mammalian species. Its N-terminal portion has no such homology to oxidoreductases and rather bears a mitochondrial targeting sequence (boxed in FIG. 1A) [Claros et al., *Eur. J. Biochem.* 241:779-786 (1996)]. Only one mouse chromosome hybridizes with the AIF cDNA in situ (FIG. 1B). This gene is localized within mouse X chromosome region A6, which is syntenic to the human X chromosome region Xq25-26, where the human AIF gene is located (EMBL accession No. Z81364). Based on Northern blot analysis, one 2.4 kb AIF mRNA species is expressed ubiquitously in human tissue (FIG. 1C). This finding was confirmed at the protein level for mouse tissues using an antibody raised against amino acid nos. 151 to 200 of AIF, which recognizes a single ~57 kDa protein (FIG. 1D).

Figure 2:
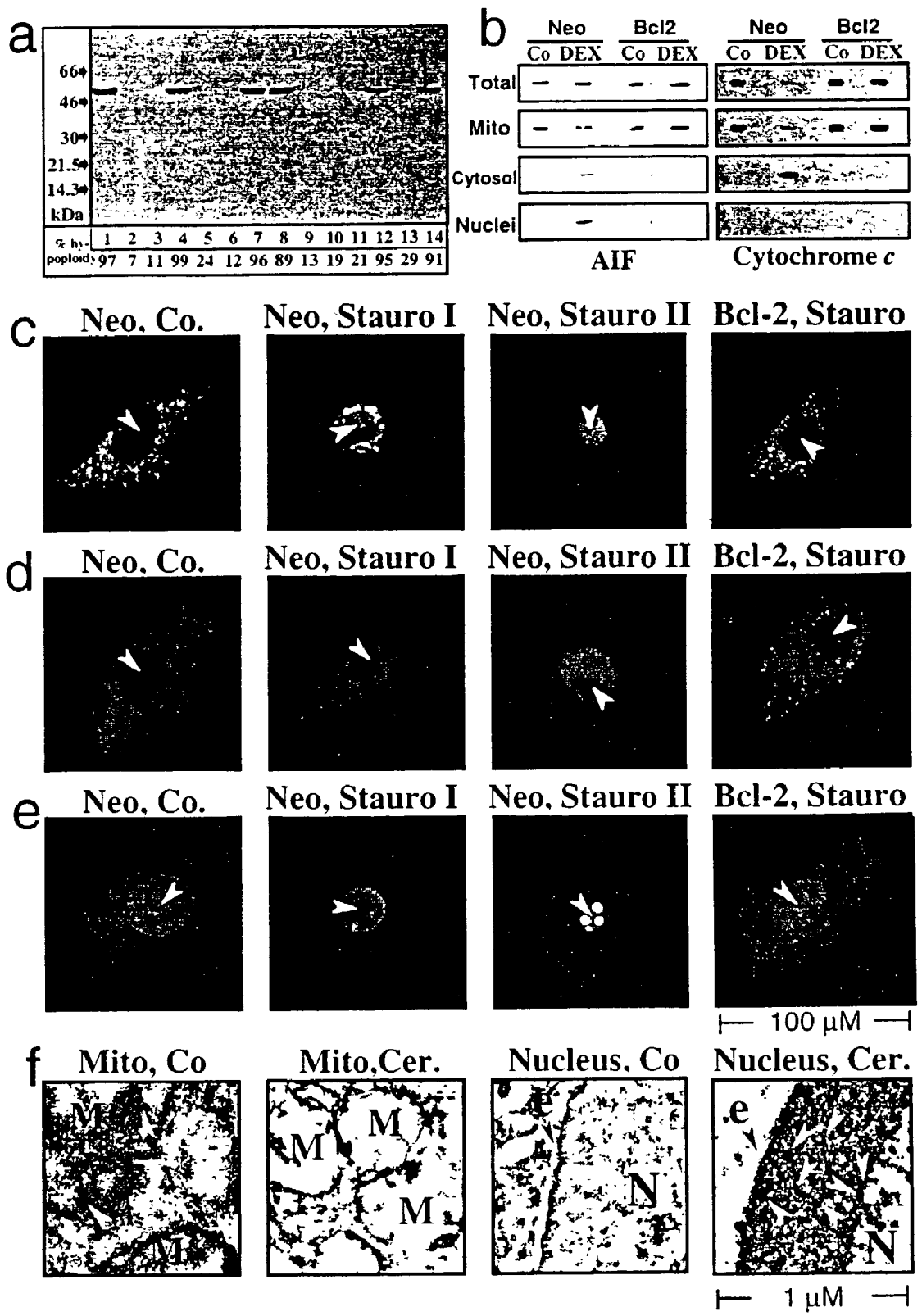
FIGS. 2A-2F show the submitochondrial and subcellular distribution of AIF in normal and apoptotic cells. Specifically.

The primary transcription/translation product of AIF cDNA obtained in vitro has an apparent molecular weight close to the expected 66.8 kDa. When imported into mitochondria in vitro, it gives rise to a shorter protein corresponding to mature AIF (FIG. 1E). The AIF bioactivity and immunoreactivity is exclusively found within the mitochondrial intermembrane space, as revealed by submitochondrial fractionation (FIG. 2A). The 57 kDa AIF protein is released upon PT pore opening by agents such as actyloside (ATR), calcium, or tert-butylhydroperoxide, and this release is prevented by the PT pore inhibitor cyclosporin A (FIG. 2A). Immunodepletion of AIF from the entire pool of mitochondrial intermembrane proteins also removes the biological activity inducing nuclear apoptosis in vitro, indicating that AIF is the principal mitochondrial factor causing nuclear apoptosis (FIG. 2A). Subcellular fractionation (FIG. 2B), immunofluorescence analysis (FIG. 2C), and immunoelectron microscopy (FIG. 2F) confirm that AIF is exclusively found in mitochondria from normal untreated cells. After induction of apoptosis by staurosporine, AIF translocates at least partially to the cytosol and to the nucleus (FIG. 2C) at the same time as the $DY_m$ is reduced and nuclei become translucid with DAPI or Hoechst 33342 staining and manifest peripheral chromatin condensation (stage I in FIGS. 2C-2E). In Rat1 cells, full release of cytochrome c from the mitochondrion to the cytosol is only visible at a subsequent stage, namely when advanced chromatin condensation and nuclear fragmentation (karyorhexis) occur (stage II in FIGS. 2C-2E) and AIF appears concentrated in the nucleus (FIG. 2C). The nuclear localization of AIF is compatible with its overall amino acid composition [Cedano et al., *J. Mol. Biol.* 266(1997)] and the presence of several putative nuclear localization signals (FIG. 1A) [Boulikas, *Crit. Rev. Eukaryotic Gene Expression* 3:193-227 (1993)]. Overexpression of Bcl-2 impedes the staurosporine-triggered mitochondrial release of AIF and cytochrome c and stabilizes the $DY_m$ (FIGS. 2C-2E), in accord with previous observations [Zamzami et al. *J. Exp. Med.* 183:1533-1544 (1996); Liu et al., *Cell* 86:147-157 (1996);

Susin et al., *J. Exp. Med.* 184:1331-1342 (1996); Kluck et al., *Science* 275:1132-1136 (1997); vander Heiden et al., *Cell* 91;627-637 (1997); Susin et al., *J. Exp. Med.*, in press; and Shimizu et al., *Proc. Natl. Acad. Sci. USA* 95:1455-1459 (1998)]. The differential relocalization of the two intermembrane proteins cytochrome c and AIF, which translocate to the cytosol and to the nucleus, respectively, has been confirmed for other cell types and in response to other apoptosis inducers, e.g. for T cell hybridoma cells treated with a glucocorticoid receptor agonist (FIG. 2B). Overexpression of Bcl-2 also prevents the mitochondrial release of AIF in this cell line (FIG. 2B). Immunelectronmicroscopy confirms the redistribution of AIF in yet another model of apoptosis, namely Jurkat lymphoma cells treated with ceramide, and reveals a particular enrichment of AIF within electron-dense areas of peripheral chromatin condensation (FIG. 2F). Altogether, these data indicate a mitochondrio-nuclear translocation of AIF during apoptosis.

When added to purified nuclei from HeLa cells, recombinant AIF protein induces DNA loss (i.e., 50 kbp gross cleavage, leading to DNA loss), as measured by flow cytometry (FIG. 3A). Moreover, AIF provokes peripheral chromatin condensation, as determined by staining with Hoechst 33342 (FIG. 3A) or by electron microscopy (FIG. 3B). These AIF effects are observed for the entire protein but not for several deletion mutations (D180-638, D1-377, D563-638) (FIG. 3C). They are likely to be independent of its putative oxidoreductase function, because recombinant AIF lacks the prosthetic FAD and NAD groups and does not reveal any oxidoreductase activity in standard enzymatic assays (not shown). The effect of AIF on isolated nuclei does not require additional cytoplasmic factors, is dose dependent, and is rapid, with effects in as little as 1 min (FIG. 3C). It is accompanied by the digestion of chromatin into ~50 kbp fragments (FIG. 3D). This large-scale DNA fragmentation is inhibited by the $Ca^{2+}$ chelator EDTA and by p-chloromercuryphenylsulfonic acid but not by the broad spectrum caspase inhibitor Z-VAD.fmk (FIG. 3D). Recombinant AIF added to purified nuclei does not cause oligonucleosomal DNA fragmentation (i.e, DNA "laddering" of 120 kbp fragments, unlike the DNA loss seen above with the 50 kbp gross fragments), nor does it cleave purified plasmid DNA (not shown). In addition to its nuclear effects, recombinant AIF acts on mitochondria. In the presence of cytosol, AIF causes purified mitochondria to undergo large amplitude swelling indicative of mitochondrial membrane permeabilization (FIG. 3E). This mitochondrial effect of AIF is accompanied by the release of cytochrome c and of caspase-9 (FIG. 3F). None of these AIF effects, either on isolated nuclei or on mitochondria, is prevented by the broad spectrum caspase inhibitor Z-VAD.fmk (FIGS. 3D-3F), suggesting that they are caspase-independent. However, the supernatant of mitochondria treated with AIF plus cytosol contains a Z-VAD.fmk-inhibitable enzymatic activity which cleaves the caspase substrate Z-VAD.fmk (FIG. 3E). This activity is at least in part due to the presence of activated caspase-9 (FIG. 3G and Susin et al., *J. Exp. Med.*, in press.). Thus, AIF may activate caspase-9 (and presumably other caspases) via an indirect, mitochondrion-dependent mechanism.

In a further series of experiments, it was determined whether the ectopic (extramitochondrial) localization of AIF would induce apoptosis in vivo. Upon microinjection of recombinant AIF into the cytoplasm of live cells, AIF rapidly (60-90 min) induces several hallmarks of apoptosis: nuclear chromatin condensation and DNA loss, dissipation of the $DY_m$, and exposure of phosphatidylserine on the outer leaflet of the plasma membrane (FIG. 4A). Transfection-enforced overexpression of wild type AIF also induces $DY_m$ collapse, phosphatidylserine exposure, and hypoploidy (FIG. 4B). None of the effects mediated by microinjected AIF is inhibited by Z-VAD.fmk (FIGS. 4A, 4C), although Z-VAD.fmk succeeds in preventing cytochrome c-induced, caspase-dependent apoptosis (FIG. 4C) [Kluck et al., *Science* 275:1132-1136 (1997); Li et al., *Cell* 91:479-489 (1997)]. Moreover, careful titration of AIF revealed no significant difference in its efficacy to induce apoptosis in control cells and in Bcl-2-transfected cells (FIG. 4C). As an internal control for its cytoprotective effect, Bcl-2 prevents the $DY_m$ loss [Zamzami et al. *J. Exp. Med.* 183:1533-1544 (1996); Susin et al., *J. Exp. Med.* 184:1331-1342 (1996); and data not shown] and the nuclear apoptosis induced by microinjection of the PT pore opening agent atractyloside (FIG. 4C). Microinjection of the AIF-specific antiserum abolishes morphological signs of atractyloside-induced nuclear apoptosis, although it does not impede the atractyloside-induced $DY_m$ dissipation (FIG. 4D). No such inhibitory effect is observed when the AIF-specific antibody is neutralized by co-injection of an excess of immunogenic peptides (see Example 2 below). The anti-AIF antiserum also has no effect on the staurosporine-induced $DY_m$ collapse, yet prevents nuclear changes induced by staurosporine (FIG. 4D), again underscoring the contribution of AIF to nuclear apoptosis.

The data reported here establish that AIF is an apoptogenic mitochondrial intermembrane protein. As cytochrome c, AIF is likely to be a phylogenetically old, bifunctional protein with an electron acceptor/donor (oxidoreductase) function and a second, independent apoptogenic function [Kluck et al. *EMBO J.* 16:4639-4649 (1997)]. Cytochrome c redistributes from the mitochondrion to the cytosol and induces nuclear apoptosis with the help of several additional factors (Apaf-1, ATP, and pro-caspase-9), which together activate caspase-3, allowing for the activation of yet another factor, DFF/CAD, which triggers oligonucleosomal DNA fragmentation [Li et al., *Cell* 91: 479-489 (1997); Liu et al., *Cell* 89:175-184 (1997); and Enari et al., *Nature* 391:43-50 (1998)]. Although DFF/ICAD has been considered as a major cytoplasmic effector responsible for nuclear apoptosis [Liu et al., *Cell* 89:175-184 (1997); and Enari et al., *Nature* 391:43-50 (1998)], it is not the sole factor which induces apoptotic chromatin condensation [Samejima et al., *J. Cell Biol.* 143:225-239 (1998)]. In strict contrast to cytochrome c, AIF has a direct effect on isolated nuclei in which it triggers chromatin condensation as well as large-scale chromatin fragmentation. This type of DNA fragmentation precedes oligonucleosomal DNA degradation in several cellular models of apoptosis [Oberhammer et al., *EMBO J.* 12:3679-3684 (1993); Lagarkova et al, *J. Biol. Chem.* 270:20239-20241 (1995)] and can be caspase-independent (FIG. 3D and ref. 22). Moreover, AIF affects the barrier function of mitochondrial membranes (FIGS. 3E, 3F), suggesting that it can engage in a self-amplification loop in which AIF released from some mitochondria acts on other mitochondria to compromise their membrane function [Susin, et al., *J. Exp. Med.* 186: 25-37 (1997)]. Bcl-2 inhibits the mitochondrial release of AIF (FIGS. 2C, 2F) but has no cytoprotective effect, once AIF is present in the cytosol (FIG. 4C). Thus, AIF is likely to act beyond or independent of the Bcl-2 and caspase checkpoints of the cell death process. Thus, AIF provides a novel molecular link between mitochondrial membrane permeabilization and apoptotic cell death.

The present invention relates to the discovery and characterization of a polypeptide, termed mitochondrial apoptisis-inducing factors (AIFs). Also disclosed are DNAs encoding mammalian AIF, which plays a critical role in induction of apoptosis.

In one aspect, the present invention is directed to the identification of materials that function as inducers of apoptosis. In particular, the invention concerns the isolation, purification and sequencing of certain nucleic acids that correspond to the mammalian AIF gene, as well as the corresponding polypeptides encoded by these nucleic acids. The invention thus comprises polynucleotides having the sequences set forth in SEQ ID NO: 1 (DNA encoding mouse AIF) and SEQ ID NO: 7 (DNA encoding human AIF), and to polynucleotides encoding AIF by way of degenerate codons, degenerate variants, conserved variants, allelic variants, and fragments thereof, all possessing an activity ascribed to AIF including, but not limited to the induction apoptosis (for example, but not limited to mouse isoform: SEQ ID NO: 4; human isoforms: SEQ ID NOS: 10 and 13). The polynucleotides and AIF polypeptides of the invention are useful in conditions related to the lack of an induction of apoptosis (e.g., various neoplastic diseases), on conditions related to the increased induction of apoptosis (e.g., various neurodegenerative diseases), as well as other maladies and dysfunctions that are related to abnormalities in apoptosis control. The invention is also directed to the polypeptides expressed by the disclosed polynucleotides, and particularly to those polypeptides set forth in SEQ ID NOS: 2 (mouse full-length), 3 (mouse mature), 8 (human full-length), and 9 (human mature), as well as to conserved variants, apoptotically active fragments (having at least one activity ascribed to AIF), cognate small molecules, isoforms of the disclosed polypeptides [e.g., mouse isoform: SEQ ID NOS: 5 and 6 (mature); a first human isoform SEQ ID NOS: 11 and 12 (mature); and a second human isoform SEQ ID NOS: 14 and 15 (mature)], and immunologically active fragments of any of the polypeptides disclosed herein (e.g., see Example 2 below).

The Apoptosis-Inducing Polypeptides (AIF)

The terms "protein," which refers to the naturally occurring polypeptide, and "polypeptide" are used herein interchangeably with respect to the AIF gene product and variants thereof. The term "mature protein" or "mature polypeptide" particularly refers to the AIF gene product with the signal sequence (or a fusion protein partner) removed.

As noted above, in specific embodiments of AIF polypeptides of the invention include those having the amino acid sequences set forth herein e.g., SEQ ID NOS: 2 (mouse), 3 (mouse mature), 8 (human), and 9 (human mature), including the AIF polypeptide modified with conservative amino acid substitutions, as well as biologically active fragments, analogs, and derivatives thereof (including the isoforms discussed above). The term "biologically active," is used herein to refer to a specific effect of the polypeptide, including but not limited to specific binding, e.g., to a binding partner, antibody, or other recognition molecule; activation of signal transduction pathways on a molecular level; and/or induction (or inhibition by antagonists) of physiological effects mediated by the native AIF polypeptide in vivo. AIF polypeptides, including fragments, analogs, and derivatives, may be prepared synthetically, e.g., using the well known techniques of solid phase or solution phase peptide synthesis. Alternatively, AIF polypeptides of the invention may be prepared using well known genetic engineering techniques, as described infra. In yet another embodiment, the AIF polypeptide may be purified, e.g., by immunoaffinity purification, from a biological fluid, such as but not limited to plasma, serum, or urine, preferably human plasma, serum, or urine, and more preferably from a subject who overexpresses the polypeptide, such as an individual suffering from for example a variety of neurodegenerative diseases.

Fragments of the AIF Polypeptide

In a particular embodiment, the present invention contemplates that naturally occurring fragments of the AIF polypeptide may be important. The peptide sequence includes a number of sites that are frequently the target for proteolytic cleavage, e.g., arginine residues. It is possible that the full length polypeptide may be cleaved at one or more such sites to form biologically active fragments (which would necessarily include those portions of the polypeptide that would allow the fragment to remain active). Such biologically active fragments may either agonize or antagonize the functional activity of the AIF polypeptide to either induce or prevent induction of apoptosis, respectively.

Figure 3:
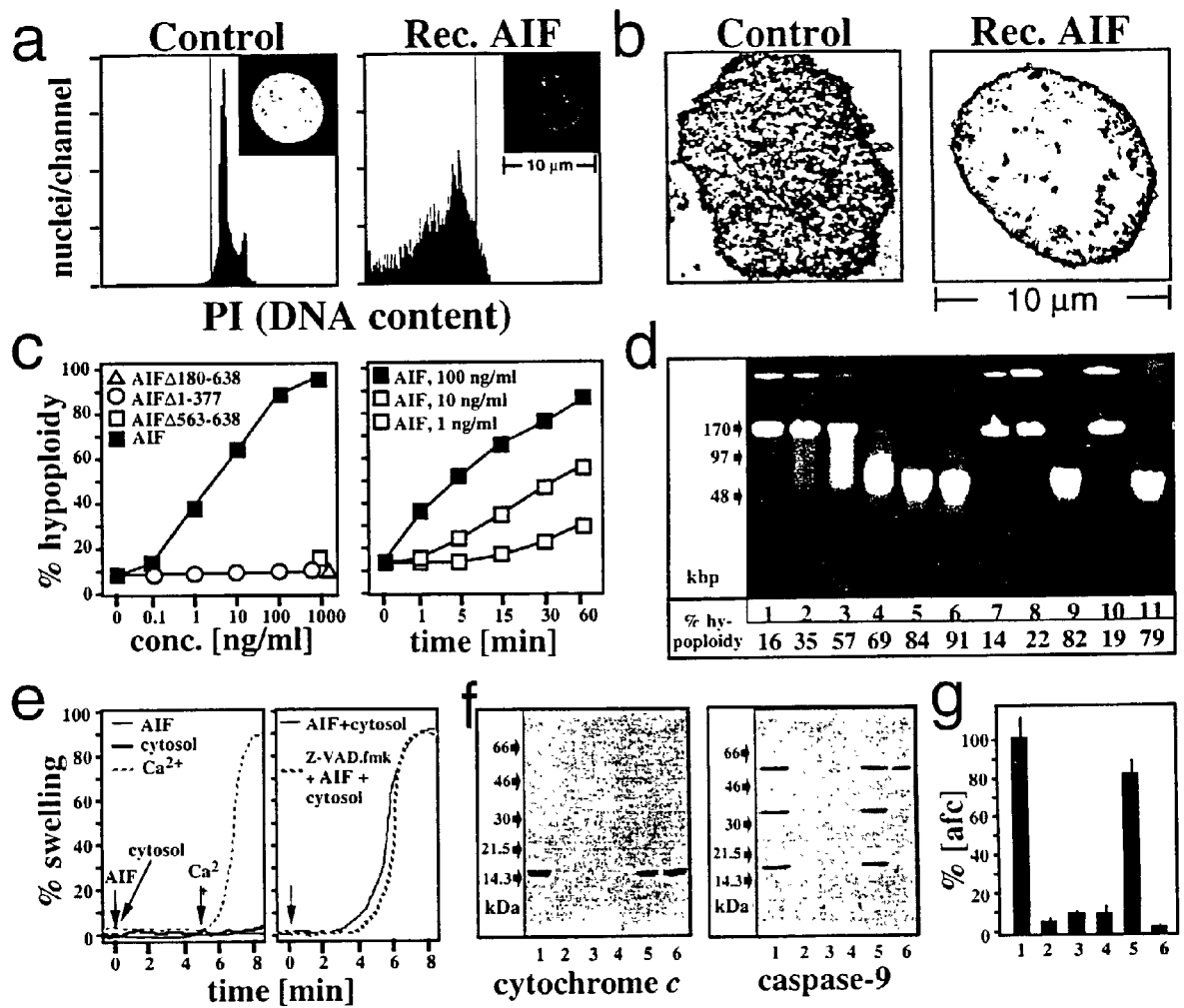
FIGS. 3A-3G show the effects of AIF on isolated nuclei and mitochondria. Specifically.
Figure 4:
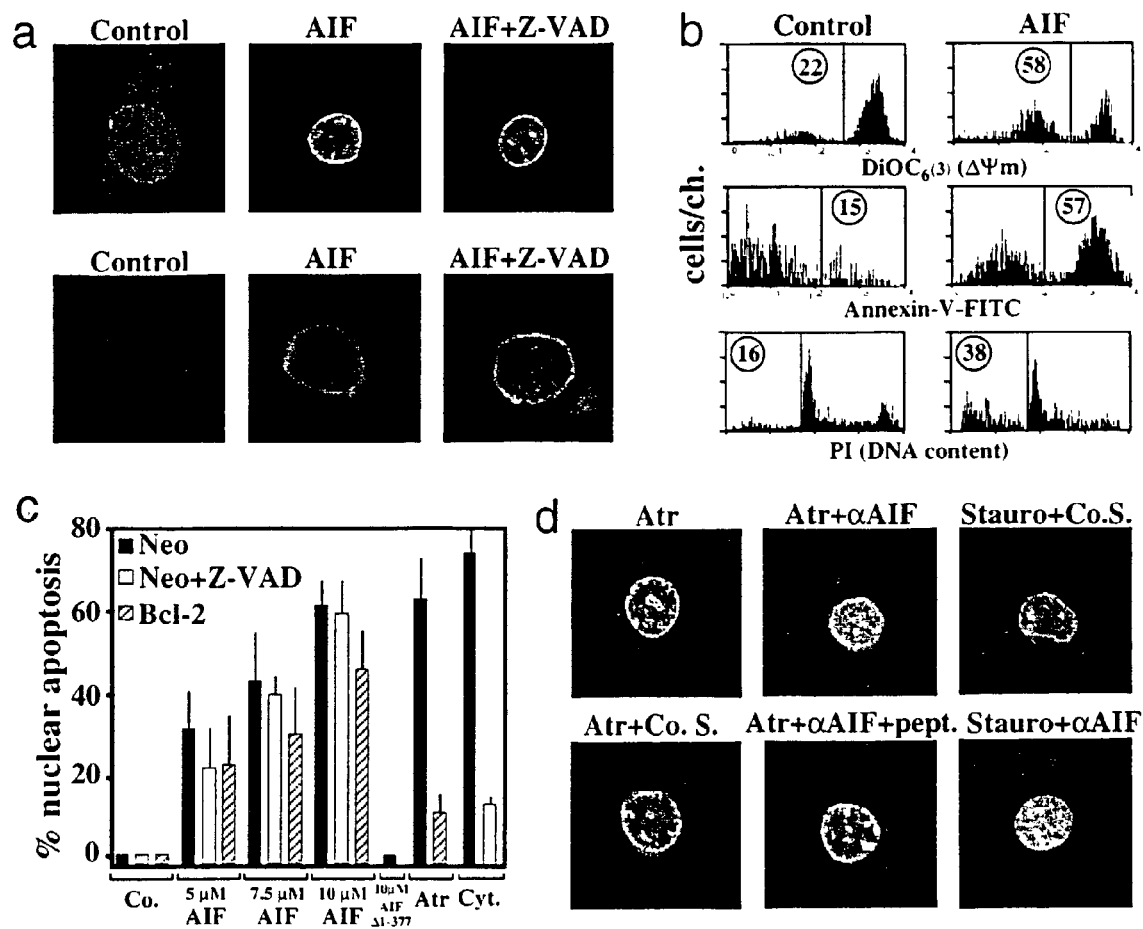
FIGS. 4A-4D show the effects of AIF on intact cells. Specifically.

As described herein, certain regions of the AIF molecule which are important for one or more of the activities of AIF have been identified and thus this information provides a person of ordinary skill in the art guidance to the design of fragments, analogs, and derivatives, which are useful to the practice of the invention [see below for AIF deletion mutants BamH1 (D180-638), NcoI (D1-377), or HindIII (D563-638) as well as FIGS. 3 and 4 for data involving the foregoing mutants].

Analogs of the AIF Polypeptide

The present invention specifically contemplates preparation of analogs of the AIF polypeptide, which are characterized by being capable of a biological activity of the AIF polypeptide, e.g., of binding to a specific binding partner of the AIF polypeptide (e.g., an enzyme or like effectors. In one embodiment, the analog agonizes AIF activity, i.e., it functions similarly to the AIF polypeptide. Preferably, an AIF agonist is more effective than the native protein. For example, an AIF agonist analog may bind to the specific AIF binding partner with higher affinity, or demonstrate a longer half-life in vivo, or both. Nevertheless, AIF polypeptide agonist analogs that are less effective than the native protein are also contemplated.

In another embodiment, the analog antagonizes AIF activity. For example, an AIF analog that binds to a specific AIF binding partner but does not induce signal transduction can competitively inhibit binding of native AIF to its binding partner, thus decreasing AIF activity in vivo. Such an AIF antagonist analog may also demonstrate different properties from the AIF polypeptide, e.g., longer (or shorter) half-life in vivo, greater (or lesser) binding affinity for the specific AIF binding partner, or both.

In one embodiment, an analog of the AIF polypeptide is an AIF polypeptide modified by substitution of amino acids at positions on the polypeptide that are not essential for structure or function. For example, substitution of divergent amino acid residues in the human sequence as compared to the murine amino acid sequence (and vice versa) will likely yield useful analogs of the AIF polypeptide (i.e., amino acid swaps between mouse and human). For example, aligning the mature mouse AIF amino acid sequence (SEQ ID NO.: 3) with the mature human AIF amino acid sequence (SEQ ID NO.: 9), beginning at position 1 (one), reveals amino acid differences at the following positions: 9, 10, 11, 12, 13, 14, 15, 16, 17, 18, 19, 20, 21, 22, 23, 24, 25, 27, 28, 29, 30, 31, 32, 33, 34, 35, 36, 37, 38, 39, 41, 42, 43, 44, 45, 46, 47, 48, 49, 50, 51, 52, 53, 54, 55, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 108, 109, 110, 111, 112, 113, 115, 116, 117, 118, 119, 121, 122, 123, 124, 125, 126, 127, 128, 129, 130, 131, 132, 133, 134, 136, 137, 140, 141, 143, 144, 147, 148, 149, 150, 151, 152, 153, 154, 155, 156, 157, 158, 159, 160, 161, 162, 163, 164, 165, 166, 167, 168, 169, 170, 171, 172, 174, 175, 176, 177, 178, 179, 180, 181, 182, 184, 185, 186, 187, 188, 189, 190, 191, 192, 193, 194, 195, 196, 197, 198, 199, 200, 201, 202, 203, 204, 205, 206, 208, 209, 210, 211, 212, 213, 214, 215, 216, 217, 218, 219, 220, 221, 222, 224, 225, 226, 227, 228, 229, 230, 232, 234, 235, 236, 237, 238, 239, 240, 241, 242, 243, 244, 245, 246, 247, 248, 249, 250, 251, 252, 253, 254, 255, 256, 257, 258, 259, 260, 262, 263, 264, 265, 266, 267, 268, 269, 270, 271, 272, 273, 274, 275, 276, 277, 278, 279, 280, 282, 283, 284, 285, 286, 287, 288, 289, 290, 291, 292, 293, 294, 295, 296, 297, 298, 299, 300, 301, 302, 303, 304, 306, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 358, 359, 360, 361, 362, 363, 364, 365, 366, 367, 368, 369, 370, 371, 372, 373, 374, 375, 376, 377, 378, 380, 381, 382, 383, 384, 385, 386, 387, 388, 389, 390, 391, 392, 393, 394, 395, 397, 398, 399, 400, 401, 402, 403, 404, 405, 406, 407, 408, 409, 411, 412, 413, 414, 415, 416, 417, 418, 420, 421, 422, 423, 424, 425, 426, 427, 428, 429, 430, 431, 432, 433, 434, 435, 436, 437, 438, 440, 441, 442, 443, 444, 445, 446, 447, 448, 451, 452, 453, 455, 456, 457, 458, 460, 461, 462, 463, 464, 465, 466, 467, 468, 469, 470, 471, 473, 474, 475, 476, 477, 478, 479, 480, 481, 482, 483, 484, 485, 486, 487, 488, 489, 490, 491, 492, 493, 494, 495, 496, 497, 498, 499, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 545, 546, 547, 548, 549, 550, 551, 552, 553, 554, 555, 556, 557, 558, 559, 560, 561, 562, 563, 564, 565, 566, 567, 568, 569, 570, 571, 574, 575, 576, 577, 578, 579, 580, 581, 582, 583, 584, 585, 586, 587, 588, 589, 590, 592, 593, 594, 595, 596, 597, 598, 599, 600, 601, 602, 603, 604, 605, 606, 607, 608, 609, 610, 611, and 612.

Also contemplated are conservative amino acid substitutions between the mouse and human AIF polypeptides as determined by certain chemical or physical features shared in common between the species, charge hydrophobicity, and/or acidic amino acids versus basic amino acids.

Analogs, such as fragments, may be produced, for example, by pepsin digestion of the AIF polypeptide. Other analogs, such as muteins, may be produced by standard site-directed mutagenesis of the AIF polypeptide coding sequences. Analogs exhibiting apoptosis-inducing activity such as small molecules, whether functioning as promoters or inhibitors, may be identified by known a variety of in vitro assays described herein and others that are well known in the art.

Small Molecule Analogs and Peptidomimetics of AIF Polypeptide

The structure of the AIF polypeptide, is analyzed by various methods known in the art. The protein sequence may be characterized by a hydrophilicity analysis [e.g., Hopp et al., *Proc. Natl. Acad. Sci. USA,* 78:3824 (1981)]. A hydrophilicity profile is used to identify the hydrophobic and hydrophilic regions of the AIF polypeptide, which may indicate regions buried in the interior of the folded polypeptide, and regions accessible on the exterior of the polypeptide. In addition, secondary structural analysis [e.g., Chou et al., *Biochem.,* 13:222 (1974)] may also be undertaken, to identify regions of AIF polypeptide that assume specific secondary structures. Manipulation of the predicted or determined structure, including secondary structure prediction, may be accomplished using computer software programs readily available in the art.

By providing an abundant source of recombinant AIF polypeptide, the present invention enables quantitative structural determination of the polypeptide. In particular, enough material is provided for nuclear magnetic resonance (NMR), infrared (IR), Raman, and ultraviolet (UV), and circular dichroism (CD), spectroscopic analysis. In particular NMR provides very powerful structural analysis of molecules in solution, which more closely approximates their native environment [Marion et al., *Biochem. Biophys. Res. Comm.,* 113:967-974 (1983); Bar et al., *J. Magn. Reson.,* 65:355-360 (1985); Kimura et al., *Proc. Natl. Acad. Sci. USA,* 77:1681-1685 (1980)]. Other methods of structural analysis can also be employed. These include but are not limited to X-ray crystallography [Engstom, *Biochem. Exp. Biol.,* 11:7-13 (1974)].

In yet a further embodiment, an analog AIF polypeptide may be tested to determine whether it cross-reacts with an antibody specific for the native AIF polypeptide or specific fragments thereof. The degree of cross-reactivity provides information about structural homology or similarity of proteins, or about the accessibility of regions corresponding to portions of the polypeptide that were used to generate fragment-specific antibodies.

Screening for AIF Analogs

Various screening techniques are known in the art for the screening of analogs of polypeptides. Various libraries of chemicals are available. Accordingly, the present invention contemplates screening such libraries, e.g., libraries of synthetic compounds generated over years of research, libraries of natural compounds, and combinatorial libraries, as described in greater detail, infra, for analogs of the AIF polypeptide. In one embodiment, the invention contemplates screening such libraries for compounds that bind to anti-AIF polypeptide antibodies. In another aspect, once the AIF binding partner is identified (see infra), any screening technique known in the art may be used to screen for AIF binding partner agonists or antagonists. The present invention contemplates screens for small molecule ligands or ligand analogs and mimics, as well as screens for natural ligands that bind to and agonize or antagonize activate the AIF binding partner in vivo.

Knowledge of the primary sequence of the AIF binding partner, and the similarity of that sequence with proteins of known function, may provide an initial clue as to the agonists or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott et al., *Science,* 249:386-390 (1990); Cwirla et al., *Proc. Natl. Acad. Sci. USA,* 87:6378-6382 (1990); Devlin et al., *Science,* 249:404-406 (1990)], very large libraries can be constructed ($10^6$-$10^8$ chemical entities). A second approach uses primarily chemical methods, of which the Geysen method [Geysen et al., *Molecular Immunology,* 23:709-715 (1986); Geysen et al., *J. Immunologic Method,* 102:259-274 (1987)] and the recent method of Fodor et al., *Science,* 251:767-773 (1991) are examples. Furka et al. 14th International Congress of Biochemistry, Volume 5, Abstract FR:013 (1988); Furka, *Int. J. Peptide Protein Res.,* 37:487-493 (1991); Houghton (U.S. Pat. No. 4,631,211, issued December 1986); and Rutter et al. (U.S. Pat. No. 5,010,175, issued Apr. 23, 1991) describe methods to produce a mixture of peptides that may be tested as agonists or antagonists. In another aspect, synthetic libraries [Needels et al., *Proc. Natl. Acad. Sci. USA,* 90:10700-10704 (1993); Lam et al., International Patent Publication No. WO 92/00252, each of which is incorporated herein by reference in its entirety], and the like may be used to screen for AIF binding partner ligands according to the present invention. With such libraries, binding partner antagonists may be detected using cells that express the binding partner(s) without actually cloning the AIF binding partner.

In still another aspect, analogs of the AIF polypeptide may be screened for by use of a combinatorial chemistry system as disclosed in U.S. Pat. No. 5,723,232 to Kauffman and Ballivet.

Derivatives of AIF Polypeptides

The polypeptides disclosed herein may be derivatized by the attachment of one or more chemical moieties to the protein moiety. The chemically modified derivatives may be further formulated for intraarterial, intraperitoneal, intramuscular, subcutaneous, intravenous, oral, nasal, rectal, buccal, sublingual, pulmonary, topical, transdermal, or other routes of administration. Chemical modification of biologically active proteins has been found to provide additional advantages under certain circumstances, such as increasing the stability and circulation time of the therapeutic protein and decreasing immunogenicity [U.S. Pat. No. 4,179,337; Abuchowski et al., "Soluble Polymer-Enzyme Adducts", in *Enzymes as Drugs*, pp. 367-383, Holcenberg and Roberts, eds., Wiley-Interscience, New York, N.Y., (1981); Francis, *Focus on Growth Factors*, 3:4-10 (1992)].

Chemical Moieties For Derivatization

The chemical moieties suitable for derivatization may be selected from among water soluble polymers. The polymer selected should be water soluble so that the protein to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/polypeptide conjugate will be used therapeutically, and if so, the desired dosage, circulation time, resistance to proteolysis, and other considerations. For the present proteins and polypeptides, these may be ascertained using the assays provided herein.

Polymer Molecules

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols and polyvinyl alcohol. Polyethylene glycol propionaldenhyde may provide advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Polymer/Protein Ratio

The number of polymer molecules so attached may vary, and one skilled in the art will be able to ascertain the effect on function. One may mono-derivatize, or may provide for a di-, tri- tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

Attachment of the Chemical Moiety to the Protein

The polyethylene glycol molecules (or other chemical moieties) should be attached to the protein with consideration of effects on functional or antigenic domains of the protein. There are a number of attachment methods available to those skilled in the art e.g., EP 0 401 384 (coupling PEG to G-CSF); Malik et al., *Exp. Hematol.*, 20:1028-1035 (1992) (reporting pegylation of GM-CSF using tresyl chloride). For example, polyethylene glycol may be covalently bound through amino acid residues via a reactive group, such as a free amino or carboxyl group. Reactive groups are those to which an activated polyethylene glycol molecule may be bound. The amino acid residues having a free amino group may include lysine residues and the N-terminal amino acid residues, those having a free carboxyl group may include aspartic acid residues glutamic acid residues and the C-terminal amino acid residue. Sulfhydry groups may also be used as a reactive group for attaching the polyethylene glycol molecule(s). Preferred for therapeutic purposes is attachment at an amino group, such as attachment at the N-terminus or lysine group. Attachment at residues important for receptor binding should be avoided if receptor binding is desired.

N-terminally Chemically Modified Proteins

One may specifically desire N-terminally chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the $pK_a$ differences between the $\in$-amino groups of the lysine residues and that of the α-amino group of the N-terminal residue of the protein. By such selective derivatization attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

Nucleic Acids Associated With AIF Polypeptides

As noted above, the present invention is directed to DNAs encoding the AIF polypeptides as well as DNAs that hybridize to the DNAs that encode the AIF polypeptides (see below for stringency conditions). Thus, in accordance with the present invention there may be employed conventional molecular biology, microbiology, and recombinant DNA techniques within the skill of the art. Such techniques are explained fully in the scientific literature [e.g., Sambrook et al., *Molecular Cloizing: A Laboratory Manual*, Second Edition, Cold Spring Harbor Laboratory Press, Cold Spring Harbor, N.Y. (1989); Glover ed., *DNA Cloning: A Practical Approach*, Volumes I and II, MRL Press, Ltd., Oxford, U.K. (1985); Gait ed., Oligonucleotide Synthesis, Oxford University Press (1984); Hames et al., eds., *Nucleic Acid Hybridization*, Springer-Verlag (1985); Hames et al., eds. *Transcription And Translation*, Oxford University Press (1984)]; Freshney ed., *Animal Cell Culture*, Oxford University Press (1986); *Immobilized Cells And Enzymes*, IRL Press (1986)]; Perbal, *A Practical Guide To Molecular Cloning*, Wiley, New York (1984)]. Of particular relevance to the present invention are strategies for isolating, cloning, sequencing, analyzing, and characterizing a gene or nucleic acid based on the well known polymerase chain reaction (PCR) techniques.

For the purposes of this disclosure, the following definitions are relevant. A "replicon" is any genetic element (e.g., plasmid, chromosome, virus) that functions as an autonomous unit of DNA replication in vivo, i.e., capable of replication under its own control.

A "vector" is a replicon, such as a plasmid, phage or cosmid, to which another DNA segment may be attached so as to bring about the replication of the attached segment.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

"Heterologous" DNA refers to DNA not naturally located in the cell, or in a chromosomal site of the cell. Preferably, the heterologous DNA includes a gene foreign to the cell.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

A "clone" is a population of cells derived from a single cell or common ancestor by mitosis.

A "polynucleotide" refers single strand DNA, RNA, or modified DNA or RNA. This term also includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single-stranded form of the nucleic acid molecule can anneal to the other nucleic acid molecule under the appropriate conditions of temperature and solution ionic strength (Sambrook et al., 1989, supra). The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (Sambrook et al., 1989, supra, 9.50-0.51). For hybridization with shorter nucleic acids, i.e., oligonucleotides, the position of mismatches becomes more important, and the length of the oligonucleotide determines its specificity (Sambrook et al., 1989, supra, 11.7-11.8). Preferably a minimum length for a hybridizable nucleic acid is at least about 10 nucleotides; more preferably at least about 15 nucleotides; most preferably the length is at least about 20 nucleotides.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Isolation of AIF Coding and Flanking Sequences

As used herein, the term mammalian "AIF" (apoptosis-inducing factor) when used to describe a nucleic acid molecule refers to a nucleic acid molecule or fragment thereof that (a) has the nucleotide sequence as set forth in SEQ ID NO.:1 (murine), SEQ ID NO.:4 (murine isoform), SEQ ID NO.: 7 (human), SEQ ID NO.: 10 (human isoform), and SEQ ID NO.: 13 (human isoform); (b) has a nucleic acid sequence encoding a polypeptide that is at least 75 percent identical, but may be greater than 75 percent, i.e., 80 percent, 85 percent, 90 percent, 95 percent, or even greater than 95 percent identical, to the polypeptide encoded by any of SEQ ID NO.:1 (murine), SEQ ID NO.:4 (murine isoform), SEQ ID NO.: 7 (human), SEQ ID NO.: 10 (human isoform), and SEQ ID NO.: 13 (human isoform); (c) is a naturally occurring allelic variant of (a) or (b); (d) is a nucleic acid variant of (a)-(c) produced as provided for herein; (e) has a sequence that is complementary to (a)-(d); and/or (f) hybridizes to any of (a)-(e) under high stringency conditions. The term "high stringency conditions" refers to hybridization and washing under conditions that permit only binding of a nucleic acid molecule such as an oligonucleotide or cDNA molecule probe to highly homologous sequences. Exemplary stringent hybridization conditions are as follows: hybridization at 65° C. in 3×SSC, 20 mm $NaPO_4$, pH 6.8 followed by washing at 55° C.-65° C. and washing 0.015 M NaCl, 0.005 M NaCitrate, and 0.1 percent SDS. It is understood by those of skill in the art that variation in these conditions occurs based on the length and GC nucleotide content of the sequences to be hybridized. Formulas standard in the art are available for determining exact hybridization conditions. See Sambrook et al., supra. For example, another stringent wash solution is 0.2×SSC and 0.1 percent SDS used at a temperature of between 50° C.-65° C. Where oligonucleotide probes are used to screen cDNA or genomic libraries, the following stringent washing conditions may be used. One protocol uses 6×SSC with 0.05 percent sodium pyrophosphate at a temperature of 35° C.-62° C., depending on the length of the oligonucleotide probe. For example, 14 base pair probes are washed at 35° C.-40° C., 17 base pair probes are washed at 45° C.-50° C., 20 base pair probes are washed at 52° C.-57° C., and 23 base pair probes are washed at 57° C.-63° C. The temperature can be increased 2-3° C. where the background non-specific binding appears high. A second protocol utilizes tetramethylammonium chloride (TMAC) for washing oligonucleotide probes. One stringent washing solution is 3 M TMAC, 50 mm Tris-HCl, pH 8.0, and 0.2 percent SDS. The washing temperature using this solution is a function of the length of the probe. For example, a 17 base pair probe is washed at about 45-50° C. Mammalian AIF encoding nucleic acids also includes nucleic acid sequences that encode mammalian AIF polypeptide or a fragment thereof, by the way of degenerate codons.

Percent sequence identity can be determined by standard methods that are commonly used to compare the similarity in position of the amino acids of two polypeptides. By way of example, using a computer program such as BLAST or FASTA, the two polypeptides for which the percent sequence identity is to be determined are aligned for optimal matching of their respective amino acids (the "matched span", which can include the full length of one or both sequences, or a predetermined portion of one or both sequences). Each computer program provides a "default" opening penalty and a "default" gap penalty, and a scoring matrix such as PAM 250. A standard scoring matrix (see Dayhoff et al., Atlas of Protein Sequence and Structure, vol. 5, supp.3 (1978)), can be used in conjunction with the computer program. The percent identity can then be calculated using an algorithm contained in a program such as FASTA as:

$$\frac{\text{Total number of identical matches}}{[\text{length of the longer sequence within the matched span}] + [\text{number of gaps introduced into the longer sequence in order to align the two sequences}]} \times 100$$

Polypeptides that are at least 70 percent identical will typically have one or more amino acid substitutions, deletions, and/or insertions as compared with wild type AIF. Usually, the substitutions will be conservative so as to have little or no effect on the overall net charge, polarity, or hydrophobicity of the protein but optionally may increase the activity of AIF. Exemplary conservative substitutions are set forth in Table I below.

TABLE I

Conservative amino acid substitutions

Basic: arginine, lysine, histidine
Acidic: glutamic acid, aspartic acid
Polar: glutamine, asparagine
Hydrophobic: leucine, isoleucine, valine
Aromatic: phenylalanine, tryptophan, tyrosine
Small: glycine, alanine, serine. threonine, methionine Other variants of the polypeptide may be prepared by aligning a human AIF polypeptide sequence with a murine AIF polypeptide sequence (or AIF from other species) and identifying the divergent amino acids. One or more of the divergent amino acids can then be substituted with the diverging amino acid or with other amino acids. Such variants may therefore be a composite polypeptide comprising amino acid sequences derived from AIF polypeptides, which are derived from two or more species.

The nucleic acids contemplated by the present invention extend as indicated, to other nucleic acids that code on expression for peptides such as those set forth in SEQ ID NOS: 2 (mouse full length), 3 (mouse mature), 8 (human full length), 9 (human mature), as well as any isoforms [murine isoform: SEQ ID NO.: 5 (full length), SEQ ID NO.: 6 (full length); human isoforms: SEQ ID NO.: 11 (full length), SEQ ID NO.: 12 (mature), and SEQ ID NO.: 14 (full length), SEQ ID NO.: 15 (mature)] of the foregoing polypeptides. Accordingly, while AIF-encoding DNAs have been isolated and sequenced due to the demonstrated homologies, any animal cell potentially can serve as the nucleic acid source for the molecular cloning of a polynucleotide encoding the peptides of the invention. The DNA may be obtained by standard procedures known in the art from cloned DNA (e.g., a DNA "library"), by chemical synthesis, by cDNA cloning, or by the cloning of genomic DNA, or fragments thereof, purified from the desired cell [Sambrook et al., 1989, supra; Glover, 1985, supra]. Clones derived from genomic DNA may contain regulatory and intronic DNA regions in addition to coding regions: clones derived from cDNA will not contain intron sequences. Whatever the source, the gene should be molecularly cloned into a suitable vector for propagation of the gene.

In the molecular cloning of the gene from genomic DNA, the genomic DNA can be amplified using primers selected from the cDNA sequences. Alternatively, DNA fragments are generated, some of which will encode the desired gene. The DNA may be cleaved at specific sites using various restriction enzymes. One may also use DNase in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired AIF or AIF-like gene may be accomplished in a number of ways. For example, if an amount of a portion of a AIF or AIF-like gene or its specific RNA, or a fragment thereof, is available and can be purified and labeled, the generated DNA fragments may be screened by nucleic acid hybridization to a labeled probe [Benton et al., Science, 196:180 (1977); Grunstein et al., Proc. Natl. Acad. Sci. USA, 72:3961 (1975)]. The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted SEQ ID NOS: 1 and 7, as well as DNA (as disclosed herein) encoding isoforms of the present AIF polypeptides. Preferably, a fragment is selected that is highly unique to the AIF polypeptides of the invention. Those DNA fragments with substantial homology to the probe will hybridize. As noted above, the greater the degree of homology, the more stringent the hybridization conditions that can be used. In one embodiment, low stringency hybridization conditions are used to identify a homologous AIF peptide. However, in a preferred aspect, and as demonstrated experimentally herein, a nucleic acid encoding an AIF peptide of the invention will hybridize to a nucleic acid having a nucleotide sequence such as depicted in SEQ ID NOS: 1 and 7, as well as DNA (as disclosed herein) encoding isoforms of the present AIF polypeptides or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, tyrosine phosphatase activity or antigenic properties as known for the present AIF polypeptides. For example, the antibodies of the instant invention can conveniently be used to screen for homologs of the AIF polypeptides from other sources.

A gene encoding an AIF polypeptide of the invention can also be identified by mRNA selection, i.e., by nucleic acid hybridization followed by in vitro translation. In this procedure, fragments are used to isolate complementary mRNAs by hybridization. Such DNA fragments may represent available, purified modulator DNA. Immunoprecipitation analysis or functional assays (e.g., tyrosine phosphatase activity) of the in vitro translation products of the products of the isolated mRNAs identifies the mRNA and, therefore, the complementary DNA fragments, that contain the desired sequences. In addition, specific mRNAs maybe selected by adsorption of polysomes isolated from cells to immobilized antibodies specifically directed against an AIF polypeptide.

A radiolabeled AIF polypeptide cDNA can be synthesized using the selected mRNA (from the adsorbed polysomes) as a template. The radiolabeled mRNA or cDNA may then be used as a probe to identify homologous AIF polypeptide DNA fragments from among other genomic DNA fragments.

As mentioned above, a DNA sequence encoding AIF peptides as disclosed herein can be prepared synthetically rather than cloned. The DNA sequence can be designed with the appropriate codons for the AIF polypeptide amino acid sequences. In general, one will select preferred codons for the intended host if the sequence will be used for expression. The complete sequence is assembled from overlapping oligonucleotides prepared by standard methods and assembled into a complete coding sequence [e.g., Edge, *Nature*, 292:756 (1981); Nambair et al., *Science*, 223:1299 (1984); Jay et al., *J. Biol. Chem.*, 259:6311 (1984)]

Synthetic DNA sequences allow convenient construction of genes which will express AIF analogs, as described above. Alternatively, DNA encoding analogs can be made by site-directed mutagenesis of native AIF genes or cDNAs, and analogs can be made directly using conventional polypeptide synthesis.

A general method for site-specific incorporation of non-natural occurring amino acids into proteins is described in Noren et al, *Science*, 244:182-188 (1989). This method may be used to create analogs of the AIF polypeptide with unnatural amino acids.

Non-coding Nucleic Acids

The present invention extends to the preparation of antisense nucleotides and ribozymes that may be used to interfere with the expression of the AIF proteins at the translational level. This approach involves antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [Weintraub, *Sci. Am.*, 262:40-46 (1990); Marcus-Sekura, *Anal. Biochem.*, 172:289-295 (1988)]. In the cell, they hybridize to that mRNA, forming an untranslatable double-stranded molecule. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into AIF peptide-producing cells. Antisense methods have been used to inhibit the expression of many genes in vitro [(Marcus-Sekura, 1988 supra; Hambor et al., *J. Exp. Med.*, 168:1237-1245 (1988)].

Ribozymes are RNA molecules possessing the ability to specifically cleave other single-stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it [Cech, *J. Am. Med. Assoc.*, 260:3030-3034 (1988)]. Because they are sequence-specific, only mRNAs with particular sequences are inactivated.

Investigators have identified two types of ribozymes, *Tetrahymena*-type and "hammerhead"-type. *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species, and eighteen base recognition sequences are preferable to shorter recognition sequences.

The DNA sequences described herein may thus be used to prepare antisense molecules against and ribozymes that cleave mRNAs for AIF polypeptides and their ligands, thus inhibiting expression of the AIF gene, and leading to a decreased induction of apoptosis.

In another embodiment, short oligonucleotides complementary to the coding and complementary strands of the AIF nucleic acid, or to non-coding regions of the AIF gene 5', 3', or internal (intronic) to the coding region are provided by the present invention. Such nucleic acids are useful as probes, either as directly labeled oligonucleotide probes, or as primers for the polymerase chain reaction, for evaluating the presence of mutations in the AIF gene, or the level of expression of AIF mRNA. In a specific embodiment, the non-coding nucleic acids provide for homologous recombination for integration of an amplifiable gene and/or other regulatory sequences in proximity to the AIF gene, e.g., to provide for higher levels of expression of the AIF polypeptide, or to overcome a mutation in the AIF gene regulatory sequences that prevent proper levels of expression of the AIF polypeptide (International Patent Publication WO 91/06666, by Skoultchi; International Patent Publication No. WO 91/09955, published Jul. 11, 1991 by Chappel; International Patent Publication No. WO 90/14092, by Kucherlapati and Campbell).

Production of AIF Polypeptides: Expression and Synthesis

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

For the purposes of this disclosure, the following definitions are relevant. A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is also used herein to refer to this sort of signal sequence. Translocation signal sequences can be found associated with a variety of proteins native to eukaryotes and prokaryotes, and are often functional in both types of organisms.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted upstream (5') of and in reading frame with the gene.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9, pUC or pUC plasmid derivatives, e.g., pGEX vectors, pET vectors, pmal-c, pFLAG, etc., and their derivatives, plasmids such as RP4; phage DNAs, e.g., the numerous derivatives of phage λ, e.g., NM989, and other phage DNA, e.g., M13 and filamentous single-stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. Also the expression of AIF may achieved in methylotrophic yeast, e.g., *Pichia pastoris* yeast (e.g., International Patent Publication No. WO 90/03431, by Brierley et al.; International Patent Publication No. WO 90/10697, by Siegel et al.).

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the AOX 1 promoter of methylotrophic yeast, the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*; fungi such as yeasts (*Saccharomyces*, and methylotrophic yeast such as *Pichia, Candida, Hansenula,* and *Torulopsis*); and animal cells, such as CHO, R1.1, B-W and LM cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors, a person skilled in the art will be able to construct a variety of vector/expression control sequence/host combinations that will express the DNA sequences of this invention on fermentation or in large scale animal culture.

In a specific embodiment, an AIF fusion protein can be expressed. An AIF fusion protein comprises at least a functionally active portion of a non-AIF protein joined via a peptide bond to at least a functionally active portion of an AIF polypeptide. The non-AIF sequences can be amino- or carboxy-terminal to the AIF sequences. Further, for stable expression of a proteolytically inactive AIF fusion protein, the portion of the non-AIF fusion protein is joined via a peptide bond to the amino-terminus of the AIF protein. A recombinant DNA molecule encoding such a fusion protein comprises a sequence encoding at least a functionally active portion of a non-AIF protein joined in-frame to the AIF coding sequence, and preferably encodes a cleavage site for a specific protease, e.g., thrombin or Factor Xa, preferably at the AIF-non-AIF juncture.

With respect to AIF fusion proteins, a further aspect includes fusion of the AIF polypeptide or biologically active fragment thereof with antibodies or antibody fragments (e.g., $F_c$, $S_cF_v$). Such a construct would be useful in targeting AIF to cells expressing antigens that would bind to the antibodies or fragments thereof attached to the AIF (i.e., the fusion protein).

In another aspect, the pGEX vector [Smith et al., Gene 67:31-40 (1988)] can be used. This vector fuses the *Schistosoma japonicum* glutathionine S-transferase cDNA to the sequence of interest. Bacterial proteins are harvested and recombinant proteins can be quickly purified on a reduced glutathione affinity column. The GST carrier can subsequently be cleaved from fusion proteins by digestion with site-specific proteases. After cleavage, the carrier and uncleaved fusion protein can be removed by absorption on glutathione agarose. Difficulty with the system occasionally arises when the encoded protein is insoluble in aqueous solutions.

Expression of recombinant proteins in bacterial systems may result in incorrect folding of the expressed protein, requiring refolding. The recombinant protein can be refolded prior to or after cleavage to form a functionally active AIF polypeptide. The AIF polypeptide may be refolded by the steps of (i) incubating the protein in a denaturing buffer that contains a reducing agent, and then (ii) incubating the protein in a buffer that contains an oxidizing agent, and preferably also contains a protein stabilizing agent or a chaotropic agent, or both. Suitable redox (reducing/oxidizing) agent pairs include, but are not limited to, reduced glutathione/glutathione disulfide, cystine/cysteine, cystamine/cysteamine, and 2-mercaptoethanol/2-hydroxyethyldisulfide. In a particular aspect, the fusion protein can be solubilized in a denaturant, such as urea, prior to exchange into the reducing buffer. In preferred embodiment, the protein is also purified, e.g., by ion exchange or Ni-chelation chromatography, prior to exchange into the reducing buffer. Denaturing agents include but are not limited to urea and guanidine-HCl. The recombinant protein is then diluted about at least 10-fold, more preferably about 100-fold, into an oxidizing buffer that contains an oxidizing agent, such as but not limited to 0.1 M Tris-HCl, pH 8.0, 1 mM EDTA, 0.15 M NaCl, 0.3 M oxidized glutathione. The fusion protein is then incubated for about 1 to about 24 hours, preferably about 2 to about 16 hours, at room temperature in the oxidizing buffer. The oxidizing buffer may comprise a protein stabilizing agent, e.g., a sugar, an alcohol, or ammonium sulfate. The oxidizing buffer may further comprises a chaotropic agent at low concentration, to destabilize incorrect intermolecular interactions and thus promote proper folding. Suitable chaotropic agents include but are not limited to a detergent, a polyol, L-arginine, guanidine-HCl and polyethylene glycol (PEG). It is important to use a low enough concentration of the chaotropic agent to avoid denaturing the protein. The refolded protein can be concentrated by at least about 10-fold, more preferably by the amount it was diluted into the oxidizing buffer.

Bacterial fermentation processes can also result in a recombinant protein preparation that contains unacceptable levels of endotoxins. Therefore, the invention contemplates removal of such endotoxins, e.g., by using endotoxin-specific antibodies or other endotoxin binding molecules. The presence of endotoxins can be determined by standard techniques, such as by employing E-TOXATE Reagents (Sigma, St. Louis, Mo.), or with bioassays.

In addition to the specific example, the present inventors contemplate use of baculovirus, mammalian, and yeast expression systems to express the AIF polypeptides. For example, in baculovirus expression systems, both non-fusion transfer vectors, such as but not limited to pVL941 (BamH1 cloning site;), pVL1393 (BamH1, SmaI, XbaI, EcoR1, NotI, XmaIII, BglII, and PstI cloning site; Invitrogen), pVLI392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen).

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; Kaufman, *Current Protocols in Molecular Biology*, 16:12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NotI, and KpnI cloning site, RSV-LTR promoter, histidinol selectable marker; Invitrogen), pREP9 (KpnI, NheI, HindIII, NotI, XhoI, SfiI, and BamH1 cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express AIF polypeptides. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESH is A, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

It is further intended that AIF analogs may be prepared from nucleotide sequences derived within the scope of the present invention.

In addition to recombinant expression of the AIF polypeptide, the present invention envisions and fully enables preparation of AIF polypeptide, or fragments thereof, using the well known and highly developed techniques of solid phase peptide synthesis. The invention contemplates using both the popular Boc and Fmoc, as well as other protecting group strategies, for preparing the AIF polypeptide or fragments thereof. Various techniques for refolding and oxidizing the cysteine side chains to form a disulfide bond are also well-known in the art.

Antibodies to the AIF Polypeptide

According to the invention, the AIF polypeptide produced recombinantly or by chemical synthesis, and fragments or other derivatives or analogs thereof, including fusion proteins, may be used as an immunogen to generate antibodies that recognize the AIF polypeptide. Such antibodies include but are not limited to polyclonal, monoclonal, chimeric, single chain, Fab fragments, and an Fab expression library.

For the purposes of this disclosure, the following definitions are relevant. A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, F(ab')$_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds antigen.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response [Hood et al., in *Immunology*, p. 384, Second Ed., Benjamin/Cummings, Menlo Park, Calif. (1984)]. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Various procedures known in the art may be used for the production of polyclonal antibodies to AIF polypeptide, or fragment, derivative or analog thereof. For the production of antibody, various host animals can be immunized by injection with the AIF polypeptide, or a derivative (e.g., fragment or fusion protein) thereof, including but not limited to rabbits, mice, rats, sheep, goats, etc. In one embodiment, the AIF polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the AIF polypeptide, or fragment, analog, or derivative thereof, any technique that provides for the production of antibody molecules by continuous cell lines in culture may be used. These include but are not limited to the hybridoma technique originally developed by Kohler et al. [*Nature*, 256:495-497 (1975)], as well as the trioma technique, the human B-cell hybridoma technique [Kozbor et al., *Immunology Today*, 4:72 (1983)], and the EBV-hybridoma technique to produce human monoclonal antibodies [Cole et al., in *Monoclonal Antibodies and Cancer Therapy*, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); also U.S. Pat. Nos. 4,341,761; 4,399,121; 4,427,783; 4,444, 887; 4,451,570; 4,466,917; 4,472,500; 4,491,632; and 4,493,890.

In an additional embodiment of the invention, monoclonal antibodies can be produced in germ-free animals utilizing recent technology (international application no. PCT/US90/ 02545). According to the invention, human antibodies may be used and can be obtained by using human hybridomas [Cote et al., *Proc. Natl. Acad. Sci. USA*, 80:2026-2030 (1983)] or by transforming human B cells with EBV virus in vitro [Cole et al, 1985, supra]. In fact, according to the invention, techniques developed for the production of "chimeric antibodies" [Morrison et al., *J. Bacteriol.*, 159-870 (1984); Neuberger et al., *Nature*, 312:604-608 (1984); Takeda et al., *Nature*, 314:452-454 (1985)] by splicing the genes from a mouse antibody molecule specific for an AIF polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946, 778) can be adapted to produce AIF polypeptide-specific single chain antibodies. An additional embodiment of the invention utilizes the techniques described for the construction of Fab expression libraries [Huse et al., *Science*, 246: 1275-1281 (1989)] to allow rapid and easy identification of monoclonal Fab fragments with the desired specificity for an AIF polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffision assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an AIF polypeptide, one may assay generated hybridomas for a product which binds to an AIF polypeptide fragment containing such epitope. For selection of an antibody specific to an AIF polypeptide from a particular species of animal, one can select on the basis of positive binding with the AIF polypeptide expressed by or isolated from cells of that species of animal.

The foregoing antibodies can be used in methods known in the art relating to the localization and activity of the AIF polypeptide, e.g., for Western blotting, imaging the AIF polypeptide in situ, measuring levels thereof in appropriate physiological samples.

In a specific embodiment, antibodies that agonize or antagonize the activity of AIF polypeptide can be generated. Such antibodies can be tested using the assays described infra for identifying ligands.

In a specific embodiment, antibodies are developed by immunizing rabbits with synthetic peptides predicted by the protein sequence or with recombinant proteins made using bacterial expression vectors. The choice of synthetic peptides is made after careful analysis of the predicted protein structure, as described above. In particular, peptide sequences between putative cleavage sites are chosen. Synthetic peptides are conjugated to a carrier such as KLH hemocyanin or BSA using carbodiimide and used in Freunds adjuvant to immunize rabbits. In order to prepare recombinant protein, the pGEX vector can be used to express the polypeptide [Smith et al., 1988, supra]. Alternatively, one can use only hydrophilic domains to generate the fusion protein. The expressed protein will be prepared in quantity and used to immunize rabbits in Freunds adjuvant.

In another specific embodiment, recombinant AIF polypeptide is used to immunize chickens, and the chicken anti-AIF antibodies are recovered from egg yolk, e.g., by affinity purification on an AIF-column. Preferably, chickens used in immunization are kept under specific pathogen free (SPF) conditions.

In yet another embodiment, recombinant AIF polypeptide is used to immunize rabbits, and the polyclonal antibodies are immunopurified prior to further use. The purified antibodies are particularly useful for semi-quantitative assays, particularly for detecting the presence of circulating AIF polypeptide in serum or plasma.

Monoclonal antibodies produced against AIF polypeptides can be screened for various properties; i.e., isotype, epitope, affinity, etc. Of particular interest are monoclonal antibodies that neutralize the activity of the AIF polypeptides. Such monoclonals can be readily identified in activity assays for the AIF. High affinity antibodies are also useful when immunoaffinity purification of native or recombinant modulator is possible.

Preferably, the anti-modulator antibody used in the diagnostic and therapeutic methods of this invention is an affinity-purified polyclonal antibody. More preferably, the antibody is a monoclonal antibody (mAb). In addition, it is preferable for the anti-modulator antibody molecules used herein be in the form of Fab, Fab', F(ab')$_2$ or F(v) portions of whole antibody molecules.

Diagnostic Implications

The present invention also relates to a variety of diagnostic applications, including methods for detecting the presence of conditions and/or stimuli that impact upon abnormalities involving the hypo- or hyper-induction of apoptosis, by reference to their ability to elicit the activities which are mediated by the present AIFs. As mentioned earlier, the AIF polypeptide may be used to produce antibodies to themselves by a variety of known techniques, and such antibodies may then be isolated and utilized in tests for the presence of particular transcriptional activity in suspect target cells, alternatively, the nucleic acids of the invention can be employed in diagnosis.

Antibody-based Diagnostics

As suggested earlier, a diagnostic method useful in the present invention comprises examining a cellular sample or medium by means of an assay including an effective amount of an antagonist to a modulator protein, such as an anti-modulator antibody, preferably an affinity-purified polyclonal antibody, and more preferably a mAb. In addition, it is preferable for the anti-modulator antibody molecules used herein be in the form of Fab, Fab', F(ab')$_2$ or F(v) portions or whole antibody molecules. Patients capable of benefitting from this method include those suffering from various neoplastic diseases, neurodegenerative diseases (for example, but not limited to neurodegeneration due to stroke, Alzheimer's disease, Parkinson's disease and amyotrophic lateral sclerosis) or other conditions where abnormal apoptosis induction (either hypo- or hyperinduction) is a characteristic or factor [Science, 281(5381); Aug. 28, 1998]. Methods for isolating the modulator and inducing anti-modulator antibodies and for determining and optimizing the ability of anti-modulator antibodies to assist in the examination of the target cells are all well-known in the art.

Also, antibodies including both polyclonal and monoclonal antibodies, and drugs that modulate the production or activity of the AIFs and other recognition factors and/or their subunits may possess certain diagnostic applications and may for example, be utilized for the purpose of detecting and/or measuring conditions where abnormalities in the induction or lack of induction of apoptosis are or may be likely to develop. For example, the AIF polypeptides or their active fragments may be used to produce both polyclonal and monoclonal antibodies to themselves in a variety of cellular media, by known techniques, such as the hybridoma technique utilizing, for example, fused mouse spleen lymphocytes and myeloma cells. These techniques are described in detail below. Likewise, small molecules that mimic or antagonize the activity(ies) of the receptor recognition factors of the invention may be discovered or synthesized, and may be used in diagnostic and/or therapeutic protocols.

The presence of AIFs in cells can be ascertained by the usual immunological procedures applicable to such determinations. A number of useful procedures are known. Three such procedures which are especially useful utilize either the receptor recognition factor labeled with a detectable label, antibody $Ab_1$ labeled with a detectable label, or antibody $Ab_2$ labeled with a detectable label. The procedures may be summarized by the following equations wherein the asterisk indicates that the particle is labeled, and "AIF" refers to the apoptosis-inducing factor.:

A. $AIF^* + Ab_1 = AIF^* Ab_1$

B. $AIF + Ab^*_1 = AIFAb^{1*}$

C. $AIF + Ab_1 + Ab_2^* = Ab_1 AIFAb_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure B is representative of well known competitive assay techniques. Procedure C, the "sandwich" procedure, is described in U.S. Pat. Nos. RE 31,006 and 4,016,043. Still other procedures are known such as the "double antibody", or "DASP" procedure.

In each instance, the AIFs form complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$, raised in one mammalian species, has been used in another species as an antigen to raise the antibody, $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-AIF antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The AIFs or their binding partners can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, test kits suitable for use by a medical specialist may be prepared to determine the presence or absence of predetermined transcriptional activity or predetermined transcriptional activity capability in suspected target cells. In accordance with the testing techniques discussed above, one class of such kits will contain at least the labeled AIF or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined transcriptional activity, comprising:

(a) a predetermined amount of at least one labeled immunochemically reactive component obtained by the direct or indirect attachment of the present AIF or a specific binding partner thereto, to a detectable label;

(b) other reagents; and (c) directions for use of said kit.

More specifically, the diagnostic test kit may comprise:

(a) a known amount of the AIF as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the AIF to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the AIF and a specific binding partner thereto.

Therapeutic Implications

The polypeptides, nucleic acids, and antibodies of the invention have significant therapeutic potential. Optionally, a therapeutically effective amount of such an agent is administered in a pharmaceutically acceptable carrier, diluent, or excipient.

For the purposes of this disclosure, the following definitions are relevant. The phrase "pharmaceutically acceptable" refers to molecular entities and compositions that are physiologically tolerable and do not typically produce an allergic or similarly untoward reaction, such as gastric upset, dizziness and the like, when administered to a human, and which preferably does not interfere with the administration of the protein administered. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or solution saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa., (1990).

The phrase "therapeutically effective amount" is used herein to mean an amount sufficient to reduce by at least about 15%, preferably by at least 50%, more preferably by at least 90%, and most preferably prevent, a clinically significant deficit in the activity, function and response of the host. Alternatively, a therapeutically effective amount is sufficient to cause an improvement in a clinically significant condition in the host.

Administration of recombinant AIF polypeptide (or fragments, analogs, or homologs of AIF as described above, that incorporate AIF-like activity) to cells results in the induction of apoptosis. Such administration might be help in treating and controlling a number of neoplastic diseases, for example, but not limited to lymphoma, neoplastic diseases of the central nervous system, sarcoma, melanoma, mesothelioma, or any neoplastic disease of the other organs of the body (for example, but not limited prostate, lung, muscle, liver, stomach, bladder, uterus). AIF polypeptide may be prepared using standard bacterial and/or mammalian expression vectors, synthetically, or purified from plasma or serum, all as stated in detail earlier herein. Alternatively, increased expression of native AIF polypeptide may be induce by homologous recombination techniques, as described supra.

Reduction of AIF polypeptide activity (by developing antagonists, inhibitors, use of neutralizing antibodies, or antisense molecules, all produced as described herein) should result in decreased apoptosis. Such activity might be desirable for the treatment of various neurodegenerative diseases that have been linked to the induction of apoptosis. (to neurodegeneration due to stroke, Alzheimer's disease, Parkinson's disease and amyotrophic lateral sclerosis). Thus, modulation of AIF activity may be useful for controlling or treating neoplastic diseases (by increasing its activity) or treating neurodegenerative diseases (by decreasing its activity).

Polypeptide-based Therapeutic Treatment

In the simplest analysis, the AIF gene product, and, correspondingly, cognate molecules, appear to be part of the apoptotic signaling pathway, wherein apoptosis is induced by AIF. The AIF polypeptide, or functionally active fragment thereof, or an antagonist thereof, can be administered orally or parenterally, preferably parenterally. For example, the polypeptide may be administered using intravenous infusion, an implantable osmotic pump, a transdermal patch, liposomes, or other modes of administration. In one embodiment, a pump may be used [Langer et al., eds., *Medical Applications of Controlled Release*, CRC Pres., Boca Raton, Fla. (1974); Sefton, *CRC Crit. Ref. Biomed. Eng.*, 14:201 (1987); Buchwald et al., *Surgery*, 88:507 (1980); Saudek et al., *N. Engl. J. Med.*, 321:574 (1989)]. In another embodiment, polymeric materials can be used [Langer, 1974, supra; Sefton, 1987, supra; Smolen et al., eds., *Controlled Drug Bioavailability, Drug Product Design and Performance*, Wiley, N.Y. (1984); Ranger et al., *J. Macromol. Sci. Rev. Macromol. Chem.*, 23:61 (1983); Levy et al., *Science*. 228: 190 (1985); During et al., *Ann. Neurol.*, 25:351 (1989); Howard et al., *J. Neurosurg.*, 71:105 (1989)]. In yet another embodiment, a controlled release system can be placed in proximity of the therapeutic target, i.e., the brain, thus requiring only a fraction of the systemic dose [e.g., Goodson, in *Medical Applications of Controlled Release*, vol. 2, pp. 115-138 (1984)]. Other controlled release systems are discussed in the review by Langer, *Science*, 249:1527-1533 (1990). In another embodiment, the therapeutic compound can be delivered in a vesicle, in particular a liposome (Langer, 1990 supra); Treat et al., in *Liposomes in the Therapy of Infectious Disease and Cancer*, Lopez-Berestein and Fidler (eds.), Liss, N.Y., pp. 353-365 (1989); Lopez-Berestein, ibid., pp. 317-327)

In a further aspect, recombinant cells that have been transformed with the AIF gene and that express high levels of the polypeptide can be transplanted in a subject in need of AIF polypeptide. Preferably autologous cells transformed with the AIF gene are transplanted to avoid rejection; alternatively, technology is available to shield non-autologous cells that produce soluble factors within a polymer matrix that prevents immune recognition and rejection.

The AIF polypeptide may be delivered by intravenous, intraarterial, intraperitoneal, intramuscular, or subcutaneous routes of administration. Alternatively, the AIF polypeptide, properly formulated, can be administered by nasal or oral administration. A constant supply of AIF may be ensured by providing a therapeutically effective dose (i.e., a dose effective to induce apoptosis in the target area) at the necessary intervals, e.g., daily, every 12 hours, etc. These parameters will depend on the severity of the disease condition being treated, other actions, the weight, age, and sex of the subject, and other criteria, which can be readily determined according to standard good medical practice by those of skill in the art.

Compositions/Pharmaceutical Compositions

In yet another aspect of the present invention, provided are compositions pharmaceutical compositions of the above. Such pharmaceutical compositions may be for administration for injection, or for oral, pulmonary, nasal or other forms of administration. In general, comprehended by the invention are pharmaceutical compositions comprising effective amounts of protein (AIF) or derivative products (e.g., fragments, homologs, variants of AIF) of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g, ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives, e.g., Martin, *Remington's Pharmaceutical Sciences*, 18th Ed. [1990, Mack Publishing Co., Easton, Pa. 18042] pages 1435-1712 which are herein incorporated by reference. The compositions may be prepared in liquid form, or may be in dried powder, such as lyophilized form.

Oral Delivery

Contemplated for use herein are oral solid dosage forms, which are described generally in *Martin, Remington's Pharmaceutical Sciences*, 18th Ed. [1990 Mack Publishing Co. Easton Pa. 18042] at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013, 556). A description of possible solid dosage forms for the therapeutic is given by Marshall, in *Modern Pharmaceutics*, Chapter 10, Banker and Rhodes ed., (1979), herein incorporated by reference. In general, the formulation will include the protein (or chemically modified protein), and inert ingredients which allow for protection against the stomach environment, and release of the biologically active material in the intestine.

Also specifically contemplated are oral dosage forms of the above derivatized proteins. Protein may be chemically modified so that oral delivery of the derivative is efficacious. Generally, the chemical modification contemplated is the attachment of at least one moiety to the protein (or peptide) molecule itself, where said moiety permits (a) inhibition of proteolysis; and (b) uptake into the blood stream from the stomach or intestine. Also desired is the increase in overall stability of the protein and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline [Abuchowski et al., 1981, supra; Newmark et al., *J. Appl. Biochem.*, 4:185-189 (1982)]. Other polymers that could be used are poly-1,3-dioxolane and poly-1,3,6-tioxocane. Preferred for pharmaceutical usage, as indicated above, are polyethylene glycol moieties.

For the protein (or derivative) the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to: stearic acid including its magnesium and calcium salts, polytetrafluoroethylene (PTFE), liquid, paraffin, vegetable oils and waxes. Soluble lubricants may also be used such as sodium lauryl sulfate, magnesium lauryl sulfate, polyethylene glycol of various molecular weights, and Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the protein (or derivative) are for instance the fatty acids oleic acid, linoleic acid and linolenic acid.

Controlled release formulation may be desirable. The composition could be incorporated into an inert matrix which permits release by either diffusion or leaching mechanisms i.e., gums. Slowly degenerating matrices may also be incorporated into the formulation. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film-coated tablet; the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Pulmonary Delivery

Also contemplated herein is pulmonary delivery of the present protein (or derivatives thereof). The protein (or derivative) is delivered to the lungs of a mammal while inhaling and traverses across the lung epithelial lining to the blood-stream. Other reports of this include Adjei et al., *Pharmaceutical Research,* 7(6):565-569 (1990); Adjei et al., *International Journal of Pharmaceutics,* 63: 135-144 (1990) (leuprolide acetate); Braquet et al., *Journal of Cardiovascular Pharmacology,* 13(suppl. 5):143-146 (1989) (endothelin-1); Hubbard et al., *Annals of Internal Medicine,* 3(3): 206-212 (1989) (α1-antitrypsin); Smith et al., *J. Clin. Invest.,* 84:1145-1146 (1989) (α1-proteinase); Oswein et al., "Aerosolization of Proteins", *Proceedings of Symposium on Respiratory Drug Delivery II,* Keystone, Colo., (March 1990) (recombinant human growth hormone); Debs et al., *J. Immunol.,* 140:3482-3488 (1988) and Platz et al., U.S. Pat. No. 5,284,656 (granulocyte colony stimulating factor). Contemplated for use in the practice of this invention are a wide range of mechanical devices designed for pulmonary delivery of therapeutic products, including but not limited to nebulizers, metered-dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of protein (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified protein may also be prepared in different formulations depending on the type of chemical modification or the type of device employed.

Formulations suitable for use with a nebulizer, either jet or ultrasonic, will typically comprise protein (or derivative) dissolved in water at a concentration of about 0.1 to 25 mg of biologically active protein per ml of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the protein (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing protein (or derivative) and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 μm (or microns), most preferably 0.5 to 5 μm, for most effective delivery to the distal lung.

Nasal Delivery

Nasal delivery of the protein (or derivative) is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Methods of Treatment, Methods of Preparing a Medicament

In yet another aspect of the present invention, methods of treatment and manufacture of a medicament are provided. Conditions alleviated by or modulated by the administration of the present derivatives are those indicated above.

Dosages

For all of the above molecules, as further studies are conducted, information will emerge regarding appropriate dosage levels for treatment of various conditions in various patients, and the ordinary skilled worker, considering the therapeutic context, age and general health of the recipient, will be able to ascertain the proper dosage. Generally, for injection or infusion, dosage will be between 0.01 μg of biologically active protein/kg body weight, (calculating the mass of the protein alone, without chemical modification), and 10 mg/kg (based on the same). The dosing schedule may vary, depending on the circulation half-life of the protein or derivative used, whether the polypeptide is delivered by bolus dose or continuous infusion, and the formulation used.

Administration with Other Compounds/Treatment Modalities

For therapy associated with abnormalities related to lack of induction of apoptosis, one may administer the present protein (or derivatives) in conjunction with one or more pharmaceutical compositions used for treating the underlying clinical complication (i.e., cancer: radiotherapy and/or chemotherapy). Administration may be simultaneous or may be in seriatim.

Nucleic Acid-based Therapeutic Treatment

The AIF polynucleotide may be introduced into cells to develop gene therapy for abnormalities related to lack of induction of apoptosis (e.g., neoplastic diseases). Such therapy would be expected to control such cancers. Conversely, introduction of antisense constructs into human cells having abnormally high rates of apoptosis (e.g., neurodegenerative disease) would reduce the levels of active AIF polypeptide and would be predicted to alleviate the underlying symptoms.

In one embodiment, a gene encoding an AIF polypeptide is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Such viruses are not infective after introduction into a cell. Use of the foregoing viral vectors allows for administration to cells in a specific, localized area, without concern that the vector can infect other cells. Thus, for example cancerous tissue may be specifically targeted. Examples of particular vectors include, but are not limited to, a herpes virus 1 (HSV1) vector [Kaplitt et al., *Molec. Cell. Neurosci.*, 2:320-330 (1991)], see U.S. Pat. No. 5,288,641 to Roizman, an attenuated adenovirus vector, such as the vector described by Stratford-Perricaudet et al., *J. Clin. Invest.*, 90:626-630 (1992), and a defective adeno-associated virus vector [Samulski et al., *J. Virol.*, 61:3096-3101 (1987); Samulski et al., *J. Virol.*, 63:3822-3828 (1989)].

In another embodiment, the gene can be introduced in a retroviral vector, e.g., as described in Anderson et al., U.S. Pat. No. 5,399,346; Mann et al., *Cell*, 33:153 (1983); Temin et al., U.S. Pat. No. 4,650,764; Temin et al., U.S. Pat. No. 4,980,289; Markowitz et al., *J. Virol.*, 62:1120 (1988); Temin et al., U.S. Pat. No. 5,124,263; International Patent Publication No. WO 95/07358, published Mar. 16, 1995, by Dougherty et al.; and Kuo et al., *Blood*, 82:845 (1993).

With respect to the use of viral vectors to deliver a gene-based therapy, the AIF polynucleotide or fragment thereof is preferably under the control of a promoter capable of being expressed in the target cells (operatively-linked to a promoter that functions in the context of a viral genome), e.g., antisense constructs (see above) for the treatment of neurodegenerative diseases or any other disease characterized by hyper-induction of apoptosis.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner et al., *Proc. Natl. Acad. Sci. USA*, 84:7413-7417 (1987);

Mackey et al., *Proc. Natl. Acad. Sci. USA*, 85:8027-8031 (1988)]. The use of cationic lipids may promote encapsulation of negatively charged nucleic acids, and also promote fusion with negatively charged cell membranes [Felgner et al., *Science*, 337:387-388 (1989)]. The use of lipofection to introduce exogenous genes into specific organs in vivo has certain practical advantages. Molecular targeting of liposomes to specific cells represents one area of benefit. It is clear that directing transfection to particular cell types would be particularly advantageous in a tissue with cellular heterogeneity, such as the pancreas, liver, kidney, and brain. Lipids may be chemically coupled to other molecules for the purpose of targeting [Mackey et al., 1988, supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [Wu et al., *J. Biol. Chem.*, 267:963-967 (1992); Wu et al., *J. Biol. Chem.*, 263:14621-14624 (1988); Hartmut et al., Canadian Patent Application No. 2,012,311, filed Mar. 15, 1990].

The AIF Binding Partner

Development of small molecule agonists and antagonists of the AIF will be greatly facilitated by the isolation of the AIF binding partner(s). This can be accomplished by preparing active AIF polypeptide and using it to screen an expression library using standard methodology. Binding partner binding in the expression library can be tested by administering recombinant polypeptide prepared using either bacterial or mammalian expression vectors, and observing the effects of short term and continuous administration of the recombinant polypeptide on the cells of the expression library.

cDNA libraries from tissues thought to contain AIF may be constructed in standard expression cloning vectors. These cDNA clones would next be introduced into COS cells as pools and the resulting transformants would be screened with active ligand to identify COS cells expressing the AIF binding partner. Positive clones can then be isolated so as to recover the cloned binding partner. The cloned binding partner would be used in conjunction with the AIF ligand to develop the necessary components for screening of small molecule modulators of AIF.

A useful and contemplated assay in accordance with the present invention is known as a "cis/trans" assay. Briefly, this assay employs two genetic constructs, one of which is typically a plasmid that continually expresses a particular binding partner of interest when transfected into an appropriate cell line, and the second of which is a plasmid that expresses a reporter such as luciferase, under the control of a receptor/ligand complex. Thus, for example, if it is desired to evaluate a compound as a ligand for a particular binding partner, one of the plasmids would be a construct that results in expression of the binding partner in the chosen cell line, while the second plasmid would possess a promoter linked to the luciferase gene in which the response element to the particular binding partner is inserted. If the compound under test is an agonist for the binding partner, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred. Once a recombinant which expresses the AIF binding partner gene sequence is identified, the recombinant AIF binding partner can be analyzed. This is achieved by assays based on the physical or functional properties of the AIF binding partner, including radioactive labeling of the binding partner followed by analysis by gel electrophoresis, immunoassay, ligand binding, etc. Furthermore, antibodies to the AIF binding partner may be generated as described above.

The structure of the AIF binding partner can be analyzed by various methods known in the art. Preferably, the structure of the various domains, particularly the AIF binding site, is analyzed. Structural analysis can be performed by identifying sequence similarity with other known proteins, particular hormone and protein binding partner. The degree of similarity (or homology) can provide a basis for predicting structure and function of the AIF binding partner, or a domain thereof. In a specific embodiment, sequence comparisons can be performed with sequences found in GenBank, using, for example, the FASTA and FASTP programs [Pearson et al., *Proc. Natl. Acad. Sci. USA*, 85:2444-2448 (1988)].

The protein sequence can be further characterized by a hydrophilicity analysis, e.g., Hopp et al., 1981, supra. A hydrophilicity profile can be used to identify the hydrophobic and hydrophilic regions of the AIF binding partner, which may in turn indicate extracytoplasmic, membrane binding, and intracytoplasmic regions.

Secondary structural analysis, e.g., Chou et al., 1974, supra, can also be undertaken, to identify regions of the AIF binding partner that assume specific secondary structures. Manipulation, translation, and secondary structure prediction, as well as open reading frame prediction and plotting, can also be accomplished using computer software programs available in the art.

By providing an abundant source of recombinant AIF polypeptide, and the opportunity to isolate the AIF binding partner, the present invention enables quantitative structural determination of the active conformation of the AIF polypeptide and the AIF binding partner, or domains thereof. In particular, enough material is provided for nuclear magnetic resonance (NMR), infrared (IR), Raman, and ultraviolet (UV), especially circular dichroism (CD), spectroscopic analysis. In particular NMR provides very powerful structural analysis of molecules in solution, which more closely approximates their native environment (Marion et al., 1983, supra; Bar et al., 1985, supra; Kimura et al., 1980, supra). Other methods of structural analysis can also be employed. These include but are not limited to X-ray crystallography (Engstom, 1974, supra).

More preferably, co-crystals of AIF polypeptide and AIF binding partner can be studied. Analysis of co-crystals provides detailed information about binding, which in turn allows for rational design of ligand agonists and antagonists. Computer modeling can also be used, especially in connection with NMR or X-ray methods [Fletterick et al., eds., *Computer Graphics and Molecular Modeling*, in *Current Communications in Molecular Biology*, Cold Spring Harbor Laboratory, Cold Spring Harbor, N.Y. (1986)].

Identification and isolation of a gene encoding an AIF binding partner of the invention provides for expression of the receptor in quantities greater than can be isolated from natural sources, or in indicator cells that are specially engineered to indicate the activity of a binding partner expressed after transfection or transformation of the cells. Accordingly, in addition to rational design of agonists and antagonists based on the structure of the AIF polypeptide, the present invention contemplates an alternative method for identifying specific ligands of AIF binding partner using various screening assays known in the art.

The invention is illustrated by the following examples, which are not intended to limit the scope of the invention as recited in the claims.

Example 1 provides methods for cloning and expressing the mouse AIF.

Example 2 provides methods for the production of anti-AIF antisera as well as methods for immunofluoresence, immunoelectron microscopy, and immunodepletion experimental protocols.

Example 3 provides methods for experimental protocols involving subcellular fractionation and cell-free systems of apoptosis.

Example 4 provides methods for microinjection, transfection, and quantitation of apoptosis.

Example 5 describes the alternative isoforms of mouse AIF.

Example 6 describes the cloning of human AIF.

Example 7 described the alternative isoforms of human AIF.

Example 8 provides methods for the construction of the full-length human AIF cDNA.

Example 9 provides methods for the culturing of host cells and the subsequent induction of recombinant protein (AIF).

Example 10 describes the purification of full-length recombinant AIF fusion protein.

Example 11 describes the use of the yeast di-hybrid assay to identify binding partners for AIF.

EXAMPLE 1

Cloning of Mouse AIF cDNA and Recombinant Production Thereof

In order to determine the DNA sequence encoding mAIF, the polypeptide was subjected to protein purification, followed by amino acid sequence analysis, and computer analysis alignment with GenBank ESTs. Following the determination of both the 5' start and 3' stop of mAIF, RT-PCT analysis was undertaken to verify that the mAIF contig obtained formed one continuous open reading frame. (see below for actual methods).

mAIF Purification/EST Alignment mAIF (mouse AIF) was purified from the supernatant of atractyloside-treated mouse liver mitochondria as previously described [Wada et al., Proc. Natl. Acad. Sci. USA 95:144-149 (1998)], subjected to SDS-PAGE, silver-staining, excision of the ~57 kda band, in situ digestion with trypsin, peptide extraction, injection onto a microcapillary HPLC column (50 micron i.d.×10 cm) packed with C-18 (YMC ODS-AQ), and electrospray ionization on a triple quadrupole mass spectrometer (Finnigan, San Jose, Calif.) during linear gradient elution of peptides with acetonitrile.

Mass spectrometric data were analyzed with the computer routine SEQUEST, allowing for-the correlation of high-energy collision-induced dissociation spectra of peptides with all sequences in public protein databases [Ducret et al., Protein Sci. 7:706-719 (1998)]. Briefly (see below for additional detail), an expressed sequence tag (GenBank EST #1595214) matching the electrospray data was aligned with several other mouse ESTs in the NCBI database (e.g. GenBank accession Nos. AA106466 and AA068609). These ESTs were obtained from the IMAGE consortium (Research Genetics, Huntsville, Ala.) and sequenced to generate a mouse AIF cDNA contig that was subsequently used to clone the full-length cDNA of mouse and human AIF via RT-PCR. Northern blot analyses were performed using the entire mAIF cDNA as a probe.

More specifically, the following mouse ESTs aligned to form the preliminary mouse AIF cDNA contig: GenBank# AA106466 (the most 5'EST clone), GenBank# AA572575, GenBank #W77437, GenBank #AA155062, GenBank# AA516860, GenBank# AA088093, GenBank# AA073449, and GenBank# AA134414.

Determining the 5 'Start (ATG) of mAIF

The most 5' mouse EST clone (GenBank# AA106466) and two human ESTs (GenBank #AA337888, and dbj# C0371 1), which were believed to correspond to orthologous AIF sequences, all began at similar positions. This phenomenon is often indicative of EST clones representing the start of transcription.

Alignment of the mouse (GenBank# AA106466) and human (obj# C03711) AIF ESTs revealed that they were most divergent at the extreme 5' ends and actually contained a 2 nucleotide gap in the alignment in the 5' end. Because this gap in the alignment would disrupt the reading frame, it was concluded that the divergent area of the sequence represented the 5' untranslated region. Translation of each of these ESTs in all 3 frames revealed that only one reading frame continued on in the 5' to 3' direction without stop codons and this frame was the same for both the mouse (GenBank# AA106466) and human (GenBank# AA337888, and dbj# C03711) AIF ESTs. Furthermore, the cross species alignments allowed verification this same reading frame of the 5' end of AIF because the mouse and human AIF sequences usually differed at nucleotides, which were located at multiples of 3 nucleotides away from each other and were therefore occupying the "Wobble" position or third nucleotide of the three letter codon. Translation of the mouse and human AIF ESTs in this frame identified the start methionine. The presence of the G at position −3 from the start codon (ATG) in both the mouse and human EST clones is consistent with the Kozak consensus of either an A or a G at the −3 position from the start methionine. This therefore lends further support to this being the true start methionine of AIF.

Determining the 3 ' Stop of the mAIF cDNA

Alignment of the mAIF cDNA contig with other ESTs in the N.C.B.I. database identified an additional mouse EST (GenBank# AA068609), which extended the mouse AIF contig even further 3'. It is thought that this mouse EST clone was presumably missed because it only overlapped with the original contig by 37 nucleotides.

This additional mouse EST clone (GenBank#AA068609) was available and thus obtained from the I.M.A.G.E. consortium (cDNA ID#524752; located in pBlueScript SK-vector; EST cDNA was cloned from a Stratagene mouse M2 melanoma (#937312). Once obtained, the bacteria containing the EST clone was subjected to the following protocol.

A sterile loop was used to inoculate 3.5 ml of LB broth (containing 50 μg of carbenacillin/ml) and the bacteria was grown in a shaking incubator at 37° C. for 16 hours. A Qiagen Plasmid Miniprep Kit (Qiagen Inc. Mississauga, ON, catalogue#12125) was then used to prepare plasmid DNA from this culture according to the manufacturer's instructions. The plasmid DNA was suspended in 30 μL of 1×T.E. buffer (pH 8.0) and subjected fluorescent dideoxy-nucleotide sequencing and automated detection (ABI/Perkin Elmer, Foster City, Calif.) with T7 and T3 primers.

Sequencing of this EST clone using T3 and T7 primers revealed that this clone contained the putative 3' stop for mouse AIF because it contained stops in all 3 reading frames (FIGS. 8A-8G).

In order to determine the correct reading frame of the 3' end of mouse AIF, a BLAST search was performed against the N.C.B.I. EST database using the newly generated sequence data. This new sequence data aligned with ESTs from rat (Genbank#AA891591) and ESTs from human tissues (e.g. GenBank#AA570483). The cross species alignments allowed us to determine the reading frame of the 3' end of mouse AIF because the sequences usually differed at nucleotides which were located at multiples of 3 nucleotides away from each other and were therefore occupying the "Wobble" position or third nucleotide of the three letter codon (FIGS. 5A-5H). When the 3' mouse AIF EST was translated in this frame identification of the 3' stop codon was possible.

RT-PCR of the Full Length mAIF cDNA Open-reading Frame:

In order to verify that the mAIF contig obtained above formed one continuous open reading frame, primers flanking the mouse AIF cDNA open reading frame using the oligo-nucleotide design program were designed using Oligo version 4.0. Specifically, the primers were as follows:

```
sense primer:
5'-ACGGTGCGTGGAAGGAAAAGGAAGG-3'     (SEQ ID NO. 16)

antisense primer:
5'-CGCCAGGGATGGAAAAGTGCTTGTG-3'.    (SEQ ID NO 17)
```

Based on the foregoing contig information, this primer set was predicted to amplify a fragment of approximately 1.9 kb.

RT-PCR amplifications were performed in a 50 μl volume containing 200 μM dNTPs, 0.5 μM of each primer, 10 mM Tris-HCl (pH 8.3), 1.5 mM MgCl$_2$, 50 mM KCl, 2 ng of mouse brain cDNA (Clontech "quick-clone" cDNA Catalogue#7130-1), and 5 units of Expand™ Hi-Fi DNA polymerase (Boehringer Mannheim GmbH, Germany). The PCR reactions were amplified using a "Touch-down/Touch-up" annealing temperature protocol (Snow et al. *Biochem. Biophy. Res. Comm.*, 233:770-777 (1997) and Snow et al., *Gene.* 206:247-253 (1998)) in a PTC-100 programmable thermal cycler (MJ Research Inc.) with the following conditions: initial denaturation of 95° C. for 40 s, 5 cycles at 94° C. for 20 s, 70° C.-2°/Cycle for 20 s, 72° C. for 1 minute and 19 sec+1 s/cycle, followed by 5 cycles at 94° C. for 25 s, 62° C.+1 ° C./cycle for 20 s, 72° C. for 1 minute and 30 s+1 s/cycle, followed by 20 cycles at 94° C. for 25 s, 66° C. for 20 s, 72° C. for 1 minute and 40 s+1 s/cycle, and a final incubation of 72° C. for 5 minutes. The resulting ~1.9 kb PCR products were then gel purified from a 1.0% agarose gel using the QiaQuick Gel purification system (QIAGEN Inc., Chatsworth, Calif.), TA-cloned into pCR2.1 using the TOPO TA Cloning® kit (Invitrogen, San Diego, Calif., Catalogue #K4550-40), and transformed into *E. coli* TOP10F' cells. Plasmid DNA was prepared using the Qiagen Plasmid Miniprep Kit (Qiagen Inc. Mississauga, ON, catalogue#12125). The sequence of the insert was obtained using fluorescent dideoxy-nucleotide sequencing and automated detection (ABI/Perkin Elmer, Foster City, Calif.).

Four sequencing primers, which would help sequence the mouse AIF cDNA open reading frame were also designed. The sequencing primers were as follows:

```
sense:
5'TCAGTTCCTCAGATCAGGGCACC-3'      (SEQ ID NO: 18)

antisense:
5'AAAAACACCAACTGTGGGCAAAC-3'      (SEQ ID NO: 19)

sense:
5'CATCGATAGGGCTGGAGCAGAGG-3'      (SEQ ID NO: 20)

antisense:
5'TTTCCATGGTCCAGTTGCTGAGG-3'.     (SEQ ID NO: 21)
``` pCR2.1-mus-AIF.B1B (DNA #9806532) was sequenced and determined to be 100% sequence perfect by alignment with the mouse AIF EST contig, which had been assembled and by alignment with another independent RT-PCR mouse brain AIF clone: pCR2.1-musAIF.A1A (DNA#9806531). All nucleotides in clonepCR2.1-musAIF.B1B were verified because they were either present in the mouse AIF EST contig, which had been assembled or in pCR2.1-musAIF.A1A which was derived from an independent RT-PCR reaction. The pCR2.1-mus-AIF.B1B was predicted to encode a 612 amino acid polypeptide with a predicted molecular weight of 66.689 kDa. The cDNA sequence is set forth in SEQ ID NO: 1, while the predicted amino acid sequence for the mouse AIF in SEQ ID NO: 2, with the mature protein amino acid sequence set forth in SEQ ID NO: 3.

Recombinant AIF Polypeptide

Thioredoxin tagged mAIF, as well as several AIF deletion mutants generated (in order to determine the active site of the protein) by excision of the DNA sequences with BamH1 (amino acid nos. D180-638), NcoI (amino acid nos. D1-377), or HindIII (amino acid nos. D563-638) were expressed from a Novagen pET32 bacterial expression vector and purified from *E. coli* inclusion bodies (see FIGS. 3 and 4 for data involving use of these deletion mutants). The proteins were refolded on Nickel NTA affinity matrix and stored in 50 mM HEPES, pH 7.9, 100 mM NaCl, 2 mM EDTA, 1 mM DTT and 10% glycerol.

EXAMPLE 2

AIF Antiserum, Immunoblots, Immunofluorescence, Immunoelectron Microscopy, and Immunodepletion In order to determine the protein expression of AIF across a variety of tissues, rabbit antisera was generated against a mixture of three AIF peptides and subjected to the detection methods set forth below.

Specifically, Rabbit antiserum was generated against a mixture of 3 peptides derived from the mAIF amino acid sequence (amino acid nos. 151-170, 166-185, 181-200, coupled to KLH). This antiserum (ELISA titer ~10.000) was used in immunoblots (1/2000) and on paraformaldehyde/picrylic acid-fixed [Bossy-Wetzel et al., *EMBO J.* 17:37-49 (1998)] Rat-1 cells (1/250) and revealed with a goat anti-rabbit IgG conjugated to peroxidase or FITC (green fluorescence), respectively. Cytochrome c was detected by immunofluorescence (mAb 6H2.B4 from Pharmingen) in fixed Rat-1 cells transfected with a control vector (Neo) or with human Bcl-2 [Zhu et al., *EMBO J.* 15:4130-4141

(1996)] as described [Bossy-Wetzel et al., *EMBO J.* 17, 37-49 (1998)], whereas the $DY_m$ sensitive dye CMXRos (100 nM, red fluorescence) was used on live cells [Marzo et al., *Science* 281, 2027-2031 (1998)]. Cells were counterstained with the Hoechst 33342 dye (1 µM, blue fluorescence). Immunoelectron microscopy was performed using an Immunogold (5 nm) anti-rabbit Ig conjugate for revealing the presence of proteins reacting with the anti-AIF antiserum. Immunodepletion of AIF was achieved by immobilizing the antiserum (or a pre-immune serum) on protein A and protein G agarose beads (Santa Cruz Biotechnology: 500 µl antiserum per ml beads) and overnight incubation of mitochondrial intermembrane proteins (100 µg/ml) with these beads (20 µl fluid with 10 µl packed beads), in the presence or absence of the immunogenic peptides (5 µM).

EXAMPLE 3

Subcellular Fractionation and Cell-Free Systems of Apoptosis

The following methods were used in studies to determine the subcellular localization of AIF, as well as in the determination of the effect of AIF on cellular organelle in a cell-free system.

2B4.11 T cell hybridoma cells stably transfected with a SFFV.neo vector containing the human bcl-2 gene or the neomycin resistance gene (Neo) only [Susin et al., *J. Exp. Med.* 184:1331-1342 (1996)] were subjected to mechanical lysis and differential centrifugation for the subsequent recovery of nuclei, mitochondria, and organelle-free cytosols [Liu et al. *Cell* 86:147-157 (1996)]. Submitochondrial fractionation of mouse liver mitochondria was controlled by the determination of suitable marker enzymes [Susin et al., *J. Exp. Med.* 186:25-37 (1997); Pedersen et al., *Meth. Cell Biol.* 20:411-481 (1978)]. Purified HeLa cell nuclei were exposed to different preparations of AIF, and nuclear apoptosis was quantitated by staining with DNA-intercalating propidium iodide and cytofluorometric determination of DNA content [Susin et al., *J. Exp. Med.* 186:25-37 (1997)]. Alternatively, nuclei were stained with Hoechst 33342 dye or subjected to DNA extraction and pulse field gel electrophoresis. Isolated rat liver mitochondria (0.5 mg mitochondrial protein/ml) were exposed to mitochondrion-free cytosol (100 µg protein/ml) [Susin et al., *J. Exp. Med.* 186:25-37 (1997); Enari et al., *EMBO J.* 14:5201-5208 (1995)] and/or recombinant AIF (100 ng/ml), while monitoring for large amplitude swelling at $OD_{540}$. The release of cytochrome c and caspase-9 into the supernatant was measured by immunoblot using a monoclonal anti-cytochrome c antibody (7H8.2C12, Pharmingen), or a rabbit antibody directed against the large subunit of caspase-9 (Hazelton Research Products Inc., Denver, Pa.).

EXAMPLE 4

Microinjection, Transfection, and Quantitation of Apoptosis

Rat-1 fibroblast cells were microinjected (pressure 150 hPa; 0.2 sec; Marzo et al., *Science* 281:2027-2031 (1998)) with buffer only, atractyloside (50 µM), dialyzed antisera, AIF-derived peptides (100 µM), horse cytochrome c (Sigma), or the indicated dose of recombinant mAIF. The caspase inhibitor Z-VAD.fmk (100 µM; Bachem, Basel Switzerland) was added to the culture medium 30 min before microinjection into the cytoplasm (pressure 150 hPa; 0.2 sec). After microinjection, cells were cultured for 90-180 min and stained for 10 min with CMXRos, Hoechst 33342 dye, or Annexin V conjugated to biotin (Boehringer Mannheim) and revealed by an avidin-phycoerythrine conjugate (Sigma). Microinjected viable cells (100-200 per session, two to three independent sessions of injection) were identified by inclusion of 0.25% (w:v) FITC-dextran (green fluorescence) in the injectate. Only the blue or red fluorescence was recorded. Transfection of Jurkat T lymphoma cells was performed using AIF cloned in pcDNA3.1 (Invitrogen) vector and Lipofectamine® (Gibco Life Technologies). Cytofluorometric analyses of apoptosis-associated parameters were performed as described [Kroemer et al., "Detection of apoptosis and apoptosis associated alterations," "*The Immunology Methods Manual*" (Lefkovitz, R. Ed.); Academic Press, Chapter 14.2., pp. 1111-1125 (1997)].

EXAMPLE 5

Identification of Alternative Isoforms of mAIF

Sequence analysis of the other mouse AIF EST clone [CR2.1-musAIF.A1A (Amgen DNA#9806531) and another partial mouse AIF clone: pCR2.1-musAIF-Partial-ORF.B (Amgen DNA#9804781) revealed that the N-terminus of mouse AIF contains an alternative coding sequence which is presumably obtained by alternative exon usage. The mouse partial AIF clone pCR2.1-musAIF-partial-ORF.B (Amgen DNA#9804781) was amplified from mouse brain cDNA using the primers:

```
sense primer# 1874-21:
5'GAGCCACGTGGTCTGTTTGACCCGTTCG-3'    (SEQ ID NO: 22)

antisense primer#: 1874-22:
5'GGAGTTCTGCATTTACCCGGAAGCCACC-3'    (SEQ ID NO: 23)
```

RT-PCR amplifications were performed in a 50 µl volume containing 200 µM dNTPs, 0.5 µM of each primer, 10 mM Tris-HCl (pH 8.3), 1.5 mM $MgCl_2$, 50 mM KCl, 2 ng of mouse brain cDNA (Clontech "quick-clone" cDNA Catalogue#7130-1), and 5 units of Expand™-Hi-Fi DNA polymerase (Boehringer Mannheim GmbH, Germany). The PCR reactions were amplified using a "Touch-down/Touch-up" annealing temperature protocol (Snow et al., *Biochem. Biophy. Res. Comm.*, 233:770-777 (1997) and Snow et al., *Gene.*, 206:247-253 (1998)) in a PTC-100 programmable thermal cycler (MJ Research Inc.) with the following conditions: initial denaturation of 95° C. for 40 s, 5 cycles at 94° C. for 20 s, 67° C.-2° C./cycle for 20 s, 72° C. for 59 seconds+1 s/cycle, followed by 5 cycles at 94° C. for 25 s, 59° C.+1 ° C./cycle for 20 s, 72° C. for 1 minute and 7 s+1 s/cycle, followed by 20 cycles at 94° C. for 25 s, 63° C. for 20 s, 72° C. for 1 minute and 20 s+1 s/cycle, and a final incubation of 72° C. for minutes. The resulting ~1.35 kb PCR products were then gel purified from a 1.0% agarose gel using the QiaQuick Gel purification system (QIAGEN Inc., Chatsworth, Calif.), TA-cloned into pCR2.1 using the TOPO TA Cloning® kit (Invitrogen, San Diego, Calif., catalogue #K4550-40), and transformed into *E. coli* TOP10F' cells. Plasmid DNA was prepared using the Qiagen Plasmid Miniprep Kit (Qiagen Inc, Mississauga, ON, catalogue#12125. Insert sequence was obtained using fluorescent dideoxy-nucleotide sequencing and automated detection (ABI/Perkin Elmer, Foster City, Calif.).

Although the function of this alternative exon is unknown at the present time, it is not believed to be artifact because two identical independent RT-PCR clones of this alternative exon were obtained. The cDNA encoding for this isoform is set forth in SEQ ID NO: 4, with the predicted amino acid set forth in SEQ ID NO: 5, while the mature protein amino acid sequence is set forth in SEQ ID NO:

EXAMPLE 6

Molecular Cloning of hAIF

A BLAST search of the NCBI non-redundant database with the mAIF open reading frame revealed that the entire orthologous human AIF (hAIF) genomic DNA sequence was present in the database on PAC 179D3 (EMBL#Z81364, and EMBL#81370). Using the genomic sequence as a template, human AIF primers were designed that flanked the open reading frame, and are as follows:

```
sense primer # 1967-28:
5'-GAGAGGAAAGGGAAGGAGGAGGTC-3'      (SEQ ID NO: 24)

antisense primer# 1967-29:
5'-TTGCCAATTCCACTGTGGGGCTTC-3'.     (SEQ ID NO: 25)
```

Human AIF was cloned from human retinal cDNA. Human retinas were dissected from whole human eyes obtained from the EyeBank of Canada (Toronto, ON). Total RNA was prepared from human retinal tissue using TRIzo™Total RNA Isolation Reagent (Gibco BRL, Life Technologies Incorporated, Cat#15596-018) according to the manufacturer's instructions. First strand cDNA from total human retinal RNA was prepared using oligo-dT primers and the SuperscriptII first strand cDNA synthesis kit (Gibco BRL, Burlington, Ohio) according to the manufacturer's instructions. RT-PCR amplifications were performed using the Expand™ High Fidelity PCR system (Boehringer Mannheim GmbH, Germany Cat. No. 1732650) in a 50 µl volume containing 200 µM dNTPs, 0.5 µM of each of the foregoing primer, 0.10 mM Tris-HCl (pH 8.3), 1.5 mM $MgCl_2$, 50 mM KCl, 2 ng of oligo-dT primer human retinal cDNA, and 5 units of Expand™ Hi-Fi DNA polymerase (Boehringer Mannheim GmbH, Germany). The PCR reactions were amplified using a "Touch-down/Touch-up" annealing temperature protocol (Snow et al., *Biochem. Biophy. Res. Comm.*, 233:770-777 (1997) and Snow et al., *Gene.*, 206:247-253 (1998)) in a PTC-100 programmable thermal cycler (MJ Research Inc.) with the following conditions: initial denaturation of 95° C. for 40 s, 5 cycles at 94° C. for 20 s, 69° C.-2° C./cycle for 20 s, 72° C. for 2 minutes+1 s/cycle, followed by 5 cycles at 94° C. for 25 s, 61° C.+1° C./cycle for 20 s, 72° C. for 2 minutes and 33 s+1 s/cycle, and a final incubation of 72° C. for 5 minutes. The resulting ~1.9 kb PCR products were then gel purified from a 1.0% agarose gel using the QiaQuick Gel purification system (QIAGEN Inc., Chatsworth, Calif.), TA-cloned into pCR2.1 using the TOPO TA Cloning® kit (Invitrogen, San Diego, Calif., catalogue # K4550-40), and transformed into *E. coli* TOPIOF' cells. The Insert sequence was obtained using fluorescent dideoxy-nucleotide sequencing and automated detection (ABI/Perkin Elmer, Foster City, Calif.).

Two human AIF cDNA clones were sequenced: pCR2.1-hAIF-G.lower.14 (DNA#9812239) and pCR2.1-hAIF.E11 (DNA#9812238). Alignment of the hAIF cDNA clones (which were derived from independent RT-PCR reactions from human retina) with each other and with the hAIF genomic sequences from chromosome X (EMBL#Z81364) allowed a determination of the correct consensus sequence for the human AIF cDNA encompassing the open-reading frame.

The hAIF cDNA was predicted to encode a polypeptide of 613 amino acids with a predicted molecular weight of 66.824 kDa. Alignment of the human and mouse AIF polypeptides revealed that they are 92% identical. The cDNA encoding the hAIF is set forth in SEQ ID NO: 7, with the predicted hAIF amino acid sequence set forth in SEQ ID NO: 8, while the amino acid sequence of the mature hAIF protein is set forth in SEQ ID NO 9.

EXAMPLE 7

Identification of Alternative Isoforms of hAIF

A BLAST search of the N.C.B.I EST database with the region of mAIF containing the alternative exonic sequence identified a human EST (GenBank#H15605), which also contained an alternative coding region. The cDNA encoding for this alternative form of hAIF is set forth in SEQ ID NO: 10, with the predicted amino acid sequence set forth in SEQ ID NO: 11, while the amino acid sequence of the mature form is set forth in SEQ ID NO: 12.

Alignment of the two human AIF cDNA clones, which were sequenced, pCR2.1-hAIF-Glower.14 (DNA#9812239) and pCR2.1-hAIF.E11 (DNA#9812238), revealed that there was possible exon skipping in pCR2.1-hAIF-Glower.14 (DNA#9812239). This region of exon skipping corresponds exactly to the region where alternative splicing takes place in both the mouse and human AIF cDNAs. Such a discovery would means that the exon is either spliced out completely or is alternatively spliced to contain one of two exonic sequences in both mouse and human. The cDNA encoding for this second alternative form of hAIF is set forth in SEQ ID NO: 13, with the predicted amino acid sequence set forth in SEQ ID NO: 14, while the amino acid sequence of the mature form is set forth in SEQ ID NO: 15.

EXAMPLE 8

Construction of the Full-Length hAIF cDNA

The 100% sequence perfect human AIF cDNA was assembled from the two independent RT-PCT clones which were had sequenced as described herein. pCR2.1-hAIF-G-lower.14 (DNA#9812239), which exhibited exon skipping of the alternative exon in the N-terminus, was cut with 20 units of BamH1 in 1×Buffer B (Boehringer Mannheim) for 2 hours at 37° C., thus liberating a 1447 bp C-terminal fragment. The pCR2.1-hAIF.E11, which contained the sequence verified N-terminus of human AIF, was cut with 20 units of BamH1 in 1 X Buffer B (Boehringer Mannheim) for two hours, heat inactivated for 3 minutes at 85° C., cooled at room temperature for 20 minutes, diluted with 400 µl of 1×T.E. buffer in an UltraFreeg®-MC 30,000 NMWL filter unit (Millipore Cat#UFC3LTKNB) and centrifuged at 1960×g in an Eppendorf 5417C centrifuge for 6 minutes until an ~25 µl volume remained.

The 25 µl of the BamH1 cut pCR2.1-hAIF.E11 was then dephosphorylated with 0.1 units of Calf-Intestinal Alkal Phosphatase (Pharmacia Biotech Inc., catalogue#27-0620) for 30 minutes at 37° C. The reactions were then electrophoresed on a 1% agarose gel and the appropriate products were then cut from the gel and purified using the QiaQuick Gel purification system (QIAGEN Inc., Chatsworth, Calif.). The ligation was performed using the Rapid DNA Ligation Kit (Boehringer Mannheim Cat#1635379) according to the manufacturer's instructions. 7 µl of the ligation reaction were transformed into 80 µl of Epicurian Coli® Supercompetent XL1-Blue MR cells (Stratagene, La Jolla, Calif., catalogue#200229) according to the manufacturer's instructions.

EXAMPLE 9

Culturing Host Cells and Induction of Recombinant Protein

The pET32a expression vector (Novagen) containing the mouse AIF clone was transformed into Epicurian Coli O BL21 (DE3) competent (*Eschericia coli*, Stratagene) host cells as described in the Strategene instruction manual. The cells were plated onto LB-agar plates (9 mm plastic dishes) containing 50 ug carbenicillin (Sigma, ampacillin analogue) per mL of LB-agar (10 g tryptone, 5 g yeast extract, 5 g NaCl, 1 mL 1 N NaOH, 15 g agar, QS to 1L) and cultured overnight at 37° C. to select for transformed cells. A single colony of transformed cells was scraped off the plate and cultured in 50 mL of LB media agar (10 g tryptone, 5 g yeast extract, 5 g NaCl, 1 mL 1 N NaOH, QS to 1L) containing 50 ug/ml carbenicillin in (LB-carb) in a 500 mL baffled Erlenmeyer flask, with agitated at 225 rpm overnight at 37° C. When the cells reached an optical density of 1.0 (at 600 nm wave length, $O.D._{600}$) glycerol was added to the cell suspension to a final concentration of 15% and the cells were quick frozen in liquid nitrogen and stored at −80° C. This glycerol stock solution was used to inoculate media for all subsequent host cell cultures. 50 mL of LB-cab media in a 500 mL baffled Erlenmeyer flask was inoculated with a stab from the glycerol stock and the cell suspension was agitated at 225 rpm overnight at 37° C. The 50 mL culture was transferred to a 6 L glass Erlenmeyer flask and diluted to 1.5 L with fresh LB-carb media and the cells were grown at 37° C. with 200 rpm agitation in a shaker incubator. The cells were grown to an $O.D._{600}$=0.60 ($O.D._{600}$=0.1 is equivalent to about $10^8$ cells per mL of culture). At this density the incubator temperature was decreased to 22° C. and the cell cultures were allowed to cool to this temperature (with agitation) for ½ hour. After 1 hour at the lower growth temperature the cells reached $O.D._{600}$=0.8 and T7 polymerase expression was induced by adding Isopropyl-b-D-thiogalactopyranoside (IPTG, Sigma) to a final concentration of 0.2 mM (the IPTG drives the lacUV5 promoter upstream of the T7 polymerase gene in the DE3 lysogen, in turn the T7 polymerase drives the expression of thioredoxin-AIF fusion protein through the T7 promoter/lac enhancer in the pET32a vector). The IPTG-induced cells where cultured for 12 hours at 22° C. and harvested by centrifugation at 5,000×g for 15 minutes at 4° C. The harvested cell pellet (with a wet weight of approximately 5.0 g) was washed with 50 mL of PBS containing 1 dissolved protease inhibitor cocktail tablet (Boehringer Mannheim complete™, EDTA-free tablets) and pepstatin A (Boehringer Mannheim) at 2 ug/mL final concentration. The cells were repelleted and frozen on dry ice.

As a control, the pET32a vector alone (minus the AIF gene) was transformed into *Eschericia coli* host cells and expression of the thioredoxin tag alone was induced as described above for thioredoxin-tagged AIF.

EXAMPLE 10

Purification of Recombinant (Full Length) AIF Fusion-Protein

The frozen (thioredoxin-AIF (trx-AIF) fusion protein expressing) cell pellets were resuspended in 50 mL (10 mL per g wet pellet weight) of Lysis Buffer (25 mM HEPES-NaOH, pH 8.0, 100 mM NaCl, 10 mM β-mercaptoethanol, 20 mM Imidazole, 1 dissolved protease inhibitor cocktail tablet per 50 mL buffer, pepstatin A at 2 ug/mL and leupeptin at 2 ug/mL) and homogenized with a glass douce homgenizer followed by sonication using a ¼ inch probe attached to a 600 Watt Ultrasonic processor (Vibro-cell) set at 60% amplitude, 5 second pulses for 1 minute total time on ice. Unless otherwise stated all steps were done at 4° C. or on ice. The insoluble cellular debris was pelleted by centrifugation at 16,800×g for 30 minutes. The thioredoxin-AIF fusion protein remained in the centrifugation pellet (only a trace amount of trx-AIF was detected in the supernatant by Western blotting (using a monoclonal anti-trx antibody, see below for details on SDS-PAGE and blotting details). The supernatant was aspirated off of the pellet and the pellet was resuspended in 50 mL of Guanidine-HCl lysis buffer (25 mM HEPES-NaOH, pH 8.0, 6 M Guanidine-HCl, 10 mM Tris-HCl, 10 mM β-mercaptoethanol, 20 mM Imidazole, 1 dissolved protease inhibitor cocktail tablet per 50 mL buffer, pepstatin A at 2 ug/mL and leupeptin at 2 ug/mL) The pellet was resuspended in the buffer using a glass-Douce homogenizer and the homogenate was mixed for 15 minutes using a Neutator (Clay Adams®). The insoluble material was pelleted by centrifugation at 27,000×g for 30 minutes. The supernatant was passed over a 1.5×3.0 cm NiNTA-agarose superflow (QIAGEN) affinity column equilibrated in Guanidine-HCl lysis buffer. The column was loaded and resolved at a constant flow rate of 0.3 ml of solution per minute. The loaded column was washed with 50 mL (10 column bed volumes) of NiNTA-column wash buffer (25 mM HEPES-NaOH, pH 8.0, 6 M Guanidine-HCl, 10 mM Tris-HCl, 10 mM β-mercaptoethanol, 40 mM Imidazole). A 50 mL linear gradient was used to exchange the column buffer from Guanidine-HCl wash buffer to Urea buffer (25 mM HEPES-NaOH, pH 8.0, 6 M Urea, 10 mM Tris-HCl, 10 mM β-mercaptoethanol, 50 mM Imidazole).

The thioredoxin-AIF was then eluted off the NiNTA-agarose by passing 50 mL of NiNTA elution buffer (25 mM HEPES-NaOH, pH 8.0, 6 M Urea, 10 mM Tris-HCl, 10 mM β-mercaptoethanol, 50 mM EDTA, 1 dissolved protease inhibitor cocktail tablet per 50 mL buffer, pepstatin A at 2 ug/mL and leupeptin at 2 ug/mL). The collected elution fraction was diluted by adding 5 volumes (v/v) of dilution buffer (25 mM HEPES-NaOH, pH 8.0, 3 M Urea, 10 mM Tris-HCl, 10 mM µ-mercaptoethanol, 1 mM EDTA, 1 dissolved protease inhibitor cocktail tablet per 50 mL buffer, pepstatin A at 2 ug/mL and leupeptin at 2 ug/mL) and dialyzed in 1 L of dialysis buffer (25 mM HEPES-NaOH, pH 7.0, 5 mM β-mercaptoethanol, 1 mM EDTA and 10% glycerol) using 12-14 mwco Spectra/Por® membrane tubing. The dialysis buffer was changed every 4-6 hours, and a total of 6 L of dialysis buffer was used.

The dialyzed sample concentrated by ultrafiltration using an Amicon ultrafiltration pressure cell and a Amicon YM10 filter under 40 psi nitrogen gas to a final concentration between 1-4 mg/mL of protein as determined using the BioRad Bradford assay with IgG as a standard control (done as described by the manufacturer).

Thiorendoxin-AIF fusion protein was identified as a 98 KDa band by SDS-PAGE and Coomassie-blue staining using Novex 10-20% acrylamide-gradient Tris/Glycine gels and Novex gel apparatus. In order to confirm the identity of the 98 KDa band, resolved gels were blotted to PVDF membrane (Boehinger Mannheim), the membrane was blocked with blocking buffer (4% powdered skim milk, Carnation, 1% BSA, Sigma fraction V, 0.1% Tween 20 in Tris-buffered saline) and trx-AIF fusion protein was detected with either mouse anti-trx (3H8-E11) or rabbit anti-AIF (J53) antibodies followed by donkey/goat anti-mouse/rabbit IgG-HRP (horse-radish peroxidase) conjugates (Amersham). The HRP conjugate s were detected on Kodak X-omatic Blue XB-1 film using ECL western blotting detection reagents as outlined by the manufacturer (Amersham Life Sciences). A total of 1.0 mg of soluble, refolded protein was recovered per 1 L of cell culture grown.

A mammalian apoptosis-inducing factor (AIF) polypeptide, which suffices to induce apoptosis of isolated nuclei, has been identified and cloned. This ubiquitous factor with homology to bacterial oxidoreductases is normally confined to mitochondria and is released upon induction of apoptosis as a 57 kDa protein which translocates to the nucleus. Recombinant AIF causes isolated nuclei to undergo chromatin condensation and large scale (~50 kbp) DNA fragmentation. Moreover, it induces purified mitochondria to release cytochrome c and caspase-9. Microinjection of recombinant AIF protein into intact cells or transfection-enforced overexpression of AIF cause chromatin condensation, dissipation of the mitochondrial transmembrane potential ($DY_m$), and plasma membrane phosphatidylserine exposure. None of these effects is prevented by the broad spectrum caspase inhibitor Z-VAD.fmk. Overexpression of Bcl-2 prevents the release of AIF from mitochondria, yet has no effect on the capacity of AIF to induce nuclear apoptosis. These data, disclosed herein, establish AIF as a novel mitochondrial effector of apoptotic cell death. In view of the ability of AIF to induce apoptosis, administration of AIF (or analogs, homologs, or variants thereof that possess AIF-like activity) are expected to be helpful in treating and controlling a number of neoplastic diseases. Reduction of AIF polypeptide activity (by developing antagonists, inhibitors, use of neutralizing antibodies, or antisense molecules, all produced as described herein) should result in decreased apoptosis. Such activity might be desirable for the treatment of various neurodegenerative diseases that have been linked to the induction of apoptosis.

EXAMPLE 11

Identification of Binding Partners for AIF

In order to identify binding partners for mammalian AIF, a yeast two hybrid assay system may be used. The yeast two-hybrid assay is based on the fact that many eukaryotic transcriptional activators are composed of two physically separable, functionally independent domains. The yeast GAL4 transcriptional activator protein, for example, contains a DNA-binding domain (GAL4-DB), and a transcriptional activator domain (GAL4-TA). The GAL4-DB recognizes and binds to a sequence (UAS), in the upstream regions of GALA-responsive genes, while the GAL4-TA interacts with other components of the transcription machinery needed to initiate transcription. Both domains are required to activate a gene and, normally, the two domains are part of the same protein. However, if the two domains are physically separated (e.g. by way of recombinant DNA technology), and expressed in the same host cell, the GAL4-DB and TA peptides do not directly interact with each other and cannot activate responsive genes. (Ma et al. Cell 51:443-446 (1988)).

In a yeast two hybrid system, two different cloning vectors are used to generate separate fusions of these GAL4 domains that potentially interact with each other. The recombinant hybrid proteins (hybrid of GAL4 domain and a potential binding protein,) are co-expressed in yeast and are targeted to the yeast nucleus. If the non-GAL4-portions of the two types of hybrid interact with each other, the GAL4-DB will be tethered to GAL4-TA. As a result of this interaction, GAL4 transcriptional activator will be functionally reconstituted and will activate transcription of reporter genes having upstream GAL4 binding sites making protein-protein interaction phenotypically detectable. The yeast two-hybrid system has been used either to screen libraries for a gene(s) encoding a novel protein(s) that interacts with a known target protein or to test two known, previously cloned proteins for interaction. (Chien et al., *Proc. Natl. Acad. Sci.* 88:9578-9583 (1991), incorporated herein by reference).

To use the yeast two-hybrid system to isolate and identify novel AIF-binding proteins, a full length mammalian AIF DNA is cloned into the pAS-1 vector to generate a fusion between the target protein, AIF, and the DNA binding domain of GAL4. This createe the "bait", GAL4-AIF hybrid fusion protein. The yeast strain, (Y153), (Bai and Elledge, *Methods in Enzymol.* 273:331-347 (1996)) iss used for transformation and contains both HIS3 and lacZ reporter genes driven by promoters containing GAL4 binding sites, and is deleted for endogenous GAL4 (Bai et al. *Methods in Enzymol.* 273:331-347 (1996)). Yeast clones, transformed with pAS-1 GAL4-AIF, are screened for expression of the GAL4-AIF fusion protein by Western blot analysis of yeast lysates using either monoclonal or polyclonal anti-AIF antibodies (see above). The GAL4-AIF expressing clones are assayed for transcriptional activation of HIS3 gene based on their ability to grow on His-media, and are assayed for transcriptional activation of lacZ, by measuring b-gal activity using a colorimetric assay. In an attempt to screen for molecules that bind to AIF-protein "bait", a plasmid cDNA library from resting murine T-cells is obtained (Staudinger et al. *J. Biol. Chem.* 268: 4608-4611 (1993)). In this library, total cDNA obtained from resting T-cells is fused to the transcription activation domain of GAL4, GAL4-TA. Also, a mouse embryo GAL4-TA fusion library (Clontech, Palo Alto, Calif.), is used to transform yeast carrying GAL4-AIF DB fusion constructs. The cDNA libraries are transfected into yeast carrying the AIF-GAL4 DB fusion constructs and clones are selected on His-media supplemented with 20 mM aminotriazole. After 72 hours, nitrocellulose replicas of the transfected colonies are made and assayed for b-galactosidase activity directly by a method well known in the art. Sambrook et al., Supra. From the $6 \times 10^6$ clones screened from the T-cell library, and $3 \times 10^6$ clones screened from the mouse embryo library, forty two positive clones are picked and the cDNAs isolated. The isolated cDNAs are checked for insert size and introduced into a second strain of yeast (Y187)(Bai and Elledge, *Methods in Enzymol.* 273:331-347 (1996)). The purpose of this step is twofold, first the isolated cDNA can be tested for b-gal activity alone, or when mated with yeast carrying either GAL-AIF or GAL4 can be fused to other unrelated proteins. This eliminates any false positives. Matings between Y153 carrying the GAL4-AIF plasmid and Y187 carrying the GAL4-cDNA fusion are assayed for b-gal activity to confirm positive clones. Following this procedure, clones are eliminated as false positives. Clones are classified as false positives if they were positive for b-gal activity on their own or when mated with Y153 carrying the DNA binding domain alone.

The remaining clones isolated in this first round of screening, are classified as specifically interacting with AIF based on the following criteria: 1) yeast expressing both the cDNA and AIF hybrid proteins are able to grow on His media and are positive for b-gal activity; 2) the isolated cDNA transformed in Y187 are negative for activation of HIS3 and lacZ when mated to yeast carrying the GAL4 DNA binding domain alone; and 3) when mated with Y153, containing GAL4-AIF, the ability to transactivate both reporter constructs restored, but mating of the cDNA constructs with other GAL4 fusions did not result in activation of transcription.

Screening of a random primed library derived from mouse embryo (day 11.5) (commercially available from Clontech), is also carried out. Use of a random primed library allows the detection of AIF binding proteins, which require the amino terminal sequences for binding. Also, by using a library from a different tissue, cDNAs not represented in the T-cell library were detected. Finally, the repeat isolation of related molecules from two different libraries support the legitimacy of the interaction being detected.

Although the present invention has been described in terms of preferred embodiments, it is intended that the present invention encompass all modifications and variations that occur to those skilled in the art upon consideration of the disclosure herein, and in particular those embodiments that are within the broadest proper interpretation of the claims and their requirements. All literature cited herein is incorporated by reference.

Although the present invention has been described in terms of preferred embodiments, it is intended that the present invention encompass all modifications and variations that occur to those skilled in the art upon consideration of the disclosure herein, and in particular those embodiments that are within the broadest proper interpretation of the claims and their requirements.

All literature cited herein (scientific articles, U.S. patents, foreign patents, and published patent applications) is incorporated by reference.

What is claimed is:

1. An isolated purified human apoptosis-inducing factor, wherein the human apoptosis-inducing factor comprises the amino acid sequence set out in either SEQ ID NO: 8 or SEQ ID NO: 9.

2. A composition comprising an isolated purified mammalian apoptosis-inducing factor polypeptide that is not inhibited by Z-VAD fmk, wherein said apoptosis-inducing factor polypeptide comprises an amino acid sequence at least 95% identical to the amino acid sequence set forth in SEQ ID NO:8 or SEQ ID NO:9.

3. The composition according to claim 2, wherein the mammalian apoptosis-inducing factor is a human apoptosis-inducing factor, and wherein the human apoptosis-inducing factor comprises the amino acid sequence set out in either SEQ ID NO: 8 or SEQ ID NO: 9.

4. A composition comprising an isolated purified human apoptosis inducing factor, wherein the human apoptosis-inducing factor comprises the amino acid sequence set out in either SEQ ID NO: 8 or SEQ ID NO: 9, and a pharmaceutically acceptable carrier, diluent and/or adjuvant.

5. An isolated purified human apoptosis-inducing factor, wherein the human apoptosis-inducing factor comprises an amino acid sequence at least 95% identical to the amino acid sequence set forth in SEQ ID NO:8 or SEQ ID NO: 9.

6. The isolated purified human apoptosis-inducing factor of claim 1 or claim 5, wherein the human apoptosis-inducing factor is purified from the biological fluid of a human subject.

7. The isolated purified human apoptosis-inducing factor of claim 6, wherein the human biological fluid is selected from the group consisting of plasma, serum and urine.

8. The isolated purified human apoptosis-inducing factor of claim 6, wherein the human subject overexpresses human apoptosis-inducing factor.

9. The isolated purified human apoptosis-inducing factor of claim 6, wherein the human subject has a neurodegenerative disease.

10. The isolated purified human apoptosis-inducing factor of claim 9, wherein the neurodegenerative disease is selected from the group consisting of neurodegeneration due to stroke, Alzheimer's disease, Parkinson's disease and amyotrophic lateral sclerosis.

11. The isolated purified human apoptosis-inducing factor of claim 1, further comprising a water-soluble polymer.

12. The isolated purified human apoptosis inducing factor of claim 1, wherein the water-soluble polymer is selected from the group consisting of polyethylene glycol (PEG), monomethoxy-polyethylene glycol, a propylene glycol homopolymer, polypropylene oxide/ethylene oxide copolymer, a polyethylated polyol, polyvinyl pyrrolidone, poly-1, 3-dioxolane, poly-1, 3, 6, -trioxane, an ethylene/maleic anhydride copolymer, a homopolymer of polyamino acids, a copolymer of polyamino acids, poly(n-vinyl pyrrolidone)-polyethylene glycol, and polyvinyl alcohol.

* * * * *

SEQUENCE LISTING

```
<160> NUMBER OF SEQ ID NOS: 25

<210> SEQ ID NO 1
<211> LENGTH: 1932
<212> TYPE: DNA
<213> ORGANISM: Mus musculus
<220> FEATURE:
<221> NAME/KEY: CDS
<222> LOCATION: (1)..(1887)
<220> FEATURE:
<223> OTHER INFORMATION: mouse apoptosis-inducing factor (mAIF);
      mAIF-Gold.B1B

<400> SEQUENCE: 1 tgc gtg gaa gga aaa gga agg agc ggg agc ttc cga gga gtg atc gcc      48
Cys Val Glu Gly Lys Gly Arg Ser Gly Ser Phe Arg Gly Val Ile Ala
  1               5                  10                  15 gaa atg ttc cgg tgt gga ggc ctg gcg ggt gct ttc aag cag aaa ctg      96
Glu Met Phe Arg Cys Gly Gly Leu Ala Gly Ala Phe Lys Gln Lys Leu
                 20                  25                  30 gtg ccc ttg gtg cgg acg gtg tac gtc cag agg ccg aaa cag agg aac     144
Val Pro Leu Val Arg Thr Val Tyr Val Gln Arg Pro Lys Gln Arg Asn
             35                  40                  45 cgg ctt cca ggc aac ttg ttc cag caa tgg cgt gtt cct cta gaa ctc     192
Arg Leu Pro Gly Asn Leu Phe Gln Gln Trp Arg Val Pro Leu Glu Leu
         50                  55                  60 cag atg gca aga caa atg gct agc tct ggt tca tca ggg ggc aaa atg     240
Gln Met Ala Arg Gln Met Ala Ser Ser Gly Ser Ser Gly Gly Lys Met
 65                  70                  75                  80 gat aat tct gtg tta gtc ctt att gtg ggc tta tca aca ata gga gct     288
Asp Asn Ser Val Leu Val Leu Ile Val Gly Leu Ser Thr Ile Gly Ala
                 85                  90                  95 ggt gca tat gcc tac aaa act ata aaa gaa gac caa aaa aga tac aat     336
Gly Ala Tyr Ala Tyr Lys Thr Ile Lys Glu Asp Gln Lys Arg Tyr Asn
            100                 105                 110 gaa aga gtg atg gga tta gga ctg tcc cca gaa gag aaa cag aga aga     384
Glu Arg Val Met Gly Leu Gly Leu Ser Pro Glu Glu Lys Gln Arg Arg
        115                 120                 125 gcc att gcc tcc gct aca gag gga ggc tca gtt cct cag atc agg gca     432
Ala Ile Ala Ser Ala Thr Glu Gly Gly Ser Val Pro Gln Ile Arg Ala
```

-continued

|  |  |  |  |  |  |  |  |  |  |  |  |  |  |  |  |
|---|---|---|---|---|---|---|---|---|---|---|---|---|---|---|---|
|  |  | 130 |  |  |  | 135 |  |  |  | 140 |  |  |  |  |  |

```
cca agt cac gtc cct ttc ctg ctg att ggt gga ggg act gct gct ttt     480
Pro Ser His Val Pro Phe Leu Leu Ile Gly Gly Gly Thr Ala Ala Phe
145             150                 155                 160 gca gca gcc aga tcc atc cgg gct cgg gat cct ggg gcc agg gtc ctg     528
Ala Ala Ala Arg Ser Ile Arg Ala Arg Asp Pro Gly Ala Arg Val Leu
                165                 170                 175 att gta tct gaa gac cct gaa ctg cca tac atg cga cct cct ctt tca     576
Ile Val Ser Glu Asp Pro Glu Leu Pro Tyr Met Arg Pro Pro Leu Ser
            180                 185                 190 aaa gaa ttg tgg ttt tca gat gat cca aat gtc aca aag aca ctg caa     624
Lys Glu Leu Trp Phe Ser Asp Asp Pro Asn Val Thr Lys Thr Leu Gln
        195                 200                 205 ttc aga cag tgg aat gga aaa gag aga agc ata tat ttc cag cca cct     672
Phe Arg Gln Trp Asn Gly Lys Glu Arg Ser Ile Tyr Phe Gln Pro Pro
    210                 215                 220 tct ttc tat gtc tct gct cag gac ctg cct aat att gag aac ggt ggt     720
Ser Phe Tyr Val Ser Ala Gln Asp Leu Pro Asn Ile Glu Asn Gly Gly
225                 230                 235                 240 gtg gct gtc ctc act ggg aaa aag gta gta cat ctg gat gta aga ggc     768
Val Ala Val Leu Thr Gly Lys Lys Val Val His Leu Asp Val Arg Gly
                245                 250                 255 aac atg gtg aaa ctt aat gat ggc tct cag att acc ttt gaa aag tgc     816
Asn Met Val Lys Leu Asn Asp Gly Ser Gln Ile Thr Phe Glu Lys Cys
            260                 265                 270 ttg att gca acg gga ggc act cca aga agt ctg tct gcc atc gat agg     864
Leu Ile Ala Thr Gly Gly Thr Pro Arg Ser Leu Ser Ala Ile Asp Arg
        275                 280                 285 gct gga gca gag gtg aag agt aga aca aca ctt ttc agg aag att gga     912
Ala Gly Ala Glu Val Lys Ser Arg Thr Thr Leu Phe Arg Lys Ile Gly
    290                 295                 300 gat ttt aga gcc ttg gag aag atc tct cgg gag gtc aag tca att aca     960
Asp Phe Arg Ala Leu Glu Lys Ile Ser Arg Glu Val Lys Ser Ile Thr
305                 310                 315                 320 gtt atc ggc ggg ggc ttc ctt ggg agt gag ctg gcc tgt gct ctt ggc    1008
Val Ile Gly Gly Gly Phe Leu Gly Ser Glu Leu Ala Cys Ala Leu Gly
                325                 330                 335 aga aag tct caa gcc tcg ggc ata gaa gtg atc cag ctg ttc cct gag    1056
Arg Lys Ser Gln Ala Ser Gly Ile Glu Val Ile Gln Leu Phe Pro Glu
            340                 345                 350 aaa gga aat atg ggg aag atc ctt cct caa tac ctc agc aac tgg acc    1104
Lys Gly Asn Met Gly Lys Ile Leu Pro Gln Tyr Leu Ser Asn Trp Thr
        355                 360                 365 atg gaa aaa gtc aaa cga gag gga gtg aaa gtg atg ccc aat gca att    1152
Met Glu Lys Val Lys Arg Glu Gly Val Lys Val Met Pro Asn Ala Ile
    370                 375                 380 gta caa tca gtt gga gtc agc ggt ggc agg tta ctc att aag ctg aaa    1200
Val Gln Ser Val Gly Val Ser Gly Gly Arg Leu Leu Ile Lys Leu Lys
385                 390                 395                 400 gat gga agg aag gta gaa act gac cac ata gtg aca gct gtg ggc cta    1248
Asp Gly Arg Lys Val Glu Thr Asp His Ile Val Thr Ala Val Gly Leu
                405                 410                 415 gag ccc aat gtt gag ttg gcc aag act ggc gga ctg gaa ata gat tcc    1296
Glu Pro Asn Val Glu Leu Ala Lys Thr Gly Gly Leu Glu Ile Asp Ser
            420                 425                 430 gat ttt ggt ggc ttc cgg gta aat gca gaa ctc caa gca cgt tct aac    1344
Asp Phe Gly Gly Phe Arg Val Asn Ala Glu Leu Gln Ala Arg Ser Asn
        435                 440                 445 atc tgg gtg gca ggg gat gct gca tgc ttc tat gat ata aag ttg ggt    1392
```

```
Ile Trp Val Ala Gly Asp Ala Ala Cys Phe Tyr Asp Ile Lys Leu Gly
    450                 455                 460 cga agg cga gta gag cat cat gat cat gct gtt gtg agt gga aga ctg      1440
Arg Arg Arg Val Glu His His Asp His Ala Val Val Ser Gly Arg Leu
465                 470                 475                 480 gct gga gaa aac atg act gga gcc gct aag cca tac tgg cat cag tca      1488
Ala Gly Glu Asn Met Thr Gly Ala Ala Lys Pro Tyr Trp His Gln Ser
                485                 490                 495 atg ttc tgg agt gat ttg ggt cct gat gtc ggc tat gaa gct att ggt      1536
Met Phe Trp Ser Asp Leu Gly Pro Asp Val Gly Tyr Glu Ala Ile Gly
            500                 505                 510 ctg gtg gat agt agt ttg ccc aca gtt ggt gtt ttt gca aaa gca act      1584
Leu Val Asp Ser Ser Leu Pro Thr Val Gly Val Phe Ala Lys Ala Thr
        515                 520                 525 gca caa gac aac cca aaa tct gcc aca gag cag tca gga act ggt atc      1632
Ala Gln Asp Asn Pro Lys Ser Ala Thr Glu Gln Ser Gly Thr Gly Ile
    530                 535                 540 cgt tcg gag agt gag aca gag tca gaa gct tcg gaa atc aca att cct      1680
Arg Ser Glu Ser Glu Thr Glu Ser Glu Ala Ser Glu Ile Thr Ile Pro
545                 550                 555                 560 ccc agc gcc cct gca gtc cca cag gtc cct gtt gaa ggg gag gac tac      1728
Pro Ser Ala Pro Ala Val Pro Gln Val Pro Val Glu Gly Glu Asp Tyr
                565                 570                 575 ggc aaa ggt gtc atc ttc tac ctc agg gac aaa gtt gtg gtg ggg att      1776
Gly Lys Gly Val Ile Phe Tyr Leu Arg Asp Lys Val Val Val Gly Ile
            580                 585                 590 gtg cta tgg aac gtc ttt aac cga atg cca att gca agg aag atc att      1824
Val Leu Trp Asn Val Phe Asn Arg Met Pro Ile Ala Arg Lys Ile Ile
        595                 600                 605 aag gac ggt gag caa cat gaa gat ctc aat gaa gta gct aaa ctc ttc      1872
Lys Asp Gly Glu Gln His Glu Asp Leu Asn Glu Val Ala Lys Leu Phe
    610                 615                 620 aac att cat gaa gat tgaatcccaa tcgtggaata cacaagcact tttccatccc      1927
Asn Ile His Glu Asp
625 tggcg                                                                 1932

<210> SEQ ID NO 2
<211> LENGTH: 629
<212> TYPE: PRT
<213> ORGANISM: Mus musculus

<400> SEQUENCE: 2

Cys Val Glu Gly Lys Gly Arg Ser Gly Ser Phe Arg Gly Val Ile Ala
1               5                   10                  15

Glu Met Phe Arg Cys Gly Gly Leu Ala Gly Ala Phe Lys Gln Lys Leu
            20                  25                  30

Val Pro Leu Val Arg Thr Val Tyr Val Gln Arg Pro Lys Gln Arg Asn
        35                  40                  45

Arg Leu Pro Gly Asn Leu Phe Gln Gln Trp Arg Val Pro Leu Glu Leu
    50                  55                  60

Gln Met Ala Arg Gln Met Ala Ser Ser Gly Ser Gly Gly Lys Met
65                  70                  75                  80

Asp Asn Ser Val Leu Val Leu Ile Val Gly Leu Ser Thr Ile Gly Ala
                85                  90                  95

Gly Ala Tyr Ala Tyr Lys Thr Ile Lys Glu Asp Gln Lys Arg Tyr Asn
            100                 105                 110

Glu Arg Val Met Gly Leu Gly Leu Ser Pro Glu Glu Lys Gln Arg Arg
```

```
                115                 120                 125
Ala Ile Ala Ser Ala Thr Glu Gly Gly Ser Val Pro Gln Ile Arg Ala
        130                 135                 140

Pro Ser His Val Pro Phe Leu Leu Ile Gly Gly Thr Ala Ala Phe
145                 150                 155                 160

Ala Ala Ala Arg Ser Ile Arg Ala Arg Asp Pro Gly Ala Arg Val Leu
                    165                 170                 175

Ile Val Ser Glu Asp Pro Glu Leu Pro Tyr Met Arg Pro Pro Leu Ser
                180                 185                 190

Lys Glu Leu Trp Phe Ser Asp Asp Pro Asn Val Thr Lys Thr Leu Gln
                    195                 200                 205

Phe Arg Gln Trp Asn Gly Lys Glu Arg Ser Ile Tyr Phe Gln Pro Pro
        210                 215                 220

Ser Phe Tyr Val Ser Ala Gln Asp Leu Pro Asn Ile Glu Asn Gly Gly
225                 230                 235                 240

Val Ala Val Leu Thr Gly Lys Lys Val Val His Leu Asp Val Arg Gly
                    245                 250                 255

Asn Met Val Lys Leu Asn Asp Gly Ser Gln Ile Thr Phe Glu Lys Cys
                260                 265                 270

Leu Ile Ala Thr Gly Gly Thr Pro Arg Ser Leu Ser Ala Ile Asp Arg
        275                 280                 285

Ala Gly Ala Glu Val Lys Ser Arg Thr Thr Leu Phe Arg Lys Ile Gly
        290                 295                 300

Asp Phe Arg Ala Leu Glu Lys Ile Ser Arg Glu Val Lys Ser Ile Thr
305                 310                 315                 320

Val Ile Gly Gly Gly Phe Leu Gly Ser Glu Leu Ala Cys Ala Leu Gly
                    325                 330                 335

Arg Lys Ser Gln Ala Ser Gly Ile Glu Val Ile Gln Leu Phe Pro Glu
                340                 345                 350

Lys Gly Asn Met Gly Lys Ile Leu Pro Gln Tyr Leu Ser Asn Trp Thr
                    355                 360                 365

Met Glu Lys Val Lys Arg Glu Gly Val Lys Val Met Pro Asn Ala Ile
        370                 375                 380

Val Gln Ser Val Gly Val Ser Gly Gly Arg Leu Leu Ile Lys Leu Lys
385                 390                 395                 400

Asp Gly Arg Lys Val Glu Thr Asp His Ile Val Thr Ala Val Gly Leu
                    405                 410                 415

Glu Pro Asn Val Glu Leu Ala Lys Thr Gly Gly Leu Glu Ile Asp Ser
                420                 425                 430

Asp Phe Gly Gly Phe Arg Val Asn Ala Glu Leu Gln Ala Arg Ser Asn
        435                 440                 445

Ile Trp Val Ala Gly Asp Ala Ala Cys Phe Tyr Asp Ile Lys Leu Gly
        450                 455                 460

Arg Arg Arg Val Glu His His Asp His Ala Val Val Ser Gly Arg Leu
465                 470                 475                 480

Ala Gly Glu Asn Met Thr Gly Ala Ala Lys Pro Tyr Trp His Gln Ser
                    485                 490                 495

Met Phe Trp Ser Asp Leu Gly Pro Asp Val Gly Tyr Glu Ala Ile Gly
                500                 505                 510

Leu Val Asp Ser Ser Leu Pro Thr Val Gly Val Phe Ala Lys Ala Thr
        515                 520                 525

Ala Gln Asp Asn Pro Lys Ser Ala Thr Glu Gln Ser Gly Thr Gly Ile
        530                 535                 540
```

```
Arg Ser Glu Ser Glu Thr Glu Ser Glu Ala Ser Glu Ile Thr Ile Pro
545                 550                 555                 560

Pro Ser Ala Pro Ala Val Pro Gln Val Pro Val Glu Gly Glu Asp Tyr
                565                 570                 575

Gly Lys Gly Val Ile Phe Tyr Leu Arg Asp Lys Val Val Gly Ile
            580                 585                 590

Val Leu Trp Asn Val Phe Asn Arg Met Pro Ile Ala Arg Lys Ile Ile
        595                 600                 605

Lys Asp Gly Glu Gln His Glu Asp Leu Asn Glu Val Ala Lys Leu Phe
    610                 615                 620

Asn Ile His Glu Asp
625

<210> SEQ ID NO 3
<211> LENGTH: 612
<212> TYPE: PRT
<213> ORGANISM: Mus musculus
<220> FEATURE:
<223> OTHER INFORMATION: mouse apoptosis-inducing factor (mAIF);
      mAIF-Gold.B1B; mature polypeptide

<400> SEQUENCE: 3

Met Phe Arg Cys Gly Gly Leu Ala Gly Ala Phe Lys Gln Lys Leu Val
1               5                   10                  15

Pro Leu Val Arg Thr Val Tyr Val Gln Arg Pro Lys Gln Arg Asn Arg
            20                  25                  30

Leu Pro Gly Asn Leu Phe Gln Gln Trp Arg Val Pro Leu Glu Leu Gln
        35                  40                  45

Met Ala Arg Gln Met Ala Ser Ser Gly Ser Ser Gly Gly Lys Met Asp
    50                  55                  60

Asn Ser Val Leu Val Leu Ile Val Gly Leu Ser Thr Ile Gly Ala Gly
65                  70                  75                  80

Ala Tyr Ala Tyr Lys Thr Ile Lys Glu Asp Gln Lys Arg Tyr Asn Glu
                85                  90                  95

Arg Val Met Gly Leu Gly Leu Ser Pro Glu Glu Lys Gln Arg Arg Ala
            100                 105                 110

Ile Ala Ser Ala Thr Glu Gly Gly Ser Val Pro Gln Ile Arg Ala Pro
        115                 120                 125

Ser His Val Pro Phe Leu Leu Ile Gly Gly Gly Thr Ala Ala Phe Ala
    130                 135                 140

Ala Ala Arg Ser Ile Arg Ala Arg Asp Pro Gly Ala Arg Val Leu Ile
145                 150                 155                 160

Val Ser Glu Asp Pro Glu Leu Pro Tyr Met Arg Pro Pro Leu Ser Lys
                165                 170                 175

Glu Leu Trp Phe Ser Asp Asp Pro Asn Val Thr Lys Thr Leu Gln Phe
            180                 185                 190

Arg Gln Trp Asn Gly Lys Glu Arg Ser Ile Tyr Phe Gln Pro Pro Ser
        195                 200                 205

Phe Tyr Val Ser Ala Gln Asp Leu Pro Asn Ile Glu Asn Gly Gly Val
    210                 215                 220

Ala Val Leu Thr Gly Lys Lys Val Val His Leu Asp Val Arg Gly Asn
225                 230                 235                 240

Met Val Lys Leu Asn Asp Gly Ser Gln Ile Thr Phe Glu Lys Cys Leu
                245                 250                 255

Ile Ala Thr Gly Gly Thr Pro Arg Ser Leu Ser Ala Ile Asp Arg Ala
```

-continued

```
                260                 265                 270
Gly Ala Glu Val Lys Ser Arg Thr Thr Leu Phe Arg Lys Ile Gly Asp
            275                 280                 285

Phe Arg Ala Leu Glu Lys Ile Ser Arg Glu Val Lys Ser Ile Thr Val
290                 295                 300

Ile Gly Gly Gly Phe Leu Gly Ser Glu Leu Ala Cys Ala Leu Gly Arg
305                 310                 315                 320

Lys Ser Gln Ala Ser Gly Ile Glu Val Ile Gln Leu Phe Pro Glu Lys
            325                 330                 335

Gly Asn Met Gly Lys Ile Leu Pro Gln Tyr Leu Ser Asn Trp Thr Met
            340                 345                 350

Glu Lys Val Lys Arg Glu Gly Val Lys Val Met Pro Asn Ala Ile Val
            355                 360                 365

Gln Ser Val Gly Val Ser Gly Arg Leu Leu Ile Lys Leu Lys Asp
            370                 375                 380

Gly Arg Lys Val Glu Thr Asp His Ile Val Thr Ala Val Gly Leu Glu
385                 390                 395                 400

Pro Asn Val Glu Leu Ala Lys Thr Gly Gly Leu Glu Ile Asp Ser Asp
            405                 410                 415

Phe Gly Gly Phe Arg Val Asn Ala Glu Leu Gln Ala Arg Ser Asn Ile
            420                 425                 430

Trp Val Ala Gly Asp Ala Ala Cys Phe Tyr Asp Ile Lys Leu Gly Arg
            435                 440                 445

Arg Arg Val Glu His His Asp His Ala Val Val Ser Gly Arg Leu Ala
450                 455                 460

Gly Glu Asn Met Thr Gly Ala Ala Lys Pro Tyr Trp His Gln Ser Met
465                 470                 475                 480

Phe Trp Ser Asp Leu Gly Pro Asp Val Gly Tyr Glu Ala Ile Gly Leu
            485                 490                 495

Val Asp Ser Ser Leu Pro Thr Val Gly Val Phe Ala Lys Ala Thr Ala
            500                 505                 510

Gln Asp Asn Pro Lys Ser Ala Thr Glu Gln Ser Gly Thr Gly Ile Arg
            515                 520                 525

Ser Glu Ser Glu Thr Glu Ser Glu Ala Ser Glu Ile Thr Ile Pro Pro
530                 535                 540

Ser Ala Pro Ala Val Pro Gln Val Pro Val Glu Gly Glu Asp Tyr Gly
545                 550                 555                 560

Lys Gly Val Ile Phe Tyr Leu Arg Asp Lys Val Val Val Gly Ile Val
            565                 570                 575

Leu Trp Asn Val Phe Asn Arg Met Pro Ile Ala Arg Lys Ile Ile Lys
            580                 585                 590

Asp Gly Glu Gln His Glu Asp Leu Asn Glu Val Ala Lys Leu Phe Asn
            595                 600                 605

Ile His Glu Asp
    610

<210> SEQ ID NO 4
<211> LENGTH: 1920
<212> TYPE: DNA
<213> ORGANISM: Mus musculus
<220> FEATURE:
<221> NAME/KEY: CDS
<222> LOCATION: (1)..(1875)
<220> FEATURE:
<223> OTHER INFORMATION: mouse apoptosis-inducing factor (mAIF isoform);
      mAIF-alt-exon-Gold
```

<400> SEQUENCE: 4

```
tgc gtg gaa gga aaa gga agg agc ggg agc ttc cga gga gtg atc gcc         48
Cys Val Glu Gly Lys Gly Arg Ser Gly Ser Phe Arg Gly Val Ile Ala
 1               5                  10                  15 gaa atg ttc cgg tgt gga ggc ctg gcg ggt gct ttc aag cag aaa ctg         96
Glu Met Phe Arg Cys Gly Gly Leu Ala Gly Ala Phe Lys Gln Lys Leu
            20                  25                  30 gtg ccc ttg gtg cgg acg gtg tac gtc cag agg ccg aaa cag agg aac        144
Val Pro Leu Val Arg Thr Val Tyr Val Gln Arg Pro Lys Gln Arg Asn
        35                  40                  45 cgg ctt cca gtt gtg cag tgt cat ctc cta gga tcc cct tct aga aca        192
Arg Leu Pro Val Val Gln Cys His Leu Leu Gly Ser Pro Ser Arg Thr
    50                  55                  60 cta gcg tct gca ggt gct tct ggg aaa gat ggc agc agc cta gta tac        240
Leu Ala Ser Ala Gly Ala Ser Gly Lys Asp Gly Ser Ser Leu Val Tyr
 65                  70                  75                  80 ttc tta att gta gga gca aca gtg act ggg gca gga att tat tat gcc        288
Phe Leu Ile Val Gly Ala Thr Val Thr Gly Ala Gly Ile Tyr Tyr Ala
                85                  90                  95 tac aaa act ata aaa gaa gac caa aaa aga tac aat gaa aga gtg atg        336
Tyr Lys Thr Ile Lys Glu Asp Gln Lys Arg Tyr Asn Glu Arg Val Met
            100                 105                 110 gga tta gga ctg tcc cca gaa gag aaa cag aga aga gcc att gcc tcc        384
Gly Leu Gly Leu Ser Pro Glu Glu Lys Gln Arg Arg Ala Ile Ala Ser
        115                 120                 125 gct aca gag gga ggc tca gtt cct cag atc agg gca cca agt cac gtc        432
Ala Thr Glu Gly Gly Ser Val Pro Gln Ile Arg Ala Pro Ser His Val
    130                 135                 140 cct ttc ctg ctg att ggt gga ggg act gct gct ttt gca gca gcc aga        480
Pro Phe Leu Leu Ile Gly Gly Gly Thr Ala Ala Phe Ala Ala Ala Arg
145                 150                 155                 160 tcc atc cgg gct cgg gat cct ggg gcc agg gtc ctg att gta tct gaa        528
Ser Ile Arg Ala Arg Asp Pro Gly Ala Arg Val Leu Ile Val Ser Glu
                165                 170                 175 gac cct gaa ctg cca tac atg cga cct cct ctt tca aaa gaa ttg tgg        576
Asp Pro Glu Leu Pro Tyr Met Arg Pro Pro Leu Ser Lys Glu Leu Trp
            180                 185                 190 ttt tca gat gat cca aat gtc aca aag aca ctg caa ttc aga cag tgg        624
Phe Ser Asp Asp Pro Asn Val Thr Lys Thr Leu Gln Phe Arg Gln Trp
        195                 200                 205 aat gga aaa gag aga agc ata tat ttc cag cca cct tct ttc tat gtc        672
Asn Gly Lys Glu Arg Ser Ile Tyr Phe Gln Pro Pro Ser Phe Tyr Val
    210                 215                 220 tct gct cag gac ctg cct aat att gag aac ggt ggt gtg gct gtc ctc        720
Ser Ala Gln Asp Leu Pro Asn Ile Glu Asn Gly Gly Val Ala Val Leu
225                 230                 235                 240 act ggg aaa aag gta gta cat ctg gat gta aga ggc aac atg gtg aaa        768
Thr Gly Lys Lys Val Val His Leu Asp Val Arg Gly Asn Met Val Lys
                245                 250                 255 ctt aat gat ggc tct cag att acc ttt gaa aag tgc ttg att gca acg        816
Leu Asn Asp Gly Ser Gln Ile Thr Phe Glu Lys Cys Leu Ile Ala Thr
            260                 265                 270 gga ggc act cca aga agt ctg tct gcc atc gat agg gct gga gca gag        864
Gly Gly Thr Pro Arg Ser Leu Ser Ala Ile Asp Arg Ala Gly Ala Glu
        275                 280                 285 gtg aag agt aga aca aca ctt ttc agg aag att gga gat ttt aga gcc        912
Val Lys Ser Arg Thr Thr Leu Phe Arg Lys Ile Gly Asp Phe Arg Ala
    290                 295                 300
```

```
ttg gag aag atc tct cgg gag gtc aag tca att aca gtt atc ggc ggg     960
Leu Glu Lys Ile Ser Arg Glu Val Lys Ser Ile Thr Val Ile Gly Gly
305                 310                 315                 320 ggc ttc ctt ggg agt gag ctg gcc tgt gct ctt ggc aga aag tct caa    1008
Gly Phe Leu Gly Ser Glu Leu Ala Cys Ala Leu Gly Arg Lys Ser Gln
                325                 330                 335 gcc tcg ggc ata gaa gtg atc cag ctg ttc cct gag aaa gga aat atg    1056
Ala Ser Gly Ile Glu Val Ile Gln Leu Phe Pro Glu Lys Gly Asn Met
            340                 345                 350 ggg aag atc ctt cct caa tac ctc agc aac tgg acc atg gaa aaa gtc    1104
Gly Lys Ile Leu Pro Gln Tyr Leu Ser Asn Trp Thr Met Glu Lys Val
        355                 360                 365 aaa cga gag gga gtg aaa gtg atg ccc aat gca att gta caa tca gtt    1152
Lys Arg Glu Gly Val Lys Val Met Pro Asn Ala Ile Val Gln Ser Val
    370                 375                 380 gga gtc agc ggt ggc agg tta ctc att aag ctg aaa gat gga agg aag    1200
Gly Val Ser Gly Gly Arg Leu Leu Ile Lys Leu Lys Asp Gly Arg Lys
385                 390                 395                 400 gta gaa act gac cac ata gtg aca gct gtg ggc cta gag ccc aat gtt    1248
Val Glu Thr Asp His Ile Val Thr Ala Val Gly Leu Glu Pro Asn Val
                405                 410                 415 gag ttg gcc aag act ggc gga ctg gaa ata gat tcc gat ttt ggt ggc    1296
Glu Leu Ala Lys Thr Gly Gly Leu Glu Ile Asp Ser Asp Phe Gly Gly
            420                 425                 430 ttc cgg gta aat gca gaa ctc caa gca cgt tct aac atc tgg gtg gca    1344
Phe Arg Val Asn Ala Glu Leu Gln Ala Arg Ser Asn Ile Trp Val Ala
        435                 440                 445 ggg gat gct gca tgc ttc tat gat ata aag ttg ggt cga agg cga gta    1392
Gly Asp Ala Ala Cys Phe Tyr Asp Ile Lys Leu Gly Arg Arg Arg Val
    450                 455                 460 gag cat cat gat cat gct gtt gtg agt gga aga ctg gct gga gaa aac    1440
Glu His His Asp His Ala Val Val Ser Gly Arg Leu Ala Gly Glu Asn
465                 470                 475                 480 atg act gga gcc gct aag cca tac tgg cat cag tca atg ttc tgg agt    1488
Met Thr Gly Ala Ala Lys Pro Tyr Trp His Gln Ser Met Phe Trp Ser
                485                 490                 495 gat ttg ggt cct gat gtc ggc tat gaa gct att ggt ctg gtg gat agt    1536
Asp Leu Gly Pro Asp Val Gly Tyr Glu Ala Ile Gly Leu Val Asp Ser
            500                 505                 510 agt ttg ccc aca gtt ggt gtt ttt gca aaa gca act gca caa gac aac    1584
Ser Leu Pro Thr Val Gly Val Phe Ala Lys Ala Thr Ala Gln Asp Asn
        515                 520                 525 cca aaa tct gcc aca gag cag tca gga act ggt atc cgt tcg gag agt    1632
Pro Lys Ser Ala Thr Glu Gln Ser Gly Thr Gly Ile Arg Ser Glu Ser
    530                 535                 540 gag aca gag tca gaa gct tcg gaa atc aca att cct ccc agc gcc cct    1680
Glu Thr Glu Ser Glu Ala Ser Glu Ile Thr Ile Pro Pro Ser Ala Pro
545                 550                 555                 560 gca gtc cca cag gtc cct gtt gaa ggg gag gac tac ggc aaa ggt gtc    1728
Ala Val Pro Gln Val Pro Val Glu Gly Glu Asp Tyr Gly Lys Gly Val
                565                 570                 575 atc ttc tac ctc agg gac aaa gtt gtg gtg ggg att gtg cta tgg aac    1776
Ile Phe Tyr Leu Arg Asp Lys Val Val Val Gly Ile Val Leu Trp Asn
            580                 585                 590 gtc ttt aac cga atg cca att gca agg aag atc att aag gac ggt gag    1824
Val Phe Asn Arg Met Pro Ile Ala Arg Lys Ile Ile Lys Asp Gly Glu
        595                 600                 605 caa cat gaa gat ctc aat gaa gta gct aaa ctc ttc aac att cat gaa    1872
Gln His Glu Asp Leu Asn Glu Val Ala Lys Leu Phe Asn Ile His Glu
    610                 615                 620
```

```
gat tgaatcccaa tcgtggaata cacaagcact tttccatccc tggcg                    1920
Asp
625

<210> SEQ ID NO 5
<211> LENGTH: 625
<212> TYPE: PRT
<213> ORGANISM: Mus musculus

<400> SEQUENCE: 5

Cys Val Glu Gly Lys Gly Arg Ser Gly Ser Phe Arg Gly Val Ile Ala
  1               5                  10                  15

Glu Met Phe Arg Cys Gly Gly Leu Ala Gly Ala Phe Lys Gln Lys Leu
                 20                  25                  30

Val Pro Leu Val Arg Thr Val Tyr Val Gln Arg Pro Lys Gln Arg Asn
             35                  40                  45

Arg Leu Pro Val Gln Cys His Leu Leu Gly Ser Pro Ser Arg Thr
         50                  55                  60

Leu Ala Ser Ala Gly Ala Ser Gly Lys Asp Gly Ser Ser Leu Val Tyr
 65                  70                  75                  80

Phe Leu Ile Val Gly Ala Thr Val Thr Gly Ala Gly Ile Tyr Tyr Ala
                 85                  90                  95

Tyr Lys Thr Ile Lys Glu Asp Gln Lys Arg Tyr Asn Glu Arg Val Met
            100                 105                 110

Gly Leu Gly Leu Ser Pro Glu Glu Lys Gln Arg Arg Ala Ile Ala Ser
        115                 120                 125

Ala Thr Glu Gly Gly Ser Val Pro Gln Ile Arg Ala Pro Ser His Val
    130                 135                 140

Pro Phe Leu Leu Ile Gly Gly Thr Ala Ala Phe Ala Ala Ala Arg
145                 150                 155                 160

Ser Ile Arg Ala Arg Asp Pro Gly Ala Arg Val Leu Ile Val Ser Glu
                165                 170                 175

Asp Pro Glu Leu Pro Tyr Met Arg Pro Pro Leu Ser Lys Glu Leu Trp
            180                 185                 190

Phe Ser Asp Asp Pro Asn Val Thr Lys Thr Leu Gln Phe Arg Gln Trp
        195                 200                 205

Asn Gly Lys Glu Arg Ser Ile Tyr Phe Gln Pro Ser Phe Tyr Val
    210                 215                 220

Ser Ala Gln Asp Leu Pro Asn Ile Glu Asn Gly Gly Val Ala Val Leu
225                 230                 235                 240

Thr Gly Lys Lys Val His Leu Asp Val Arg Gly Asn Met Val Lys
                245                 250                 255

Leu Asn Asp Gly Ser Gln Ile Thr Phe Glu Lys Cys Leu Ile Ala Thr
            260                 265                 270

Gly Gly Thr Pro Arg Ser Leu Ser Ala Ile Asp Arg Ala Gly Ala Glu
        275                 280                 285

Val Lys Ser Arg Thr Thr Leu Phe Arg Lys Ile Gly Asp Phe Arg Ala
    290                 295                 300

Leu Glu Lys Ile Ser Arg Glu Val Lys Ser Ile Thr Val Ile Gly Gly
305                 310                 315                 320

Gly Phe Leu Gly Ser Glu Leu Ala Cys Ala Leu Gly Arg Lys Ser Gln
                325                 330                 335

Ala Ser Gly Ile Glu Val Ile Gln Leu Phe Pro Glu Lys Gly Asn Met
            340                 345                 350
```

```
Gly Lys Ile Leu Pro Gln Tyr Leu Ser Asn Trp Thr Met Glu Lys Val
        355                 360                 365
Lys Arg Glu Gly Val Lys Val Met Pro Asn Ala Ile Val Gln Ser Val
370                 375                 380
Gly Val Ser Gly Arg Leu Leu Ile Lys Leu Lys Asp Gly Arg Lys
385                 390                 395                 400
Val Glu Thr Asp His Ile Val Thr Ala Val Gly Leu Glu Pro Asn Val
                405                 410                 415
Glu Leu Ala Lys Thr Gly Gly Leu Glu Ile Asp Ser Asp Phe Gly Gly
            420                 425                 430
Phe Arg Val Asn Ala Glu Leu Gln Ala Arg Ser Asn Ile Trp Val Ala
        435                 440                 445
Gly Asp Ala Ala Cys Phe Tyr Asp Ile Lys Leu Gly Arg Arg Arg Val
    450                 455                 460
Glu His His Asp His Ala Val Val Ser Gly Arg Leu Ala Gly Glu Asn
465                 470                 475                 480
Met Thr Gly Ala Ala Lys Pro Tyr Trp His Gln Ser Met Phe Trp Ser
                485                 490                 495
Asp Leu Gly Pro Asp Val Gly Tyr Glu Ala Ile Gly Leu Val Asp Ser
            500                 505                 510
Ser Leu Pro Thr Val Gly Val Phe Ala Lys Ala Thr Ala Gln Asp Asn
        515                 520                 525
Pro Lys Ser Ala Thr Glu Gln Ser Gly Thr Gly Ile Arg Ser Glu Ser
    530                 535                 540
Glu Thr Glu Ser Glu Ala Ser Glu Ile Thr Ile Pro Pro Ser Ala Pro
545                 550                 555                 560
Ala Val Pro Gln Val Pro Val Glu Gly Glu Asp Tyr Gly Lys Gly Val
                565                 570                 575
Ile Phe Tyr Leu Arg Asp Lys Val Val Val Gly Ile Val Leu Trp Asn
            580                 585                 590
Val Phe Asn Arg Met Pro Ile Ala Arg Lys Ile Ile Lys Asp Gly Glu
        595                 600                 605
Gln His Glu Asp Leu Asn Glu Val Ala Lys Leu Phe Asn Ile His Glu
    610                 615                 620
Asp
625

<210> SEQ ID NO 6
<211> LENGTH: 608
<212> TYPE: PRT
<213> ORGANISM: Mus musculus
<220> FEATURE:
<223> OTHER INFORMATION: mouse apoptosis-inducing factor (mAIF isoform);
      mAIF-alt-exon-Gold; mature polypeptide

<400> SEQUENCE: 6

Met Phe Arg Cys Gly Gly Leu Ala Gly Ala Phe Lys Gln Lys Leu Val
1               5                   10                  15
Pro Leu Val Arg Thr Val Tyr Val Gln Arg Pro Lys Gln Arg Asn Arg
            20                  25                  30
Leu Pro Val Val Gln Cys His Leu Leu Gly Ser Pro Ser Arg Thr Leu
        35                  40                  45
Ala Ser Ala Gly Ala Ser Gly Lys Asp Gly Ser Ser Leu Val Tyr Phe
    50                  55                  60
Leu Ile Val Gly Ala Thr Val Thr Gly Ala Gly Ile Tyr Tyr Ala Tyr
65                  70                  75                  80
```

-continued

```
Lys Thr Ile Lys Glu Asp Gln Lys Arg Tyr Asn Glu Arg Val Met Gly
                85                  90                  95
Leu Gly Leu Ser Pro Glu Lys Gln Arg Arg Ala Ile Ala Ser Ala
            100                 105                 110
Thr Glu Gly Gly Ser Val Pro Gln Ile Arg Ala Pro Ser His Val Pro
            115                 120                 125
Phe Leu Leu Ile Gly Gly Thr Ala Ala Phe Ala Ala Ala Arg Ser
130                 135                 140
Ile Arg Ala Arg Asp Pro Gly Ala Arg Val Leu Ile Val Ser Glu Asp
145                 150                 155                 160
Pro Glu Leu Pro Tyr Met Arg Pro Leu Ser Lys Glu Leu Trp Phe
            165                 170                 175
Ser Asp Asp Pro Asn Val Thr Lys Thr Leu Gln Phe Arg Gln Trp Asn
            180                 185                 190
Gly Lys Glu Arg Ser Ile Tyr Phe Gln Pro Pro Ser Phe Tyr Val Ser
            195                 200                 205
Ala Gln Asp Leu Pro Asn Ile Glu Asn Gly Gly Val Ala Val Leu Thr
    210                 215                 220
Gly Lys Lys Val Val His Leu Asp Val Arg Gly Asn Met Val Lys Leu
225                 230                 235                 240
Asn Asp Gly Ser Gln Ile Thr Phe Glu Lys Cys Leu Ile Ala Thr Gly
                245                 250                 255
Gly Thr Pro Arg Ser Leu Ser Ala Ile Asp Arg Ala Gly Ala Glu Val
            260                 265                 270
Lys Ser Arg Thr Thr Leu Phe Arg Lys Ile Gly Asp Phe Arg Ala Leu
        275                 280                 285
Glu Lys Ile Ser Arg Glu Val Lys Ser Ile Thr Val Ile Gly Gly Gly
    290                 295                 300
Phe Leu Gly Ser Glu Leu Ala Cys Ala Leu Gly Arg Lys Ser Gln Ala
305                 310                 315                 320
Ser Gly Ile Glu Val Ile Gln Leu Phe Pro Glu Lys Gly Asn Met Gly
                325                 330                 335
Lys Ile Leu Pro Gln Tyr Leu Ser Asn Trp Thr Met Glu Lys Val Lys
            340                 345                 350
Arg Glu Gly Val Lys Val Met Pro Asn Ala Ile Val Gln Ser Val Gly
        355                 360                 365
Val Ser Gly Gly Arg Leu Leu Ile Lys Leu Lys Asp Gly Arg Lys Val
    370                 375                 380
Glu Thr Asp His Ile Val Thr Ala Val Gly Leu Glu Pro Asn Val Glu
385                 390                 395                 400
Leu Ala Lys Thr Gly Gly Leu Glu Ile Asp Ser Asp Phe Gly Gly Phe
                405                 410                 415
Arg Val Asn Ala Glu Leu Gln Ala Arg Ser Asn Ile Trp Val Ala Gly
            420                 425                 430
Asp Ala Ala Cys Phe Tyr Asp Ile Lys Leu Gly Arg Arg Arg Val Glu
        435                 440                 445
His His Asp His Ala Val Val Ser Gly Arg Leu Ala Gly Glu Asn Met
    450                 455                 460
Thr Gly Ala Ala Lys Pro Tyr Trp His Gln Ser Met Phe Trp Ser Asp
465                 470                 475                 480
Leu Gly Pro Asp Val Gly Tyr Glu Ala Ile Gly Leu Val Asp Ser Ser
                485                 490                 495
```

-continued

```
Leu Pro Thr Val Gly Val Phe Ala Lys Ala Thr Ala Gln Asp Asn Pro
            500                 505                 510

Lys Ser Ala Thr Glu Gln Ser Gly Thr Gly Ile Arg Ser Glu Ser Glu
        515                 520                 525

Thr Glu Ser Glu Ala Ser Glu Ile Thr Ile Pro Pro Ser Ala Pro Ala
    530                 535                 540

Val Pro Gln Val Pro Val Glu Gly Glu Asp Tyr Gly Lys Gly Val Ile
545                 550                 555                 560

Phe Tyr Leu Arg Asp Lys Val Val Gly Ile Val Leu Trp Asn Val
                565                 570                 575

Phe Asn Arg Met Pro Ile Ala Arg Lys Ile Ile Lys Asp Gly Glu Gln
            580                 585                 590

His Glu Asp Leu Asn Glu Val Ala Lys Leu Phe Asn Ile His Glu Asp
        595                 600                 605

<210> SEQ ID NO 7
<211> LENGTH: 1906
<212> TYPE: DNA
<213> ORGANISM: Homo sapiens
<220> FEATURE:
<221> NAME/KEY: CDS
<222> LOCATION: (1)..(1881)
<220> FEATURE:
<223> OTHER INFORMATION: human apoptosis-inducing factor (hAIF);
      hAIF-Gold

<400> SEQUENCE: 7 aga gga aag gga agg agg agg tcc cga ata gcg gtc gcc gaa atg ttc     48
Arg Gly Lys Gly Arg Arg Arg Ser Arg Ile Ala Val Ala Glu Met Phe
  1               5                  10                  15 cgg tgt gga ggc ctg gcg gcg ggt gct ttg aag cag aag ctg gtg ccc     96
Arg Cys Gly Gly Leu Ala Ala Gly Ala Leu Lys Gln Lys Leu Val Pro
             20                  25                  30 ttg gtg cgg acc gtg tgc gtc cga agc ccg agg cag agg aac cgg ctc    144
Leu Val Arg Thr Val Cys Val Arg Ser Pro Arg Gln Arg Asn Arg Leu
         35                  40                  45 cca ggc aac ttg ttc cag cga tgg cat gtt cct cta gaa ctc cag atg    192
Pro Gly Asn Leu Phe Gln Arg Trp His Val Pro Leu Glu Leu Gln Met
     50                  55                  60 aca aga caa atg gct agc tct ggt gca tca ggg ggc aaa atc gat aat    240
Thr Arg Gln Met Ala Ser Ser Gly Ala Ser Gly Gly Lys Ile Asp Asn
 65                  70                  75                  80 tct gtg tta gtc ctt att gtg ggc tta tca aca gta gga gct ggt gcc    288
Ser Val Leu Val Leu Ile Val Gly Leu Ser Thr Val Gly Ala Gly Ala
                 85                  90                  95 tat gcc tac aag act atg aaa gag gac gaa aaa aga tac aat gaa aga    336
Tyr Ala Tyr Lys Thr Met Lys Glu Asp Glu Lys Arg Tyr Asn Glu Arg
            100                 105                 110 att tca ggg tta ggg ctg aca cca gaa cag aaa cag aaa aag gcc gcg    384
Ile Ser Gly Leu Gly Leu Thr Pro Glu Gln Lys Gln Lys Lys Ala Ala
        115                 120                 125 tta tct gct tca gaa gga gag gaa gtt cct caa gac aag gcg cca agt    432
Leu Ser Ala Ser Glu Gly Glu Glu Val Pro Gln Asp Lys Ala Pro Ser
    130                 135                 140 cat gtt cct ttc ctg cta att ggt gga ggc aca gct gct ttt gct gca    480
His Val Pro Phe Leu Leu Ile Gly Gly Gly Thr Ala Ala Phe Ala Ala
145                 150                 155                 160 gcc aga tcc atc cgg gct cgg gat cct ggg gcc agg gta ctg att gta    528
Ala Arg Ser Ile Arg Ala Arg Asp Pro Gly Ala Arg Val Leu Ile Val
                165                 170                 175
```

| | | |
|---|---|---|
| tct gaa gat cct gag ctg ccg tac atg cga cct cct ctt tca aaa gaa<br>Ser Glu Asp Pro Glu Leu Pro Tyr Met Arg Pro Pro Leu Ser Lys Glu<br>              180                   185                 190 | | 576 |
| ctg tgg ttt tca gat gac cca aat gtc aca aag aca ctg cga ttc aaa<br>Leu Trp Phe Ser Asp Asp Pro Asn Val Thr Lys Thr Leu Arg Phe Lys<br>      195                   200                   205 | | 624 |
| cag tgg aat gga aaa gag aga agc ata tat ttc cag cca cct tct ttc<br>Gln Trp Asn Gly Lys Glu Arg Ser Ile Tyr Phe Gln Pro Pro Ser Phe<br>210                   215                   220 | | 672 |
| tat gtc tct gct cag gac ctg cct cat att gag aat ggt ggt gtg gct<br>Tyr Val Ser Ala Gln Asp Leu Pro His Ile Glu Asn Gly Gly Val Ala<br>225                   230                   235                 240 | | 720 |
| gtc ctc act ggg aag aag gta gta cag ctg gat gtg aga gac aac atg<br>Val Leu Thr Gly Lys Lys Val Val Gln Leu Asp Val Arg Asp Asn Met<br>              245                   250                 255 | | 768 |
| gtg aaa ctt aat gat ggc tct caa ata acc tat gaa aag tgc ttg att<br>Val Lys Leu Asn Asp Gly Ser Gln Ile Thr Tyr Glu Lys Cys Leu Ile<br>                 260                   265                 270 | | 816 |
| gca aca gga ggt act cca aga agt ctg tct gcc att gat agg gct gga<br>Ala Thr Gly Gly Thr Pro Arg Ser Leu Ser Ala Ile Asp Arg Ala Gly<br>      275                   280                   285 | | 864 |
| gca gag gtg aag agt aga aca acg ctt ttc aga aag att gga gac ttt<br>Ala Glu Val Lys Ser Arg Thr Thr Leu Phe Arg Lys Ile Gly Asp Phe<br>290                   295                   300 | | 912 |
| aga agc ttg gag aag att tca cgg gaa gtc aaa tca att acg att atc<br>Arg Ser Leu Glu Lys Ile Ser Arg Glu Val Lys Ser Ile Thr Ile Ile<br>305                   310                   315                 320 | | 960 |
| ggt ggg ggc ttc ctt ggt agc gaa ctg gcc tgt gct ctt ggc aga aag<br>Gly Gly Gly Phe Leu Gly Ser Glu Leu Ala Cys Ala Leu Gly Arg Lys<br>                 325                   330                 335 | | 1008 |
| gct cga gcc ttg ggc aca gaa gtg att caa ctc ttc ccc gag aaa gga<br>Ala Arg Ala Leu Gly Thr Glu Val Ile Gln Leu Phe Pro Glu Lys Gly<br>              340                   345                 350 | | 1056 |
| aat atg gga aag atc ctc ccc gaa tac ctc agc aac tgg acc atg gaa<br>Asn Met Gly Lys Ile Leu Pro Glu Tyr Leu Ser Asn Trp Thr Met Glu<br>           355                   360                 365 | | 1104 |
| aaa gtc aga cga gag ggg gtt aag gtg atg ccc aat gct att gtg caa<br>Lys Val Arg Arg Glu Gly Val Lys Val Met Pro Asn Ala Ile Val Gln<br>370                 375                   380 | | 1152 |
| tcc gtt gga gtc agc agt ggc aag tta ctt atc aag ctg aaa gac ggc<br>Ser Val Gly Val Ser Ser Gly Lys Leu Leu Ile Lys Leu Lys Asp Gly<br>385                   390                   395                 400 | | 1200 |
| agg aag gta gaa act gac cac ata gtg gca gct gtg ggc ctg gag ccc<br>Arg Lys Val Glu Thr Asp His Ile Val Ala Ala Val Gly Leu Glu Pro<br>              405                   410                 415 | | 1248 |
| aat gtt gag ttg gcc aag act ggt ggc ctg gaa ata gac tca gat ttt<br>Asn Val Glu Leu Ala Lys Thr Gly Gly Leu Glu Ile Asp Ser Asp Phe<br>           420                   425                 430 | | 1296 |
| ggt ggc ttc cgg gta aat gca gag cta caa gca cgc tct aac atc tgg<br>Gly Gly Phe Arg Val Asn Ala Glu Leu Gln Ala Arg Ser Asn Ile Trp<br>              435                   440                 445 | | 1344 |
| gtg gca gga gat gct gca tgc ttc tac gat ata aag ttg gga agg agg<br>Val Ala Gly Asp Ala Ala Cys Phe Tyr Asp Ile Lys Leu Gly Arg Arg<br>450                   455                   460 | | 1392 |
| cgg gta gag cac cat gat cac gct gtt gtg agt gga aga ttg gct gga<br>Arg Val Glu His His Asp His Ala Val Val Ser Gly Arg Leu Ala Gly<br>465                   470                   475                 480 | | 1440 |
| gaa aat atg act gga gct gct aag ccg tac tgg cat cag tca atg ttc<br>Glu Asn Met Thr Gly Ala Ala Lys Pro Tyr Trp His Gln Ser Met Phe<br>              485                   490                 495 | | 1488 |

-continued

```
tgg agt gat ttg ggc ccc gat gtt ggc tat gaa gct att ggt ctt gtg    1536
Trp Ser Asp Leu Gly Pro Asp Val Gly Tyr Glu Ala Ile Gly Leu Val
        500                 505                 510 gac agt agt ttg ccc aca gtt ggt gtt ttt gca aaa gca act gca caa    1584
Asp Ser Ser Leu Pro Thr Val Gly Val Phe Ala Lys Ala Thr Ala Gln
            515                 520                 525 gac aac ccc aaa tct gcc aca gag cag tca gga act ggt atc cga tca    1632
Asp Asn Pro Lys Ser Ala Thr Glu Gln Ser Gly Thr Gly Ile Arg Ser
530                 535                 540 gag agt gag aca gag tcc gag gcc tca gaa att act att cct ccc agc    1680
Glu Ser Glu Thr Glu Ser Glu Ala Ser Glu Ile Thr Ile Pro Pro Ser
545                 550                 555                 560 acc ccg gca gtt cca cag gct ccc gtc cag ggg gag gac tac ggc aaa    1728
Thr Pro Ala Val Pro Gln Ala Pro Val Gln Gly Glu Asp Tyr Gly Lys
                565                 570                 575 ggt gtc atc ttc tac ctc agg gac aaa gtg gtc gtg ggg att gtg cta    1776
Gly Val Ile Phe Tyr Leu Arg Asp Lys Val Val Val Gly Ile Val Leu
            580                 585                 590 tgg aac atc ttt aac cga atg cca ata gca agg aag atc att aag gac    1824
Trp Asn Ile Phe Asn Arg Met Pro Ile Ala Arg Lys Ile Ile Lys Asp
        595                 600                 605 ggt gag cag cat gaa gat ctc aat gaa gta gcc aaa cta ttc aac att    1872
Gly Glu Gln His Glu Asp Leu Asn Glu Val Ala Lys Leu Phe Asn Ile
610                 615                 620 cat gaa gac tgaagcccca cagtggaatt ggcaa                            1906
His Glu Asp
625

<210> SEQ ID NO 8
<211> LENGTH: 627
<212> TYPE: PRT
<213> ORGANISM: Homo sapiens

<400> SEQUENCE: 8

Arg Gly Lys Gly Arg Arg Ser Arg Ile Ala Val Ala Glu Met Phe
 1               5                  10                  15

Arg Cys Gly Gly Leu Ala Ala Gly Ala Leu Lys Gln Lys Leu Val Pro
                20                  25                  30

Leu Val Arg Thr Val Cys Val Arg Ser Pro Arg Gln Arg Asn Arg Leu
            35                  40                  45

Pro Gly Asn Leu Phe Gln Arg Trp His Val Pro Leu Glu Leu Gln Met
        50                  55                  60

Thr Arg Gln Met Ala Ser Ser Gly Ala Ser Gly Gly Lys Ile Asp Asn
 65                 70                  75                  80

Ser Val Leu Val Leu Ile Val Gly Leu Ser Thr Val Gly Ala Gly Ala
                85                  90                  95

Tyr Ala Tyr Lys Thr Met Lys Glu Asp Glu Lys Arg Tyr Asn Glu Arg
            100                 105                 110

Ile Ser Gly Leu Gly Leu Thr Pro Glu Gln Lys Gln Lys Lys Ala Ala
        115                 120                 125

Leu Ser Ala Ser Glu Gly Glu Glu Val Pro Gln Asp Lys Ala Pro Ser
    130                 135                 140

His Val Pro Phe Leu Leu Ile Gly Gly Gly Thr Ala Ala Phe Ala Ala
145                 150                 155                 160

Ala Arg Ser Ile Arg Ala Arg Asp Pro Gly Ala Arg Val Leu Ile Val
                165                 170                 175

Ser Glu Asp Pro Glu Leu Pro Tyr Met Arg Pro Pro Leu Ser Lys Glu
```

-continued

```
            180                 185                 190
Leu Trp Phe Ser Asp Asp Pro Asn Val Thr Lys Thr Leu Arg Phe Lys
    195                 200                 205
Gln Trp Asn Gly Lys Glu Arg Ser Ile Tyr Phe Gln Pro Pro Ser Phe
    210                 215                 220
Tyr Val Ser Ala Gln Asp Leu Pro His Ile Glu Asn Gly Gly Val Ala
225                 230                 235                 240
Val Leu Thr Gly Lys Lys Val Gln Leu Asp Val Arg Asp Asn Met
            245                 250                 255
Val Lys Leu Asn Asp Gly Ser Gln Ile Thr Tyr Glu Lys Cys Leu Ile
            260                 265                 270
Ala Thr Gly Gly Thr Pro Arg Ser Leu Ser Ala Ile Asp Arg Ala Gly
            275                 280                 285
Ala Glu Val Lys Ser Arg Thr Thr Leu Phe Arg Lys Ile Gly Asp Phe
            290                 295                 300
Arg Ser Leu Glu Lys Ile Ser Arg Glu Val Lys Ser Ile Thr Ile Ile
305                 310                 315                 320
Gly Gly Gly Phe Leu Gly Ser Glu Leu Ala Cys Ala Leu Gly Arg Lys
            325                 330                 335
Ala Arg Ala Leu Gly Thr Glu Val Ile Gln Leu Phe Pro Glu Lys Gly
            340                 345                 350
Asn Met Gly Lys Ile Leu Pro Glu Tyr Leu Ser Asn Trp Thr Met Glu
            355                 360                 365
Lys Val Arg Arg Glu Gly Val Lys Val Met Pro Asn Ala Ile Val Gln
            370                 375                 380
Ser Val Gly Val Ser Ser Gly Lys Leu Leu Ile Lys Leu Lys Asp Gly
385                 390                 395                 400
Arg Lys Val Glu Thr Asp His Ile Val Ala Ala Val Gly Leu Glu Pro
            405                 410                 415
Asn Val Glu Leu Ala Lys Thr Gly Gly Leu Glu Ile Asp Ser Asp Phe
            420                 425                 430
Gly Gly Phe Arg Val Asn Ala Glu Leu Gln Ala Arg Ser Asn Ile Trp
            435                 440                 445
Val Ala Gly Asp Ala Ala Cys Phe Tyr Asp Ile Lys Leu Gly Arg Arg
450                 455                 460
Arg Val Glu His His Asp His Ala Val Val Ser Gly Arg Leu Ala Gly
465                 470                 475                 480
Glu Asn Met Thr Gly Ala Ala Lys Pro Tyr Trp His Gln Ser Met Phe
            485                 490                 495
Trp Ser Asp Leu Gly Pro Asp Val Gly Tyr Glu Ala Ile Gly Leu Val
            500                 505                 510
Asp Ser Ser Leu Pro Thr Val Gly Val Phe Ala Lys Ala Thr Ala Gln
            515                 520                 525
Asp Asn Pro Lys Ser Ala Thr Glu Gln Ser Gly Thr Gly Ile Arg Ser
            530                 535                 540
Glu Ser Glu Thr Glu Ser Glu Ala Ser Glu Ile Thr Ile Pro Pro Ser
545                 550                 555                 560
Thr Pro Ala Val Pro Gln Ala Pro Val Gln Gly Glu Asp Tyr Gly Lys
            565                 570                 575
Gly Val Ile Phe Tyr Leu Arg Asp Lys Val Val Gly Ile Val Leu
            580                 585                 590
Trp Asn Ile Phe Asn Arg Met Pro Ile Ala Arg Lys Ile Ile Lys Asp
            595                 600                 605
```

```
Gly Glu Gln His Glu Asp Leu Asn Glu Val Ala Lys Leu Phe Asn Ile
    610                 615                 620

His Glu Asp
625

<210> SEQ ID NO 9
<211> LENGTH: 613
<212> TYPE: PRT
<213> ORGANISM: Homo sapiens
<220> FEATURE:
<223> OTHER INFORMATION: human apoptosis-inducing factor (hAIF);
      hAIF-Gold; mature polypeptide

<400> SEQUENCE: 9

Met Phe Arg Cys Gly Gly Leu Ala Ala Gly Ala Leu Lys Gln Lys Leu
  1               5                  10                  15

Val Pro Leu Val Arg Thr Val Cys Val Arg Ser Pro Arg Gln Arg Asn
                 20                  25                  30

Arg Leu Pro Gly Asn Leu Phe Gln Arg Trp His Val Pro Leu Glu Leu
             35                  40                  45

Gln Met Thr Arg Gln Met Ala Ser Ser Gly Ala Ser Gly Gly Lys Ile
 50                  55                  60

Asp Asn Ser Val Leu Val Leu Ile Val Gly Leu Ser Thr Val Gly Ala
 65                  70                  75                  80

Gly Ala Tyr Ala Tyr Lys Thr Met Lys Glu Asp Glu Lys Arg Tyr Asn
                 85                  90                  95

Glu Arg Ile Ser Gly Leu Gly Leu Thr Pro Glu Gln Lys Gln Lys Lys
            100                 105                 110

Ala Ala Leu Ser Ala Ser Glu Gly Glu Glu Val Pro Gln Asp Lys Ala
        115                 120                 125

Pro Ser His Val Pro Phe Leu Leu Ile Gly Gly Thr Ala Ala Phe
    130                 135                 140

Ala Ala Ala Arg Ser Ile Arg Ala Arg Asp Pro Gly Ala Arg Val Leu
145                 150                 155                 160

Ile Val Ser Glu Asp Pro Glu Leu Pro Tyr Met Arg Pro Pro Leu Ser
                165                 170                 175

Lys Glu Leu Trp Phe Ser Asp Asp Pro Asn Val Thr Lys Thr Leu Arg
            180                 185                 190

Phe Lys Gln Trp Asn Gly Lys Glu Arg Ser Ile Tyr Phe Gln Pro Pro
        195                 200                 205

Ser Phe Tyr Val Ser Ala Gln Asp Leu Pro His Ile Glu Asn Gly Gly
    210                 215                 220

Val Ala Val Leu Thr Gly Lys Lys Val Val Gln Leu Asp Val Arg Asp
225                 230                 235                 240

Asn Met Val Lys Leu Asn Asp Gly Ser Gln Ile Thr Tyr Glu Lys Cys
                245                 250                 255

Leu Ile Ala Thr Gly Gly Thr Pro Arg Ser Leu Ser Ala Ile Asp Arg
            260                 265                 270

Ala Gly Ala Glu Val Lys Ser Arg Thr Thr Leu Phe Arg Lys Ile Gly
        275                 280                 285

Asp Phe Arg Ser Leu Glu Lys Ile Ser Arg Glu Val Lys Ser Ile Thr
    290                 295                 300

Ile Ile Gly Gly Gly Phe Leu Gly Ser Glu Leu Ala Cys Ala Leu Gly
305                 310                 315                 320

Arg Lys Ala Arg Ala Leu Gly Thr Glu Val Ile Gln Leu Phe Pro Glu
```

```
                325                 330                 335
Lys Gly Asn Met Gly Lys Ile Leu Pro Glu Tyr Leu Ser Asn Trp Thr
            340                 345                 350
Met Glu Lys Val Arg Arg Glu Gly Val Lys Val Met Pro Asn Ala Ile
        355                 360                 365
Val Gln Ser Val Gly Val Ser Ser Gly Lys Leu Leu Ile Lys Leu Lys
    370                 375                 380
Asp Gly Arg Lys Val Glu Thr Asp His Ile Val Ala Ala Val Gly Leu
385                 390                 395                 400
Glu Pro Asn Val Glu Leu Ala Lys Thr Gly Gly Leu Glu Ile Asp Ser
                405                 410                 415
Asp Phe Gly Gly Phe Arg Val Asn Ala Glu Leu Gln Ala Arg Ser Asn
            420                 425                 430
Ile Trp Val Ala Gly Asp Ala Ala Cys Phe Tyr Asp Ile Lys Leu Gly
        435                 440                 445
Arg Arg Arg Val Glu His His Asp His Ala Val Val Ser Gly Arg Leu
    450                 455                 460
Ala Gly Glu Asn Met Thr Gly Ala Ala Lys Pro Tyr Trp His Gln Ser
465                 470                 475                 480
Met Phe Trp Ser Asp Leu Gly Pro Asp Val Gly Tyr Glu Ala Ile Gly
                485                 490                 495
Leu Val Asp Ser Ser Leu Pro Thr Val Gly Val Phe Ala Lys Ala Thr
            500                 505                 510
Ala Gln Asp Asn Pro Lys Ser Ala Thr Glu Gln Ser Gly Thr Gly Ile
        515                 520                 525
Arg Ser Glu Ser Glu Thr Glu Ser Glu Ala Ser Glu Ile Thr Ile Pro
    530                 535                 540
Pro Ser Thr Pro Ala Val Pro Gln Ala Pro Val Gln Gly Glu Asp Tyr
545                 550                 555                 560
Gly Lys Gly Val Ile Phe Tyr Leu Arg Asp Lys Val Val Val Gly Ile
                565                 570                 575
Val Leu Trp Asn Ile Phe Asn Arg Met Pro Ile Ala Arg Lys Ile Ile
            580                 585                 590
Lys Asp Gly Glu Gln His Glu Asp Leu Asn Glu Val Ala Lys Leu Phe
        595                 600                 605
Asn Ile His Glu Asp
    610

<210> SEQ ID NO 10
<211> LENGTH: 1894
<212> TYPE: DNA
<213> ORGANISM: Homo sapiens
<220> FEATURE:
<221> NAME/KEY: CDS
<222> LOCATION: (1)..(1869)
<220> FEATURE:
<223> OTHER INFORMATION: human apoptosis-inducing factor (hAIF
      isoform #1); hAIF-alt-exon-Gold

<400> SEQUENCE: 10 aga gga aag gga agg agg agg tcc cga ata gcg gtc gcc gaa atg ttc      48
Arg Gly Lys Gly Arg Arg Arg Ser Arg Ile Ala Val Ala Glu Met Phe
 1               5                  10                  15 cgg tgt gga ggc ctg gcg gcg ggt gct ttg aag cag aag ctg gtg ccc      96
Arg Cys Gly Gly Leu Ala Ala Gly Ala Leu Lys Gln Lys Leu Val Pro
             20                  25                  30 ttg gtg cgg acc gtg tgc gtc cga agc ccg agg cag agg aac cgg ctc     144
```

```
                Leu Val Arg Thr Val Cys Val Arg Ser Pro Arg Gln Arg Asn Arg Leu
                             35                  40                  45 cca gtt gtg cag tct cat cac cta gga tcc cct tct aga tca cta gca      192
Pro Val Val Gln Ser His His Leu Gly Ser Pro Ser Arg Ser Leu Ala
 50                  55                  60 tct aca ggt gct tct ggg aaa gat ggc agc aac cta gtg tac ttc tta      240
Ser Thr Gly Ala Ser Gly Lys Asp Gly Ser Asn Leu Val Tyr Phe Leu
 65                  70                  75                  80 att gta gga gca aca gtc act ggg gca gga gtt tat tat gcc tac aag      288
Ile Val Gly Ala Thr Val Thr Gly Ala Gly Val Tyr Tyr Ala Tyr Lys
                 85                  90                  95 act atg aaa gag gac gaa aaa aga tac aat gaa aga att tca ggg tta      336
Thr Met Lys Glu Asp Glu Lys Arg Tyr Asn Glu Arg Ile Ser Gly Leu
                100                 105                 110 ggg ctg aca cca gaa cag aaa cag aaa aag gcc gcg tta tct gct tca      384
Gly Leu Thr Pro Glu Gln Lys Gln Lys Lys Ala Ala Leu Ser Ala Ser
            115                 120                 125 gaa gga gag gaa gtt cct caa gac aag gcg cca agt cat gtt cct ttc      432
Glu Gly Glu Glu Val Pro Gln Asp Lys Ala Pro Ser His Val Pro Phe
130                 135                 140 ctg cta att ggt gga ggc aca gct gct ttt gct gca gcc aga tcc atc      480
Leu Leu Ile Gly Gly Gly Thr Ala Ala Phe Ala Ala Arg Ser Ile
145                 150                 155                 160 cgg gct cgg gat cct ggg gcc agg gta ctg att gta tct gaa gat cct      528
Arg Ala Arg Asp Pro Gly Ala Arg Val Leu Ile Val Ser Glu Asp Pro
                165                 170                 175 gag ctg ccg tac atg cga cct cct ctt tca aaa gaa ctg tgg ttt tca      576
Glu Leu Pro Tyr Met Arg Pro Pro Leu Ser Lys Glu Leu Trp Phe Ser
            180                 185                 190 gat gac cca aat gtc aca aag aca ctg cga ttc aaa cag tgg aat gga      624
Asp Asp Pro Asn Val Thr Lys Thr Leu Arg Phe Lys Gln Trp Asn Gly
        195                 200                 205 aaa gag aga agc ata tat ttc cag cca cct tct ttc tat gtc tct gct      672
Lys Glu Arg Ser Ile Tyr Phe Gln Pro Pro Ser Phe Tyr Val Ser Ala
    210                 215                 220 cag gac ctg cct cat att gag aat ggt ggt gtg gct gtc ctc act ggg      720
Gln Asp Leu Pro His Ile Glu Asn Gly Gly Val Ala Val Leu Thr Gly
225                 230                 235                 240 aag aag gta gta cag ctg gat gtg aga gac aac atg gtg aaa ctt aat      768
Lys Lys Val Val Gln Leu Asp Val Arg Asp Asn Met Val Lys Leu Asn
                245                 250                 255 gat ggc tct caa ata acc tat gaa aag tgc ttg att gca aca gga ggt      816
Asp Gly Ser Gln Ile Thr Tyr Glu Lys Cys Leu Ile Ala Thr Gly Gly
            260                 265                 270 act cca aga agt ctg tct gcc att gat agg gct gga gca gag gtg aag      864
Thr Pro Arg Ser Leu Ser Ala Ile Asp Arg Ala Gly Ala Glu Val Lys
        275                 280                 285 agt aga aca acg ctt ttc aga aag att gga gac ttt aga agc ttg gag      912
Ser Arg Thr Thr Leu Phe Arg Lys Ile Gly Asp Phe Arg Ser Leu Glu
    290                 295                 300 aag att tca cgg gaa gtc aaa tca att acg att atc ggt ggg ggc ttc      960
Lys Ile Ser Arg Glu Val Lys Ser Ile Thr Ile Ile Gly Gly Gly Phe
305                 310                 315                 320 ctt ggt agc gaa ctg gcc tgt gct ctt gga aga aag gct cga gcc ttg     1008
Leu Gly Ser Glu Leu Ala Cys Ala Leu Gly Arg Lys Ala Arg Ala Leu
                325                 330                 335 ggc aca gaa gtg att caa ctc ttc ccc gag aaa gga aat atg gga aag     1056
Gly Thr Glu Val Ile Gln Leu Phe Pro Glu Lys Gly Asn Met Gly Lys
            340                 345                 350
```

```
atc ctc ccc gaa tac ctc agc aac tgg acc atg gaa aaa gtc aga cga     1104
Ile Leu Pro Glu Tyr Leu Ser Asn Trp Thr Met Glu Lys Val Arg Arg
        355                 360                 365 gag ggg gtt aag gtg atg ccc aat gct att gtg caa tcc gtt gga gtc     1152
Glu Gly Val Lys Val Met Pro Asn Ala Ile Val Gln Ser Val Gly Val
370                 375                 380 agc agt ggc aag tta ctt atc aag ctg aaa gac ggc agg aag gta gaa     1200
Ser Ser Gly Lys Leu Leu Ile Lys Leu Lys Asp Gly Arg Lys Val Glu
385                 390                 395                 400 act gac cac ata gtg gca gct gtg ggc ctg gag ccc aat gtt gag ttg     1248
Thr Asp His Ile Val Ala Ala Val Gly Leu Glu Pro Asn Val Glu Leu
            405                 410                 415 gcc aag act ggt ggc ctg gaa ata gac tca gat ttt ggt ggc ttc cgg     1296
Ala Lys Thr Gly Gly Leu Glu Ile Asp Ser Asp Phe Gly Gly Phe Arg
        420                 425                 430 gta aat gca gag cta caa gca cgc tct aac atc tgg gtg gca gga gat     1344
Val Asn Ala Glu Leu Gln Ala Arg Ser Asn Ile Trp Val Ala Gly Asp
    435                 440                 445 gct gca tgc ttc tac gat ata aag ttg gga agg agg cgg gta gag cac     1392
Ala Ala Cys Phe Tyr Asp Ile Lys Leu Gly Arg Arg Arg Val Glu His
450                 455                 460 cat gat cac gct gtt gtg agt gga aga ttg gct gga gaa aat atg act     1440
His Asp His Ala Val Val Ser Gly Arg Leu Ala Gly Glu Asn Met Thr
465                 470                 475                 480 gga gct gct aag ccg tac tgg cat cag tca atg ttc tgg agt gat ttg     1488
Gly Ala Ala Lys Pro Tyr Trp His Gln Ser Met Phe Trp Ser Asp Leu
            485                 490                 495 ggc ccc gat gtt ggc tat gaa gct att ggt ctt gtg gac agt agt ttg     1536
Gly Pro Asp Val Gly Tyr Glu Ala Ile Gly Leu Val Asp Ser Ser Leu
        500                 505                 510 ccc aca gtt ggt gtt ttt gca aaa gca act gca caa gac aac ccc aaa     1584
Pro Thr Val Gly Val Phe Ala Lys Ala Thr Ala Gln Asp Asn Pro Lys
    515                 520                 525 tct gcc aca gag cag tca gga act ggt atc cga tca gag agt gag aca     1632
Ser Ala Thr Glu Gln Ser Gly Thr Gly Ile Arg Ser Glu Ser Glu Thr
530                 535                 540 gag tcc gag gcc tca gaa att act att cct ccc agc acc ccg gca gtt     1680
Glu Ser Glu Ala Ser Glu Ile Thr Ile Pro Pro Ser Thr Pro Ala Val
545                 550                 555                 560 cca cag gct ccc gtc cag ggg gag gac tac ggc aaa ggt gtc atc ttc     1728
Pro Gln Ala Pro Val Gln Gly Glu Asp Tyr Gly Lys Gly Val Ile Phe
            565                 570                 575 tac ctc agg gac aaa gtg gtc gtg ggg att gtg cta tgg aac atc ttt     1776
Tyr Leu Arg Asp Lys Val Val Val Gly Ile Val Leu Trp Asn Ile Phe
        580                 585                 590 aac cga atg cca ata gca agg aag atc att aag gac ggt gag cag cat     1824
Asn Arg Met Pro Ile Ala Arg Lys Ile Ile Lys Asp Gly Glu Gln His
    595                 600                 605 gaa gat ctc aat gaa gta gcc aaa cta ttc aac att cat gaa gac         1869
Glu Asp Leu Asn Glu Val Ala Lys Leu Phe Asn Ile His Glu Asp
            610                 615                 620 tgaagcccca cagtggaatt ggcaa                                         1894

<210> SEQ ID NO 11
<211> LENGTH: 623
<212> TYPE: PRT
<213> ORGANISM: Homo sapiens

<400> SEQUENCE: 11

Arg Gly Lys Gly Arg Arg Arg Ser Arg Ile Ala Val Ala Glu Met Phe
```

-continued

```
  1               5                    10                   15

Arg Cys Gly Gly Leu Ala Ala Gly Ala Leu Lys Gln Lys Leu Val Pro
                20                  25                  30

Leu Val Arg Thr Val Cys Val Arg Ser Pro Arg Gln Arg Asn Arg Leu
                35                  40                  45

Pro Val Val Gln Ser His His Leu Gly Ser Pro Ser Arg Ser Leu Ala
                50                  55                  60

Ser Thr Gly Ala Ser Gly Lys Asp Gly Ser Asn Leu Val Tyr Phe Leu
 65                  70                  75                  80

Ile Val Gly Ala Thr Val Thr Gly Ala Gly Val Tyr Tyr Ala Tyr Lys
                85                  90                  95

Thr Met Lys Glu Asp Glu Lys Arg Tyr Asn Glu Arg Ile Ser Gly Leu
               100                 105                 110

Gly Leu Thr Pro Glu Gln Lys Gln Lys Ala Ala Leu Ser Ala Ser
               115                 120                 125

Glu Gly Glu Glu Val Pro Gln Asp Lys Ala Pro Ser His Val Pro Phe
               130                 135                 140

Leu Leu Ile Gly Gly Thr Ala Ala Phe Ala Ala Arg Ser Ile
145                 150                 155                 160

Arg Ala Arg Asp Pro Gly Ala Arg Val Leu Ile Val Ser Glu Asp Pro
               165                 170                 175

Glu Leu Pro Tyr Met Arg Pro Pro Leu Ser Lys Glu Leu Trp Phe Ser
               180                 185                 190

Asp Asp Pro Asn Val Thr Lys Thr Leu Arg Phe Lys Gln Trp Asn Gly
               195                 200                 205

Lys Glu Arg Ser Ile Tyr Phe Gln Pro Pro Ser Phe Tyr Val Ser Ala
               210                 215                 220

Gln Asp Leu Pro His Ile Glu Asn Gly Gly Val Ala Val Leu Thr Gly
225                 230                 235                 240

Lys Lys Val Val Gln Leu Asp Val Arg Asp Asn Met Val Lys Leu Asn
               245                 250                 255

Asp Gly Ser Gln Ile Thr Tyr Glu Lys Cys Leu Ile Ala Thr Gly Gly
               260                 265                 270

Thr Pro Arg Ser Leu Ser Ala Ile Asp Arg Ala Gly Ala Glu Val Lys
               275                 280                 285

Ser Arg Thr Thr Leu Phe Arg Lys Ile Gly Asp Phe Arg Ser Leu Glu
               290                 295                 300

Lys Ile Ser Arg Glu Val Lys Ser Ile Thr Ile Ile Gly Gly Gly Phe
305                 310                 315                 320

Leu Gly Ser Glu Leu Ala Cys Ala Leu Gly Arg Lys Ala Arg Ala Leu
               325                 330                 335

Gly Thr Glu Val Ile Gln Leu Phe Pro Glu Lys Gly Asn Met Gly Lys
               340                 345                 350

Ile Leu Pro Glu Tyr Leu Ser Asn Trp Thr Met Glu Lys Val Arg Arg
               355                 360                 365

Glu Gly Val Lys Val Met Pro Asn Ala Ile Val Gln Ser Val Gly Val
               370                 375                 380

Ser Ser Gly Lys Leu Leu Ile Lys Leu Lys Asp Gly Arg Lys Val Glu
385                 390                 395                 400

Thr Asp His Ile Val Ala Ala Val Gly Leu Glu Pro Asn Val Glu Leu
               405                 410                 415

Ala Lys Thr Gly Gly Leu Glu Ile Asp Ser Asp Phe Gly Gly Phe Arg
               420                 425                 430
```

```
Val Asn Ala Glu Leu Gln Ala Arg Ser Asn Ile Trp Val Ala Gly Asp
        435                 440                 445

Ala Ala Cys Phe Tyr Asp Ile Lys Leu Gly Arg Arg Val Glu His
    450                 455                 460

His Asp His Ala Val Val Ser Gly Arg Leu Ala Gly Glu Asn Met Thr
465                 470                 475                 480

Gly Ala Ala Lys Pro Tyr Trp His Gln Ser Met Phe Trp Ser Asp Leu
                485                 490                 495

Gly Pro Asp Val Gly Tyr Glu Ala Ile Gly Leu Val Asp Ser Ser Leu
            500                 505                 510

Pro Thr Val Gly Val Phe Ala Lys Ala Thr Ala Gln Asp Asn Pro Lys
        515                 520                 525

Ser Ala Thr Glu Gln Ser Thr Gly Ile Arg Ser Glu Ser Glu Thr
    530                 535                 540

Glu Ser Glu Ala Ser Glu Ile Thr Ile Pro Pro Ser Thr Pro Ala Val
545                 550                 555                 560

Pro Gln Ala Pro Val Gln Gly Glu Asp Tyr Gly Lys Gly Val Ile Phe
                565                 570                 575

Tyr Leu Arg Asp Lys Val Val Val Gly Ile Val Leu Trp Asn Ile Phe
            580                 585                 590

Asn Arg Met Pro Ile Ala Arg Lys Ile Ile Lys Asp Gly Glu Gln His
        595                 600                 605

Glu Asp Leu Asn Glu Val Ala Lys Leu Phe Asn Ile His Glu Asp
    610                 615                 620

<210> SEQ ID NO 12
<211> LENGTH: 609
<212> TYPE: PRT
<213> ORGANISM: Homo sapiens
<220> FEATURE:
<223> OTHER INFORMATION: human apoptosis-inducing factor (hAIF isoform
      #1 ); hAIF-alt-exon-Gold; mature polypeptide

<400> SEQUENCE: 12

Met Phe Arg Cys Gly Gly Leu Ala Ala Gly Ala Leu Lys Gln Lys Leu
1               5                   10                  15

Val Pro Leu Val Arg Thr Val Cys Val Arg Ser Pro Arg Gln Arg Asn
            20                  25                  30

Arg Leu Pro Val Val Gln Ser His Leu Gly Ser Pro Ser Arg Ser
        35                  40                  45

Leu Ala Ser Thr Gly Ala Ser Gly Lys Asp Gly Ser Asn Leu Val Tyr
    50                  55                  60

Phe Leu Ile Val Gly Ala Thr Val Thr Gly Ala Gly Val Tyr Tyr Ala
65                  70                  75                  80

Tyr Lys Thr Met Lys Glu Asp Glu Lys Arg Tyr Asn Glu Arg Ile Ser
                85                  90                  95

Gly Leu Gly Leu Thr Pro Glu Gln Lys Gln Lys Lys Ala Ala Leu Ser
            100                 105                 110

Ala Ser Glu Gly Glu Glu Val Pro Gln Asp Lys Ala Pro Ser His Val
        115                 120                 125

Pro Phe Leu Leu Ile Gly Gly Gly Thr Ala Ala Phe Ala Ala Ala Arg
    130                 135                 140

Ser Ile Arg Ala Arg Asp Pro Gly Ala Arg Val Leu Ile Val Ser Glu
145                 150                 155                 160

Asp Pro Glu Leu Pro Tyr Met Arg Pro Pro Leu Ser Lys Glu Leu Trp
```

-continued

```
                165                 170                 175
Phe Ser Asp Asp Pro Asn Val Thr Lys Thr Leu Arg Phe Lys Gln Trp
            180                 185                 190
Asn Gly Lys Glu Arg Ser Ile Tyr Phe Gln Pro Pro Ser Phe Tyr Val
        195                 200                 205
Ser Ala Gln Asp Leu Pro His Ile Glu Asn Gly Gly Val Ala Val Leu
    210                 215                 220
Thr Gly Lys Lys Val Val Gln Leu Asp Val Arg Asp Asn Met Val Lys
225                 230                 235                 240
Leu Asn Asp Gly Ser Gln Ile Thr Tyr Glu Lys Cys Leu Ile Ala Thr
                245                 250                 255
Gly Gly Thr Pro Arg Ser Leu Ser Ala Ile Asp Arg Ala Gly Ala Glu
            260                 265                 270
Val Lys Ser Arg Thr Thr Leu Phe Arg Lys Ile Gly Asp Phe Arg Ser
        275                 280                 285
Leu Glu Lys Ile Ser Arg Glu Val Lys Ser Ile Thr Ile Ile Gly Gly
    290                 295                 300
Gly Phe Leu Gly Ser Glu Leu Ala Cys Ala Leu Gly Arg Lys Ala Arg
305                 310                 315                 320
Ala Leu Gly Thr Glu Val Ile Gln Leu Phe Pro Glu Lys Gly Asn Met
                325                 330                 335
Gly Lys Ile Leu Pro Glu Tyr Leu Ser Asn Trp Thr Met Glu Lys Val
            340                 345                 350
Arg Arg Glu Gly Val Lys Val Met Pro Asn Ala Ile Val Gln Ser Val
        355                 360                 365
Gly Val Ser Ser Gly Lys Leu Leu Ile Lys Leu Lys Asp Gly Arg Lys
    370                 375                 380
Val Glu Thr Asp His Ile Val Ala Ala Val Gly Leu Glu Pro Asn Val
385                 390                 395                 400
Glu Leu Ala Lys Thr Gly Gly Leu Glu Ile Asp Ser Asp Phe Gly Gly
                405                 410                 415
Phe Arg Val Asn Ala Glu Leu Gln Ala Arg Ser Asn Ile Trp Val Ala
            420                 425                 430
Gly Asp Ala Ala Cys Phe Tyr Asp Ile Lys Leu Gly Arg Arg Arg Val
        435                 440                 445
Glu His His Asp His Ala Val Val Ser Gly Arg Leu Ala Gly Glu Asn
    450                 455                 460
Met Thr Gly Ala Ala Lys Pro Tyr Trp His Gln Ser Met Phe Trp Ser
465                 470                 475                 480
Asp Leu Gly Pro Asp Val Gly Tyr Glu Ala Ile Gly Leu Val Asp Ser
                485                 490                 495
Ser Leu Pro Thr Val Gly Val Phe Ala Lys Ala Thr Ala Gln Asp Asn
            500                 505                 510
Pro Lys Ser Ala Thr Glu Gln Ser Gly Thr Gly Ile Arg Ser Glu Ser
        515                 520                 525
Glu Thr Glu Ser Glu Ala Ser Glu Ile Thr Ile Pro Pro Ser Thr Pro
    530                 535                 540
Ala Val Pro Gln Ala Pro Val Gln Gly Glu Asp Tyr Gly Lys Gly Val
545                 550                 555                 560
Ile Phe Tyr Leu Arg Asp Lys Val Val Gly Ile Val Leu Trp Asn
                565                 570                 575
Ile Phe Asn Arg Met Pro Ile Ala Arg Lys Ile Ile Lys Asp Gly Glu
            580                 585                 590
```

```
                     Gln His Glu Asp Leu Asn Glu Val Ala Lys Leu Phe Asn Ile His Glu
                             595                 600                 605
                     Asp

<210> SEQ ID NO 13
<211> LENGTH: 1762
<212> TYPE: DNA
<213> ORGANISM: Homo sapiens
<220> FEATURE:
<221> NAME/KEY: CDS
<222> LOCATION: (79)..(1737)
<220> FEATURE:
<223> OTHER INFORMATION: human apoptosis-inducing factor (hAIF isoform
      #2); hAIF-exon-skip-Gold

<400> SEQUENCE: 13
gaggaaaggg aaggaggagg tcccgaatag cggtcgccga aatgttccgg tgtggaggcc      60
tggcggcggg tgctttga agc aga agc tgg tgc cct tgg tgc gga ccg tgt      111
                     Ser Arg Ser Trp Cys Pro Trp Cys Gly Pro Cys
                      1               5                  10 gcg tcc gaa gcc cga ggc aga gga acc ggc tcc cag gcc tac aag act      159
Ala Ser Glu Ala Arg Gly Arg Gly Thr Gly Ser Gln Ala Tyr Lys Thr
                 15                  20                  25 atg aaa gag gac gaa aaa aga tac aat gaa aga att tca ggg tta ggg      207
Met Lys Glu Asp Glu Lys Arg Tyr Asn Glu Arg Ile Ser Gly Leu Gly
         30                  35                  40 ctg aca cca gaa cag aaa cag aaa aag gcc gcg tta tct gct tca gaa      255
Leu Thr Pro Glu Gln Lys Gln Lys Lys Ala Ala Leu Ser Ala Ser Glu
     45                  50                  55 gga gag gaa gtt cct caa gac aag gcg cca agt cat gtt cct ttc ctg      303
Gly Glu Glu Val Pro Gln Asp Lys Ala Pro Ser His Val Pro Phe Leu
 60                  65                  70                  75 cta att ggt gga ggc aca gct gct ttt gct gca gcc aga tcc atc cgg      351
Leu Ile Gly Gly Gly Thr Ala Ala Phe Ala Ala Ala Arg Ser Ile Arg
                 80                  85                  90 gct cgg gat cct ggg gcc agg gta ctg att gta tct gaa gat cct gag      399
Ala Arg Asp Pro Gly Ala Arg Val Leu Ile Val Ser Glu Asp Pro Glu
             95                 100                 105 ctg ccg tac atg cga cct cct ctt tca aaa gaa ctg tgg ttt tca gat      447
Leu Pro Tyr Met Arg Pro Pro Leu Ser Lys Glu Leu Trp Phe Ser Asp
        110                 115                 120 gac cca aat gtc aca aag aca ctg cga ttc aaa cag tgg aat gga aaa      495
Asp Pro Asn Val Thr Lys Thr Leu Arg Phe Lys Gln Trp Asn Gly Lys
    125                 130                 135 gag aga agc ata tat ttc cag cca cct tct ttc tat gtc tct gct cag      543
Glu Arg Ser Ile Tyr Phe Gln Pro Pro Ser Phe Tyr Val Ser Ala Gln
140                 145                 150                 155 gac ctg cct cat att gag aat ggt ggt gtg gct gtc ctc act ggg aag      591
Asp Leu Pro His Ile Glu Asn Gly Gly Val Ala Val Leu Thr Gly Lys
                160                 165                 170 aag gta gta cag ctg gat gtg aga gac aac atg gtg aaa ctt aat gat      639
Lys Val Val Gln Leu Asp Val Arg Asp Asn Met Val Lys Leu Asn Asp
            175                 180                 185 ggc tct caa ata acc tat gaa aag tgc ttg att gca aca gga ggt act      687
Gly Ser Gln Ile Thr Tyr Glu Lys Cys Leu Ile Ala Thr Gly Gly Thr
        190                 195                 200 cca aga agt ctg tct gcc att gat agg gct gga gca gag gtg aag agt      735
Pro Arg Ser Leu Ser Ala Ile Asp Arg Ala Gly Ala Glu Val Lys Ser
    205                 210                 215 aga aca acg ctt ttc aga aag att gga gac ttt aga agc ttg gag aag      783
Arg Thr Thr Leu Phe Arg Lys Ile Gly Asp Phe Arg Ser Leu Glu Lys
```

-continued

```
                220                 225                 230                 235
att tca cgg gaa gtc aaa tca att acg att atc ggt ggg ggc ttc ctt             831
Ile Ser Arg Glu Val Lys Ser Ile Thr Ile Ile Gly Gly Gly Phe Leu
                240                 245                 250 ggt agc gaa ctg gcc tgt gct ctt ggc aga aag gct cga gcc ttg ggc             879
Gly Ser Glu Leu Ala Cys Ala Leu Gly Arg Lys Ala Arg Ala Leu Gly
            255                 260                 265 aca gaa gtg att caa ctc ttc ccc gag aaa gga aat atg gga aag atc             927
Thr Glu Val Ile Gln Leu Phe Pro Glu Lys Gly Asn Met Gly Lys Ile
        270                 275                 280 ctc ccc gaa tac ctc agc aac tgg acc atg gaa aaa gtc aga cga gag             975
Leu Pro Glu Tyr Leu Ser Asn Trp Thr Met Glu Lys Val Arg Arg Glu
    285                 290                 295 ggg gtt aag gtg atg ccc aat gct att gtg caa tcc gtt gga gtc agc            1023
Gly Val Lys Val Met Pro Asn Ala Ile Val Gln Ser Val Gly Val Ser
300                 305                 310                 315 agt ggc aag tta ctt atc aag ctg aaa gac ggc agg aag gta gaa act            1071
Ser Gly Lys Leu Leu Ile Lys Leu Lys Asp Gly Arg Lys Val Glu Thr
                320                 325                 330 gac cac ata gtg gca gct gtg ggc ctg gag ccc aat gtt gag ttg gcc            1119
Asp His Ile Val Ala Ala Val Gly Leu Glu Pro Asn Val Glu Leu Ala
            335                 340                 345 aag act ggt ggc ctg gaa ata gac tca gat ttt ggt ggc ttc cgg gta            1167
Lys Thr Gly Gly Leu Glu Ile Asp Ser Asp Phe Gly Gly Phe Arg Val
        350                 355                 360 aat gca gag cta caa gca cgc tct aac atc tgg gtg gca gga gat gct            1215
Asn Ala Glu Leu Gln Ala Arg Ser Asn Ile Trp Val Ala Gly Asp Ala
    365                 370                 375 gca tgc ttc tac gat ata aag ttg gga agg agg cgg gta gag cac cat            1263
Ala Cys Phe Tyr Asp Ile Lys Leu Gly Arg Arg Arg Val Glu His His
380                 385                 390                 395 gat cac gct gtt gtg agt gga aga ttg gct gga gaa aat atg act gga            1311
Asp His Ala Val Val Ser Gly Arg Leu Ala Gly Glu Asn Met Thr Gly
                400                 405                 410 gct gct aag ccg tac tgg cat cag tca atg ttc tgg agt gat ttg ggc            1359
Ala Ala Lys Pro Tyr Trp His Gln Ser Met Phe Trp Ser Asp Leu Gly
            415                 420                 425 ccc gat gtt ggc tat gaa gct att ggt ctt gtg gac agt agt ttg ccc            1407
Pro Asp Val Gly Tyr Glu Ala Ile Gly Leu Val Asp Ser Ser Leu Pro
        430                 435                 440 aca gtt ggt gtt ttt gca aaa gca act gca caa gac aac ccc aaa tct            1455
Thr Val Gly Val Phe Ala Lys Ala Thr Ala Gln Asp Asn Pro Lys Ser
    445                 450                 455 gcc aca gag cag tca gga act ggt atc cga tca gag agt gag aca gag            1503
Ala Thr Glu Gln Ser Gly Thr Gly Ile Arg Ser Glu Ser Glu Thr Glu
460                 465                 470                 475 tcc gag gcc tca gaa att act att cct ccc agc acc ccg gca gtt cca            1551
Ser Glu Ala Ser Glu Ile Thr Ile Pro Pro Ser Thr Pro Ala Val Pro
                480                 485                 490 cag gct ccc gtc cag ggg gag gac tac ggc aaa ggt gtc atc ttc tac            1599
Gln Ala Pro Val Gln Gly Glu Asp Tyr Gly Lys Gly Val Ile Phe Tyr
            495                 500                 505 ctc agg gac aaa gtg gtc gtg ggg att gtg cta tgg aac atc ttt aac            1647
Leu Arg Asp Lys Val Val Val Gly Ile Val Leu Trp Asn Ile Phe Asn
        510                 515                 520 cga atg cca ata gca agg aag atc att aag gac ggt gag cag cat gaa            1695
Arg Met Pro Ile Ala Arg Lys Ile Ile Lys Asp Gly Glu Gln His Glu
    525                 530                 535 gat ctc aat gaa gta gcc aaa cta ttc aac att cat gaa gac                    1737
Asp Leu Asn Glu Val Ala Lys Leu Phe Asn Ile His Glu Asp
```

```
Asp Leu Asn Glu Val Ala Lys Leu Phe Asn Ile His Glu Asp
        540                 545                 550
tgaagcccca cagtggaatt ggcaa                                              1762

<210> SEQ ID NO 14
<211> LENGTH: 553
<212> TYPE: PRT
<213> ORGANISM: Homo sapiens

<400> SEQUENCE: 14

Ser Arg Ser Trp Cys Pro Trp Cys Gly Pro Cys Ala Ser Glu Ala Arg
  1               5                  10                  15

Gly Arg Gly Thr Gly Ser Gln Ala Tyr Lys Thr Met Lys Glu Asp Glu
             20                  25                  30

Lys Arg Tyr Asn Glu Arg Ile Ser Gly Leu Gly Leu Thr Pro Glu Gln
         35                  40                  45

Lys Gln Lys Lys Ala Ala Leu Ser Ala Ser Glu Gly Glu Glu Val Pro
     50                  55                  60

Gln Asp Lys Ala Pro Ser His Val Pro Phe Leu Leu Ile Gly Gly Gly
 65                  70                  75                  80

Thr Ala Ala Phe Ala Ala Ala Arg Ser Ile Arg Ala Arg Asp Pro Gly
                 85                  90                  95

Ala Arg Val Leu Ile Val Ser Glu Asp Pro Glu Leu Pro Tyr Met Arg
            100                 105                 110

Pro Pro Leu Ser Lys Glu Leu Trp Phe Ser Asp Asp Pro Asn Val Thr
        115                 120                 125

Lys Thr Leu Arg Phe Lys Gln Trp Asn Gly Lys Glu Arg Ser Ile Tyr
    130                 135                 140

Phe Gln Pro Pro Ser Phe Tyr Val Ser Ala Gln Asp Leu Pro His Ile
145                 150                 155                 160

Glu Asn Gly Gly Val Ala Val Leu Thr Gly Lys Lys Val Val Gln Leu
                165                 170                 175

Asp Val Arg Asp Asn Met Val Lys Leu Asn Asp Gly Ser Gln Ile Thr
            180                 185                 190

Tyr Glu Lys Cys Leu Ile Ala Thr Gly Gly Thr Pro Arg Ser Leu Ser
        195                 200                 205

Ala Ile Asp Arg Ala Gly Ala Glu Val Lys Ser Arg Thr Thr Leu Phe
    210                 215                 220

Arg Lys Ile Gly Asp Phe Arg Ser Leu Glu Lys Ile Ser Arg Glu Val
225                 230                 235                 240

Lys Ser Ile Thr Ile Ile Gly Gly Gly Phe Leu Gly Ser Glu Leu Ala
                245                 250                 255

Cys Ala Leu Gly Arg Lys Ala Arg Ala Leu Gly Thr Glu Val Ile Gln
            260                 265                 270

Leu Phe Pro Glu Lys Gly Asn Met Gly Lys Ile Leu Pro Glu Tyr Leu
        275                 280                 285

Ser Asn Trp Thr Met Glu Lys Val Arg Arg Glu Gly Val Lys Val Met
    290                 295                 300

Pro Asn Ala Ile Val Gln Ser Val Gly Val Ser Ser Gly Lys Leu Leu
305                 310                 315                 320

Ile Lys Leu Lys Asp Gly Arg Lys Val Glu Thr Asp His Ile Val Ala
                325                 330                 335

Ala Val Gly Leu Glu Pro Asn Val Glu Leu Ala Lys Thr Gly Gly Leu
            340                 345                 350

Glu Ile Asp Ser Asp Phe Gly Gly Phe Arg Val Asn Ala Glu Leu Gln
```

```
                355                 360                 365
Ala Arg Ser Asn Ile Trp Val Ala Gly Asp Ala Ala Cys Phe Tyr Asp
        370                 375                 380

Ile Lys Leu Gly Arg Arg Val Glu His His Asp His Ala Val Val
385                 390                 395                 400

Ser Gly Arg Leu Ala Gly Glu Asn Met Thr Gly Ala Ala Lys Pro Tyr
                405                 410                 415

Trp His Gln Ser Met Phe Trp Ser Asp Leu Gly Pro Asp Val Gly Tyr
            420                 425                 430

Glu Ala Ile Gly Leu Val Asp Ser Ser Leu Pro Thr Val Gly Val Phe
        435                 440                 445

Ala Lys Ala Thr Ala Gln Asp Asn Pro Lys Ser Ala Thr Glu Gln Ser
    450                 455                 460

Gly Thr Gly Ile Arg Ser Glu Ser Glu Thr Glu Ser Glu Ala Ser Glu
465                 470                 475                 480

Ile Thr Ile Pro Pro Ser Thr Pro Ala Val Pro Gln Ala Pro Val Gln
                485                 490                 495

Gly Glu Asp Tyr Gly Lys Gly Val Ile Phe Tyr Leu Arg Asp Lys Val
            500                 505                 510

Val Val Gly Ile Val Leu Trp Asn Ile Phe Asn Arg Met Pro Ile Ala
        515                 520                 525

Arg Lys Ile Ile Lys Asp Gly Glu Gln His Glu Asp Leu Asn Glu Val
    530                 535                 540

Ala Lys Leu Phe Asn Ile His Glu Asp
545                 550

<210> SEQ ID NO 15
<211> LENGTH: 526
<212> TYPE: PRT
<213> ORGANISM: Homo sapiens
<220> FEATURE:
<223> OTHER INFORMATION: human apoptosis-inducing factor (hAIF isoform
      #2); hAIF-exon-skip-Gold; mature polypeptide

<400> SEQUENCE: 15

Met Lys Glu Asp Glu Lys Arg Tyr Asn Glu Arg Ile Ser Gly Leu Gly
1               5                   10                  15

Leu Thr Pro Glu Gln Lys Gln Lys Ala Ala Leu Ser Ala Ser Glu
            20                  25                  30

Gly Glu Glu Val Pro Gln Asp Lys Ala Pro Ser His Val Pro Phe Leu
        35                  40                  45

Leu Ile Gly Gly Gly Thr Ala Ala Phe Ala Ala Ala Arg Ser Ile Arg
    50                  55                  60

Ala Arg Asp Pro Gly Ala Arg Val Leu Ile Val Ser Glu Asp Pro Glu
65                  70                  75                  80

Leu Pro Tyr Met Arg Pro Pro Leu Ser Lys Glu Leu Trp Phe Ser Asp
                85                  90                  95

Asp Pro Asn Val Thr Lys Thr Leu Arg Phe Lys Gln Trp Asn Gly Lys
            100                 105                 110

Glu Arg Ser Ile Tyr Phe Gln Pro Pro Ser Phe Tyr Val Ser Ala Gln
        115                 120                 125

Asp Leu Pro His Ile Glu Asn Gly Gly Val Ala Val Leu Thr Gly Lys
    130                 135                 140

Lys Val Val Gln Leu Asp Val Arg Asp Asn Met Val Lys Leu Asn Asp
145                 150                 155                 160
```

-continued

Gly Ser Gln Ile Thr Tyr Glu Lys Cys Leu Ile Ala Thr Gly Gly Thr
                165                 170                 175

Pro Arg Ser Leu Ser Ala Ile Asp Arg Ala Gly Ala Glu Val Lys Ser
            180                 185                 190

Arg Thr Thr Leu Phe Arg Lys Ile Gly Asp Phe Arg Ser Leu Glu Lys
        195                 200                 205

Ile Ser Arg Glu Val Lys Ser Ile Thr Ile Ile Gly Gly Phe Leu
210                 215                 220

Gly Ser Glu Leu Ala Cys Ala Leu Gly Arg Lys Ala Arg Ala Leu Gly
225                 230                 235                 240

Thr Glu Val Ile Gln Leu Phe Pro Glu Lys Gly Asn Met Gly Lys Ile
                245                 250                 255

Leu Pro Glu Tyr Leu Ser Asn Trp Thr Met Glu Lys Val Arg Arg Glu
            260                 265                 270

Gly Val Lys Val Met Pro Asn Ala Ile Val Gln Ser Val Gly Val Ser
        275                 280                 285

Ser Gly Lys Leu Leu Ile Lys Leu Lys Asp Gly Arg Lys Val Glu Thr
    290                 295                 300

Asp His Ile Val Ala Ala Val Gly Leu Glu Pro Asn Val Glu Leu Ala
305                 310                 315                 320

Lys Thr Gly Gly Leu Glu Ile Asp Ser Asp Phe Gly Gly Phe Arg Val
                325                 330                 335

Asn Ala Glu Leu Gln Ala Arg Ser Asn Ile Trp Val Ala Gly Asp Ala
            340                 345                 350

Ala Cys Phe Tyr Asp Ile Lys Leu Gly Arg Arg Arg Val Glu His His
        355                 360                 365

Asp His Ala Val Val Ser Gly Arg Leu Ala Gly Glu Asn Met Thr Gly
    370                 375                 380

Ala Ala Lys Pro Tyr Trp His Gln Ser Met Phe Trp Ser Asp Leu Gly
385                 390                 395                 400

Pro Asp Val Gly Tyr Glu Ala Ile Gly Leu Val Asp Ser Ser Leu Pro
                405                 410                 415

Thr Val Gly Val Phe Ala Lys Ala Thr Ala Gln Asp Asn Pro Lys Ser
            420                 425                 430

Ala Thr Glu Gln Ser Gly Thr Gly Ile Arg Ser Glu Ser Glu Thr Glu
        435                 440                 445

Ser Glu Ala Ser Glu Ile Thr Ile Pro Pro Ser Thr Pro Ala Val Pro
    450                 455                 460

Gln Ala Pro Val Gln Gly Asp Tyr Gly Lys Gly Val Ile Phe Tyr
465                 470                 475                 480

Leu Arg Asp Lys Val Val Val Gly Ile Val Leu Trp Asn Ile Phe Asn
                485                 490                 495

Arg Met Pro Ile Ala Arg Lys Ile Ile Lys Asp Gly Glu Gln His Glu
            500                 505                 510

Asp Leu Asn Glu Val Ala Lys Leu Phe Asn Ile His Glu Asp
        515                 520                 525

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 16
acggtgcgtg gaaggaaaag gaagg                                              25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 17
cgccagggat ggaaaagtgc ttgtg                                              25

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 18
tcagttcctc agatcagggc acc                                                23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 19
aaaaacacca actgtgggca aac                                                23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 20
catcgatagg gctggagcag agg                                                23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 21
tttccatggt ccagttgctg agg                                                23

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 22
gagccacgtg gtctgtttga cccgttcg                                           28

<210> SEQ ID NO 23
<211> LENGTH: 28
<212> TYPE: DNA
<213> ORGANISM: Artificial Sequence -continued

```
<220> FEATURE:
<223> OTHER INFORMATION: Description of Artificial Sequence: primer

<400> SEQUENCE: 23
ggagttctgc atttacccgg aagccacc                                          28

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 24
gagaggaaag ggaaggagga ggtc                                              24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 25
ttgccaattc cactgtgggg cttc                                              24
```